US007238345B1

(12) United States Patent
Seid, Jr. et al.

(10) Patent No.: US 7,238,345 B1
(45) Date of Patent: Jul. 3, 2007

(54) RECOMBINANT MICROORGANISM EXPRESSING MENINGOCOCCAL CLASS 1 OUTER MEMBRANE PROTEIN

(75) Inventors: Robert C. Seid, Jr., San Francisco, CA (US); Peter R. Paradiso, Pittsford, NY (US); Jan T. Poolman, Broek in Waterland (NL); Peter Hoogerhout, Bilthoven (NL); Emmanuel J. H. J. Wiertz, Utrecht (NL); Peter van der Ley, Utrecht (NL); John Edward Heckels, Romsey (GB); Ian Nicholas Clarke, Southampton (GB)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 08/461,651

(22) Filed: Jun. 5, 1995

Related U.S. Application Data

(60) Division of application No. 08/204,808, filed on Feb. 15, 1994, now Pat. No. 7,118,757, which is a continuation of application No. 07/691,005, filed as application No. PCT/US89/05678 on Dec. 19, 1989, now abandoned.

(30) Foreign Application Priority Data

| | | |
|---|---|---|
| Dec. 19, 1988 | (NL) | .................................. 8803111 |
| Jan. 6, 1989 | (NL) | .................................. 8900036 |
| Jun. 26, 1989 | (NL) | .................................. 8901612 |

(51) Int. Cl.

| | |
|---|---|
| *A01N 63/00* | (2006.01) |
| *A61K 39/02* | (2006.01) |
| *A61K 39/095* | (2006.01) |
| *C07H 21/04* | (2006.01) |
| *C12N 15/74* | (2006.01) |
| *C12N 15/09* | (2006.01) |
| *C12P 21/04* | (2006.01) |

(52) U.S. Cl. .............. 424/93.2; 424/200.1; 424/234.1; 424/93.2; 424/93.4; 424/192.1; 424/250.1; 424/93.48; 536/23.7; 435/230.1; 435/71.1; 435/69.3; 435/69.7

(58) Field of Classification Search ............ 424/234.1, 424/184.1, 185.1, 192.1, 249.1, 250.1, 93.2, 424/93.4, 93.48, 200.1; 530/350, 300; 514/898, 514/320.1; 435/71.1, 69.3
See application file for complete search history.

(56) References Cited

U.S. PATENT DOCUMENTS

| | | | | |
|---|---|---|---|---|
| 4,271,147 A | | 6/1981 | Helting et al. | 424/92 |
| 4,601,903 A | | 7/1986 | Frasch | 424/92 |
| 4,673,574 A | | 6/1987 | Anderson | 424/92 |
| 4,707,543 A | | 11/1987 | Zollinger et al. | 530/402 |
| 4,762,713 A | | 8/1988 | Anderson | 424/92 |
| 5,182,109 A | | 1/1993 | Tamura et al. | 424/92 |
| 5,196,510 A | * | 3/1993 | Rodwell et al. | 530/324 |
| 5,691,449 A | * | 11/1997 | Paradiso et al. | 530/350 |
| 5,736,361 A | * | 4/1998 | Carbonetti et al. | 435/69.3 |
| 5,780,261 A | * | 7/1998 | Kontinen et al. | 435/69.1 |
| 6,130,082 A | * | 10/2000 | Majarian et al. | 435/252.3 |
| 6,348,332 B1 | * | 2/2002 | Carbonetti et al. | 435/69.3 |

FOREIGN PATENT DOCUMENTS

| | | | |
|---|---|---|---|
| EP | 0 011 243 | | 5/1980 |
| EP | 0 090 660 | | 10/1983 |
| EP | 0 109 688 | | 5/1984 |
| EP | 0 145 359 | | 1/1985 |
| EP | 0 102 401 | | 5/1986 |
| EP | 0 182 401 | | 5/1986 |
| EP | 0 301 992 | | 2/1989 |
| EP | 0 351 604 | | 1/1990 |
| EP | 0 372 501 | | 6/1990 |
| EP | 0 449 958 B9 | | 10/1991 |
| EP | 0474313 | * | 3/1992 |
| JP | 64-29321 | * | 1/1989 |
| NL | PT 87935 A | | 8/1988 |
| NL | CN 1030443 A | | 1/1989 |
| WO | WO 89/04873 | * | 6/1989 |
| WO | WO 89/10967 | | 11/1989 |
| WO | WO 90/06696 | | 6/1990 |
| WO | WO 94/08021 | * | 4/1994 |

OTHER PUBLICATIONS

Illustrated Stedman's Medical Dictionary, 24th Edition, Williams & Wilkins, Baltimore/London, p. 1120, 1983.*
Bowie et al. Science 247: 1306-1310, 1990.*
Burgess et al. J. Cell Biol. 111: 2129-2138, 1990.*
Lazar et al. Mol. Cellular Biol. 8: 1247-1252, 1988.*
Zhou et al. Mol. Microbiol. 23: 799-812, 1997.*
Maedland et al. Mol. APMIS 97: 774-780, Sep. 1989.*
Maiden et al. Mol. Microbiol. 5: 727-736, 1991.*
Carbonetti et al. PNAS 85: 6841-6845, Sep. 1988.*
McGuinness et al. J. Exp. Med. 171: 1871-1882, Jun. 1990.*
Wiertz et al. Eleventh American Peptide Symposium. La Jolla, CA, Jul. 9-4, 1989, pp. 731-732.*
Sambrook et al. Molecular Cloning: A Laboratory Manual. Second Edition, Cold Spring Harbor, pp. 17.1-17.44, 1989.*
Illustrated Stedman's Medical Dictionary, 24th Edition, p. 1051, 1982.*
Palker et al. J. Immunology 142: 3612-3619, 1989.*
McCarvil et al. Mol. Microbiol. 10: 203-213, 1993.*
White et al. Mol. Microbiol. 4: 769-776, 1990.*
Beuvery, E. C., et al., "Preparation and Physiocochemical and Immunological Characterization of Polysaccharide-Outer Membrane Protein Complexes of *Neisseria meningitidis,*" *Infection and Immunity,* 40(1):369-380 (1983).

(Continued)

*Primary Examiner*—S. Devi
(74) *Attorney, Agent, or Firm*—Hamilton, Brook, Smith & Reynolds, P.C.

(57) ABSTRACT

Outer-membrane vesicles, Class 1 outer membrane proteins of *Neisseria meningitidis,* fragments or oligopeptides containing epitopes of the Class I OMP can be used to immunize against meningococcal disease.

31 Claims, 21 Drawing Sheets

OTHER PUBLICATIONS

Jiskoot, W., et al., "Immunogenic Activity of Gonococcal Protein I in Mice with Three Different Lipoidal Adjuvants Delivered in Liposomes and in Complexes," *Infection and Immunity*, 54(2):333-338 (1986).

Wang, L. Y., and Frasch, C. E., "Development of a *Neisseria meningitidis* Group B Serotype 2b Protein Vaccine and Evaluation in a Mouse Model," *Infection and Immunity*, 46(2):408-414 (1984).

Teerlink, T., et al., "Synergistic Effect of Detergents and Aluminium Phosphate on the Humoral Immune Response to Bacterial and Viral Membrane Proteins," *Vaccine*, 5(4):307-314 (1987).

Gregoriadis, G., et al., "Liposomes as Immunological Adjuvants: Antigen Incorporation Studies," *Vaccine*, 5(2):145-151 (1987).

Tsai, C-M., and Frasch, C. E., "Chemical Analysis of Major Outer Membrane Proteins of *Neisseria meningitidis:* Comparison of Serotypes 2 and 11," *Journal of Bacteriology*, 141(1):169-176 (1980).

Tsai, C-M., et al., "Five Structural Classes of Major Outer Membrane Proteins in *Neisseria meningitidis,*" *J. Bacteriol.*, 146(1):69-78 (1981). (From *Chem. Abstracts*, 1981, 94, Abstract No. 205111z).

Barlow, A. K., et al., "Molecular Cloning and Expression of *Neisseria meningitidis* Class 1 Outer Membrane Protein in *Escherichia coli* K-12," *Infection and Immunity*, 55(11):2734-2740 (1987).

Wedege, E., et al., "Restoration of Antibody Binding to Blotted Meningococcal Outer Membrane Proteins Using Various Detergents," *Journal of Immunological Methods*, 113:51-59 (1988).

Abdillahi, H. and Poolman, J. T., "Definition of Meningococcal Class 1 OMP Subtyping Antigens by Monoclonal Antibodies," *Microbiol. Immunol.*, 47(3):139-144 (1988). (From *Biological Abstracts*, 1989, 87, Abstract No. 115445).

Poolman, J. T., et al., "Purification, Cyanogen Bromide Cleavage, and Amino Terminus Sequencing of Class 1 and Class 3 Outer Membrane Proteins of Meningococci," *Infection and Immunity*, 57(3):1005-1007 (1989).

Barlow, A. K., et al., "The Class-1 Outer Membrane Protein of *Neisseria—Meningitidis:* Gene Sequence and Structural and Immunological Similarities to Gonococcal Porins," *Molecular Microbiology*, 3(2):131-139 (1989).

Poolman, J. T., "Immunogenicity of Meningococcal Antigens as Detected in Patient Sera," *Infection and Immunity*, 40(1):398-406 (1983).

Frasch, C. E., et al., "Immunogenicity and Clinical Evaluation of Group B *Neisseria meningitidis* Outer Membrane Protein Vaccines." In *Seminars in Infectious Disease, vol. IV: Bacterial Vaccines,* J. B. Robbins, et al., eds. (NY: Thieme-Stratton Inc.), pp. 263-267 (1982).

Mäkelä, P. H., et al., "Porins: The Major Outer Membrane Proteins of Enteric Bacteria as Protective Antigens." In *Seminars in Infectious Disease, vol. IV: Bacterial Vaccines,* J. B. Robbins, et al., eds. (NY: Thieme-Stratton Inc.), pp. 360-365 (1982).

Newton, S. M. C., et al., "Immune Response to Cholera Toxin Epitope Inserted in *Salmonella Flagellin,*" *Science*, 244:70-72 (1989).

Bessler, W. G., et al., "Specific Antibodies Elicited by Antigen Covalently Linked to a Synthetic Adjuvant," *Immunobiol.*, 170:239-244 (1985).

Lerner, R. A., "Tapping the Immunological Repertoire to Produce Antibodies of Predetermined Specificity," *Nature*, 299:592-596 (1982).

Lowell, George H., et al., "Peptides Bound to Proteosomes Via Hydrophobic Feet Become Highly Immunogenic Without Adjuvants," *Journal of Experimental Medicine*, 167:658-663 (1988).

Saukkonen, K., et al, "Protective Efficacy of Monoclonal Antibodies to Class 1 and Class 3 Outer Membrane Proteins of *Neisseria meningitidis* B:15:P1.16 in Infant Rat Infection Model: New Prospects for Vaccine Development," *Microbial Pathogensis*, 3:261-267 (1987).

Mandrell, R.E., et al., "Human Immune Response to Meningococcal Outer Membrane Protein Epitopes After Natural Infection or Vaccination," *Infection and Immunity*, 57:1590-1598 (1989).

Hirama, M., "Cloning of cDNAs with Vectors Permitting Expression in Host Cells." In *Immunological Methods, vol. III,* Lefkovits, I. and Pernis, B., eds. (Orlando: Academic Press, Inc.), p. 52 (1985).

Wiertz, E.J.H.J., et al., "Human T-Cell Epitope Mapping of the Meningococcal Class 1 Outer Membrane Protein." Symposium on Immunogenicity, Steamboat Springs, CO, Jan. 21-28, 1989. (From *Biological Abstracts/RRM,* BR36:126147, Abstract No. 89:258923.) *J. Cell. Biochem.* suppl. 0 (13 Part A). 1989. 326.

International Search Report from PCT Application No. 89/05678 (Publication No. WO 90/06696, filed Dec. 19, 1989.

Wedege, E. and L. Oddvar Frohølm, "Human Antibody Response to a Group B Serotype 2a Meningococcal Vaccine Determined by Immunoblotting," *Infection and Immunity*, 51(2):571-578 (1986).

Frasch, C.E., et al., "Immune Responses of Adults and Children to Group B *Neisseria meningitidis* Outer Membrane Protein Vaccines," *Bacterial Vaccines*, 262-272, Academic Press (1988).

Beuvery, E.C., et al., "Characteristics of an Alternative Meningococcal Type 15 (P1. 16) Outer Membrane Protein Vaccine," *Antonie van Leeuwenhoek* 52:232-235 (1986). International Symposium—Meningococcal Disease in N.W. Europe.

Poolman, J.T., et al., "Comparison of Meningococcal Outer Membrane Protein Vaccines Solubilized with Detergent or C Polysaccharide," *Antonie van Leeuwenhoek*, 53:413-419 (1987).

Wiertz, E.J.H.J., et al., "Human T-Cell Epitope Mapping of the Meningococcal Class 1 Outer Membrane Protein," Symposium on Immunogenicity, Steamboat Springs, CO. Jan. 21-28, 1989. (From *Biological Abstracts/RRM,* BR36:126147, Abstract No. 89:258923) *J. Cell Biochem Suppl.* 0 (13 Part A) (1989); Abstract C 722.

Abdillahi, H. and Poolman, J.T., "*Neisseria meningitidis* group B serosubtyping using monoclonal antibodies in whole-cell Elisa," *Microbial Pathogenesis* 4:27-32 (1988).

van der Ley, P., et al., "Topology of Outer Membrane Porins in Pathogenic *Neisseria* spp.," *Infection and Immunity* 59(9):2963-2971 (1991).

Poolman, Y. and Chanseiseid, R. (inventors), "Manufacture of vaccines from membranous proteins of *Neisseria meningitidis* (class 1)," CAPLUS abstract for JP 01029321 A2, EP 298550 A1 and CN 1030443 A. Accession No. 1989:619262 CAPLUS; Document No. 111:219262. American Chemical Society.

van der Ley, P. and Poolman, J.T., "Construction of a Multivalent Meningococcal Vaccine Strain Based on the Class 1 Outer Membrane Protein," *Infection and Immunity* 60(8):3156-3161 (1992).

Barlow, A.K., J.E. Heckels and I.N.Clarke. "Molecular Cloning and Expression of *Neisseria meningitidis* Class 1 Outer Membrane Protein in *Escherichia coli* K-12" In: *Proceedings of the Symposium (Abstracts Booklet)*, 110th Meeting of the Society for General Microbiology, University of Southampton, UK, Jan. 6-8, 1988 (Abstract No. P13, p. 14).

\* cited by examiner

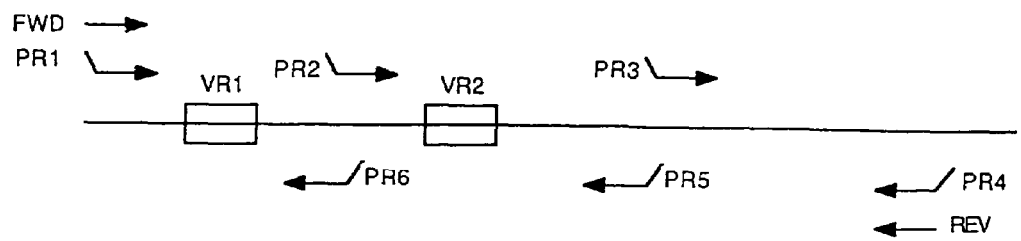
PCR PRODUCTS:
FWD + PR4
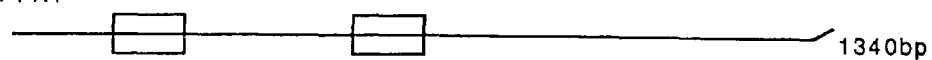
1340bp
FWD + PR5
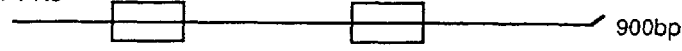
900bp
FWD + PR6
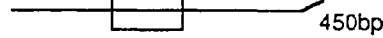
450bp
REV + PR1
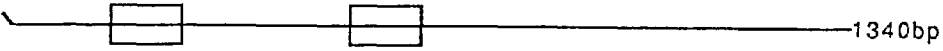
1340bp
REV + PR2
900bp
REV + PR3
450bp
FIG. 1

FIG. 2

```
                                                      20                                      30
        SEQ ID
        NO:
H4476   61    Gly Arg Asn Tyr Gln Leu Gln Leu Thr Glu Ala          Gln Ala Ala Asn Gly Gly Ala
        62    GGC AGG AAC TAC CAG CTG CAA TTG ACT GAA GCA          CAA GCC GCT AAC GGT GGA GCG AG

M1080   193,63 ...  ...  ...  Ile *** Ala          ...  ...  ...    Gln Pro Gln Ala Thr Asn Gly Val Gln Gly
        64                AT. T..  GC.                                CAG CCC  ..A A..        .TG CAA G..

H355    65     ...  ...  ...  Phe  ...  ...  ...  ...  ...  ...  ...  Pro Pro Ser Lys Ser Gln Pro
        66                .T.                       ..G           ..C  C.G CCC TC. AAG AG. C.A CC.

6940    67     ...  Asn  ...  Ile  ...  ...  ...  ...  ...  ...  ...  Pro Pro Ser Lys Gly Gln Thr Gly
        68          .AC       ATT                                     C.A CCC TC. AAA .GT C.G ACG ..C 6557    69     ...  ...  ...  Tyr  ...  ...  ...  ...  ...  ...  ...  Gln Pro Ser Arg Thr Gln Gly Gln Thr
        70                                                            CA. CCC TC. AGA A.. C.A ..: CA. A..

870227  71     ...  ...  ...  Ile  ...  ...  ...  ...  ...  ...  ...  Pro Leu Pro Asn Ile Gln Pro Gln
        72                AT.                       ..G           ..C  C.G CTC .C.  AAT AT. C.A CC. CAG

B40     73     ...  ...  ...  Ile  ...  ...  ...  ...  ...  ...  ...  Pro Leu Pro Asn Ile Gln Pro Gln
        74                AT.                       ..G           ..C  C.G CTC .C.  AAT AT. C.A CC. CAG 40                              50
H4476   61    Gly Gln Val Lys Val Thr Lys Val Thr Lys Val Thr     Lys Ala Lys Ser Arg Ile Arg Thr Lys Ile Ser
        62    GGT CAG GTA AAA GTT ACT AAA GTT ACT                 AAG GCC AAA AGC CGC ATC AGG ACG AAA ATC AGT

M1080   63     Arg Gln Gly Asn Gln Val Thr                           Val                        Glu          ..C
        64     .G. CA. GGC AA. CAG GTA .C.                            .T.                        G..

H355    65                Gln Val                                     Ala                        Lys          ..
        66                CAG GTA                                                                 ...

6940    67                Asn                                                                                  ..
        68                 .A.                                                                    ...

6557    69     Asn Gln Val                                            Ala                        Lys          ..
        70     AA. CAG GTA                                                                       ...

870227  71                                                            Arg                        Lys          ..C
        72                                                            CG.                        ...

B40     73                                                            Arg                        Lys          ..C
        74                                                            CG.                        ...
```

FIG. 3A

| | SEQ ID NO: | | | | | | | | | | | 110 | | | | | | | | 120 | | |
|---|---|---|---|---|---|---|---|---|---|---|---|---|---|---|---|---|---|---|---|---|---|---|
| | | Thr | Leu | Arg | Ala | Gly | Arg | Val | Ala | Asn | Gln | Phe | Asp | Asp | Ala | Ser | Gln | Ala | Ile | Asp | Pro | Trp |
| H4476 | 75 | ACG | CTG | CGC | GCC | GGT | CGC | GTT | GCG | AAT | CAG | TTT | GAC | GAT | GCC | AGC | CAA | GCC | ATT | GAT | CCT | TGG |
| | 76 | . . . | . . . | . . . | . . . | . . . | . . . | . . . | . . . | . . . | . . . | . . . | . . . | . . . | . . . | . . . | . . . | . . . | . . . | . . . | . . . | . . . |
| | 77 | . . . | . . . | . . . | . . A | . . . | . . . | . . . | . . . | . . . | . . . | . . . | . . . | . . . | . . . | . . . | . . . | . . . | . . . | . . . | . . . | . . . |
| | | | | | Thr | | | | | | | | | | | | | | | | | |
| M1080 | 78 | . . . | . . . | . . . | . . . | . . . | . . . | . . . | . . C | . . . | . . . | . . . | . . . | . . . | . . . | . . . | . . . | . . . | . . . | . . . | . . . | . . . |
| H355 | 79 | . . . | . . . | . . . | . NN | . . . | NNN | . . . | . . . | . . . | . . . | . . . | . . . | . . . | . . . | . . . | . . . | . . . | . . . | . . . | . . . | . . . |
| | | | | | Thr | | | | | | | | | | | | | | | | | |
| | 80 | . . . | . . . | . . . | . . A | . . . | . . . | . . . | . . . | . . A | . . . | . . . | . . . | . . . | . . . | . . . | . . . | . . . | . . . | . . . | . . . | . . . |
| 870227 | 81 | . . . | . . . | . . . | . . . | . . . | . . . | . . . | . . . | . . . | . . . | . . . | . . . | . . . | . . . | . . . | . . . | . . . | . . . | . . . | . . . | . . . |
| | 82 | . . . | . . . | . . . | . . . | . . . | . . . | . . . | . . . | . . . | . . . | . . . | . . . | . . . | . . . | . . . | . . . | . . . | . . . | . . . | . . . | . . . |
| | | | | | Thr | | | | | | | | | | | | | | | | | |
| B40 | 83 | . . . | . . . | . . . | . . A | . . . | . . . | . . . | . . . | . . A | . . . | . . . | . . . | . . . | . . . | . . . | . . . | . . . | . . . | . . . | . . . | . . . |
| | 84 | . . . | . . . | . . . | . . . | . . . | . . . | . . . | . . . | . . . | . . . | . . . | . . . | . . . | . . . | . . . | . . . | . . . | . . . | . . . | . . . | . . . |

| | SEQ ID NO: | | | | | | | 130 | | | | | | | | 140 | | | | | | |
|---|---|---|---|---|---|---|---|---|---|---|---|---|---|---|---|---|---|---|---|---|---|---|
| | | Asp | Ser | Asn | Asn | Asp | Val | Ala | Ser | Gln | Leu | Gly | Ile | Phe | Lys | Arg | His | Asp | Asp | Met | Pro | Val |
| H4476 | 75 | GAC | AGC | AAT | AAT | GAT | GTG | GCT | TCG | CAA | TTG | GGT | ATT | TTC | AAA | CGC | CAC | GAC | GAC | ATG | CCG | GTT |
| | 76 | . . . | . . . | . . . | . . . | . . . | . . . | . . . | . . . | . . . | . . . | . . . | . . . | . . . | . . . | . . . | . . . | . . . | . . . | . . T | . . . | . . . |
| | | | | | | | | | | | | | | | | | | | | | Pro | |
| | 77 | . . . | . . . | . . . | . . . | . . . | . . . | . . . | . . . | . . . | . . . | . . . | . . . | . . . | . . . | . . . | . . . | . . . | . . . | . . . | . . . | . . . |
| M1080 | 78 | . . . | . . . | . . C | . . . | . . . | . . . | . . . | . . . | . . . | . . . | . . . | . . . | . . . | . . . | . . . | . . . | . . . | . . . | . . T | . . . | . . . |
| | | | | | | | | | | | | | | | | | | | | | Pro | |
| H355 | 79 | . . . | . . . | . . . | . . . | . . . | . . . | . . . | . . . | . . . | . . . | . . . | . . . | . . . | . . . | . . . | . . . | . . . | . . . | . . T | . . . | . . . |
| | | | | | | | | | | | | | | | | | | | | | Ser | |
| | 80 | . . . | . . . | . . . | . . . | . . . | . . . | . . . | . . . | . . . | . . . | . . . | . . . | . . . | . . . | . . . | . . . | . . . | . . . | . . T | . . . | . . . |
| | | | | | | | | | | | | | | | | | | | | | Ser | |
| 870227 | 81 | . . . | . . . | . . . | . . . | . . . | . . . | . . . | . . . | . . . | . . . | . . . | . . . | . . . | . . . | . . . | . . . | . . . | . . . | . . . | . . . | . . . |
| | 82 | . . . | . . . | . . . | . . . | . . . | . . . | . . . | . . . | . . . | . . . | . . . | . . . | . . . | . . . | . . . | . . . | . . . | . . . | . . T | . . . | . . . |
| B40 | 83 | . . . | . . . | . . . | . . . | . . . | . . . | . . . | . . . | . . . | . . . | . . . | . . . | . . . | . . . | . . . | . . . | . . . | . . . | . . . | . . . | . . . |
| | 84 | . . . | . . . | . . . | . . . | . . . | . . . | . . . | . . . | . . . | . . . | . . . | . . . | . . . | . . . | . . . | . . . | . . . | . . . | . . T | . . . | . . . |

| | SEQ ID NO: | | | | 150 | | | | | | | | 160 | | | | | | | | | |
|---|---|---|---|---|---|---|---|---|---|---|---|---|---|---|---|---|---|---|---|---|---|---|
| | | Ser | Val | Arg | Tyr | Asp | Ser | Pro | Glu | Phe | Ser | Gly | Phe | Ser | Gly | Ser | Val | Gln | Phe | Val | Pro | Ile |
| H4476 | 75 | TCT | GTA | CGC | TAC | GAT | TCC | CCC | GAA | TTT | TCC | GGT | TTC | AGC | GGC | AGC | GTT | CAA | TTC | GTT | CCG | ATC |
| | 76 | . . . | . . . | . . . | . . . | . . . | . . . | . . . | . . . | . . . | . . . | . . . | . . . | . . . | . . . | . . . | . . . | . . . | . . . | . . . | . . . | . . . |
| | | | | | | | | | | | | | | | | | | | | | | Ala |
| M1080 | 77 | . . . | . . . | . . . | . . . | . . C | . . T | . . G | . . C | . . . | . . . | . . . | . . . | . . . | . . . | . . . | . . C | . . . | . . . | . . . | . . . | GCT |
| | | | | | | | | Asp | | | | | | | | | | | | | | Ile |
| H355 | 78 | . . . | . . . | . . . | . . . | . . C | . . T | . . G | . . C | . . . | . . . | . . . | . . . | . . . | . . . | . . . | . . C | . . . | . . . | . . . | . . . | . . . |
| | | | | | | | | Asp | | | | | | | | | | | | | | |
| 6940 | 79 | . . . | . . . | . . . | . . . | . . . | . . . | . . . | . . . | . . . | . . . | . . . | . . . | . . . | . . . | . . . | . . . | . . . | . . . | . . . | . . . | Ala |
| | 80 | . . . | . . . | . . . | . . . | . . C | . . T | . . G | . . C | . . . | . . . | . . . | . . . | . . . | . . . | . . . | . . C | . . . | . . . | . . . | . . . | GC. |
| | | | | | | | | Asp | | | | | | | | | | | | | | Ala |
| 6557 | 85 | . . . | . . . | . . . | . . . | . . . | . . . | . . . | . . . | . . . | . . . | . . . | . . . | . . . | . . . | . . . | . . . | . . . | . . . | . . . | . . . | GCT |
| | 86 | . . . | . . . | . . . | . . . | . . . | . . . | . . . | . . . | . . . | . . . | . . . | . . . | . . . | . . . | . . . | . . . | . . . | . . . | . . . | . . . | Ala |
| | 87 | . . . | . . . | . . . | . . . | . . C | . . T | . . G | . . C | . . . | . . . | . . . | . . . | . . . | . . . | . . . | . . C | . . . | . . . | . . . | . . . | GC. |
| | | | | | | | | Asp | | | | | | | | | | | | | | Ala |
| 870227 | 88 | . . . | . . . | . . . | . . . | . . . | . . . | . . . | . . . | . . T | . . . | . . . | . . . | . . . | . . . | . . . | . . . | . . . | . . . | . . . | . . . | GC. |
| | 81 | . . . | . . . | . . . | . . . | . . . | . . . | . . . | Glu | . . . | . . . | . . . | . . . | . . . | . . . | . . . | . . . | . . . | . . . | . . . | . . . | . . . |
| | 82 | . . . | . . . | . . . | . . . | . . . | . . . | . . . | . . . | . . . | . . . | . . . | . . . | . . . | . . . | . . . | . . . | . . . | . . . | . . . | . . . | Ala |
| B40 | 83 | . . . | . . . | . . . | . . . | . . . | . . . | . . . | . . . | . . T | . . . | . . . | . . . | . . . | . . . | . . . | . . . | . . . | . . . | . . . | . . . | GC. |
| | 84 | . . . | . . . | . . . | . . . | . . . | . . . | . . . | . . . | . . . | . . . | . . . | . . . | . . . | . . . | . . . | . . . | . . . | . . . | . . . | . . . | . . . |

FIG. 3B

| SEQ ID NO: | | | | | | | | | | | 170 | | | | | | | | | | | 180 | | | | | | | |
|---|---|---|---|---|---|---|---|---|---|---|---|---|---|---|---|---|---|---|---|---|---|---|---|---|---|---|---|---|---|
| | | Gln | Asn | Ser | Lys | Ser | Ala | Tyr | Thr | Pro | Ala | Tyr | Tyr | Thr | Lys | Asp | Thr | Asn | Asn | Asn | Leu | Leu |
| H4476 | 75 | CAA | AAC | AGC | AAG | TCC | GCC | TAT | ACG | CCG | GCT | TAT | TAT | ACT | AAG | GAT | ACA | AAC | AAT | AAT | GTT | CTT |
| | 76 | | | | | | | | Thr | | | Tyr | Val | Ala | Glu | | | Gly | Val | Ala | Lys | Lys |
| | 77 | | | | | | | | | | | | | | | | | | | | | |
| M1080 | 78 | | | | | | | | Thr | | | : GTG | G.G | GT. | . A | . AT | GG. | . AT | GC. | GTA | GC. | AAA |
| | 79 | | | | | | | | | | | | His | Asn | Thr | Arg | Gln | Asn | Ala | Asp | Val | Phe |
| H355 | 80 | | | | | | | | Thr | | | C. . | A. . | . G. | C.G | .AC | . T | GC. | G. . | G. . | G. . | TTC |
| | 85 | | | .A | | | | | | | | Thr | Tyr | Thr | Val | Asp | Ser | Ser | Gly | Val | Val | |
| 6940 | 86 | | | | | | | | | | | AC. | . | GT. | . . . | GT. | .GT | GG. | GT. | G. . | | |
| | 87 | | | | | | | Lys | | | | Tyr | Val | Asp | Glu | Lys | Lys | Met | Val | His | | |
| 6557 | 88 | | | | | | | .A | | | | . . . | GTG | GA. | G. . | A.G | .A. | .TG | GT. | C. . | | |
| 870227 | 81 | | | | | | | Thr | | | | His | Phe | Val | Gln | Asn | Lys | Gln | Asn | Gln | Arg | Pro |
| | 82 | | | | | | | | | | | C. . | .T. | GT. | C. . | A. . | .AG | C.A | . . . | C.G | .GG | CCT |
| | 83 | | | | | | | Thr | | | | His | Phe | Val | Gln | Asn | Lys | Gln | Asn | Gln | Arg | Pro |
| B40 | 84 | | | | | | | | | | | C. . | .T. | GT. | C. . | A. . | .AG | C.A | . . . | C.G | .GG | CCT |

| | | | | | | | | | | | 190 | | | | | | | | | | | 200 | | | | | | | |
|---|---|---|---|---|---|---|---|---|---|---|---|---|---|---|---|---|---|---|---|---|---|---|---|---|---|---|---|---|---|
| | | Thr | Leu | Val | Pro | Ala | Val | Val | Gly | Lys | Pro | Gly | Ser | Asp | Val | Tyr | Tyr | Ala | Gly | Leu | Asn | Tyr |
| H4476 | 75 | ACT | CTC | GTT | CCG | GCT | GTT | GTC | GGC | AAG | CCC | GGA | TCG | GAT | GTG | TAT | TAT | GCC | GGT | CTG | AAT | TAC |
| | 76 | | | | Ala | | | | | | | | | | | | | | | | | |
| | 77 | | | | G. . | | | | | | | | | | | | | | | | | |
| M1080 | 78 | | | | Pro | | | | | | | | | | | | | | | | | |
| | 79 | | | | | | | | | | | | | | | | | | | | | |
| H355 | 80 | | Pro | | . . . | | | | | | | | | | | | | | | | | |
| | 85 | | . C . | | Pro | | | | | | | | | | | | | | | | | |
| 6940 | 86 | | | | . T | | | | | | | | | | | | | | | | | |
| | 87 | | | | Ala | | | | | | | | | | | | | | | | | |
| 6557 | 88 | | | | G. . | | | | | | | | | | | | | | | | | |
| 870227 | 81 | | | | Pro | | | | | | | | | | | | | | | | | T |
| | 82 | | | | | | | | | | | . G | | | | | | | | | | |
| | 83 | | | | Pro | | | | | | | | | | | | | | | | | |
| B40 | 84 | | | | | | | | | | | . G | | | | | | | | | | |

FIG. 3C

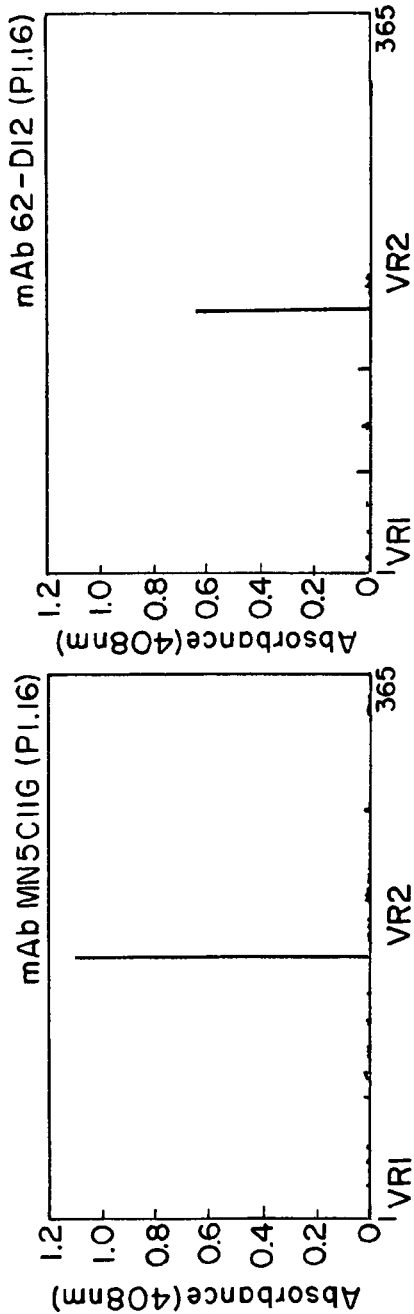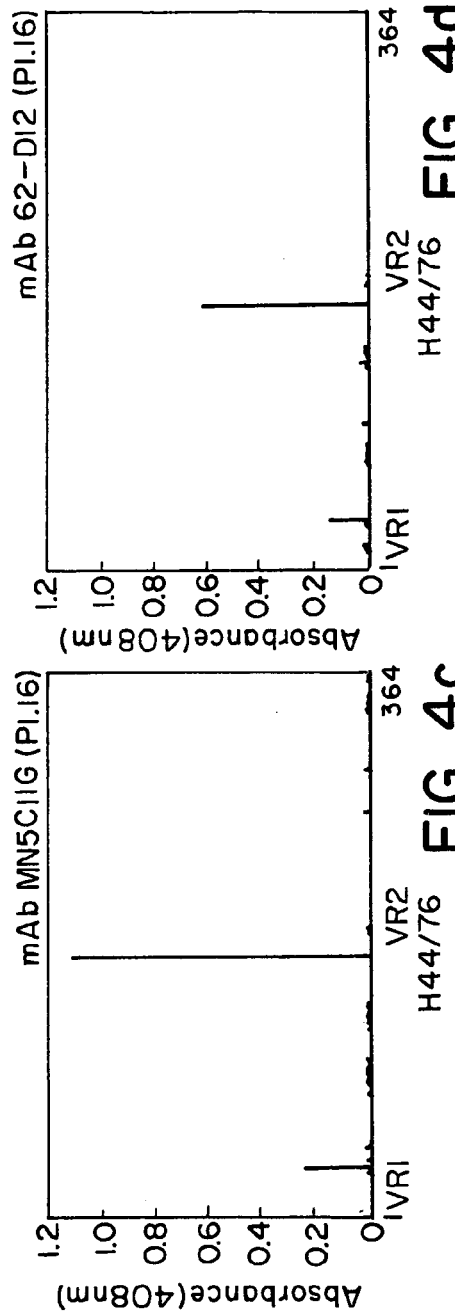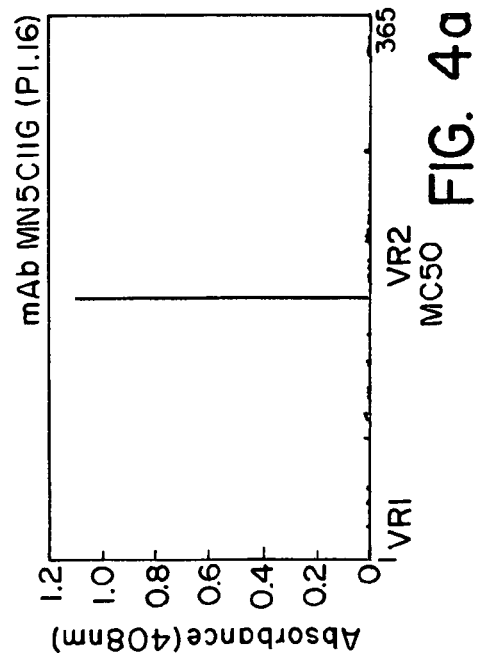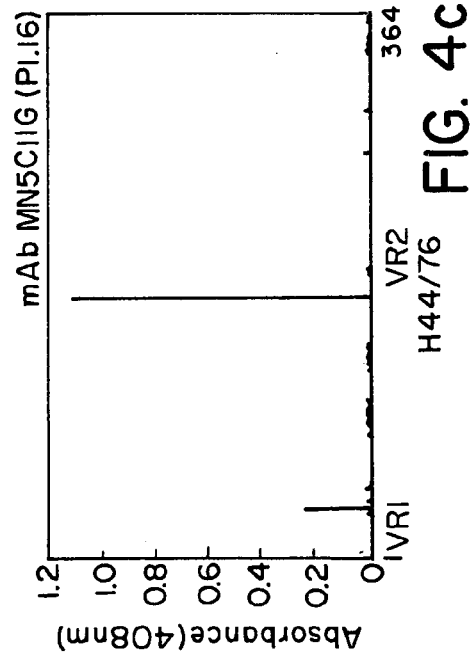

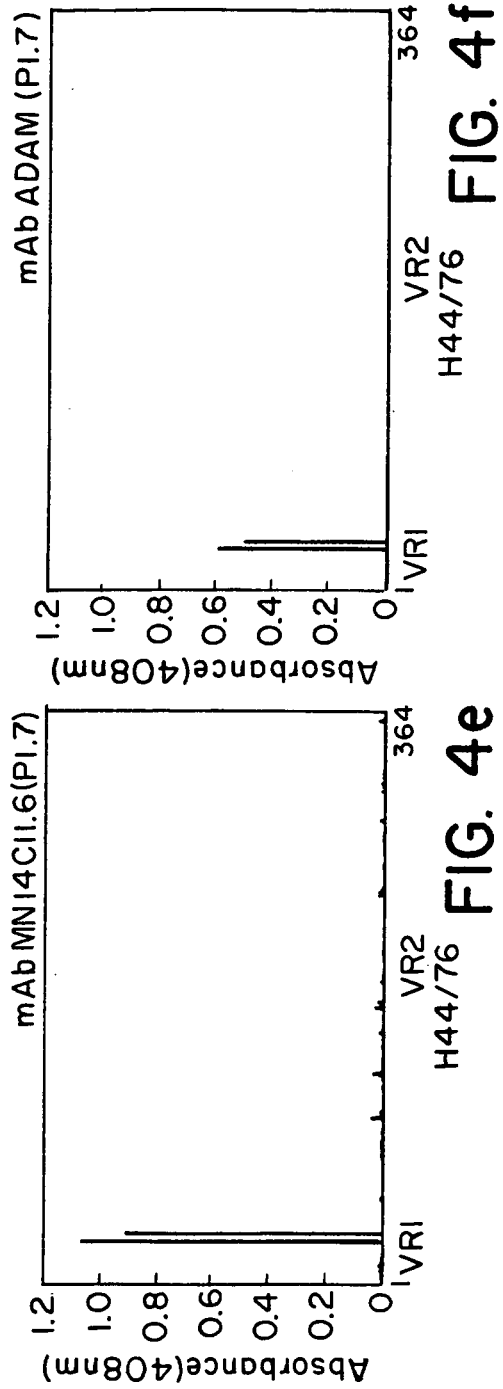
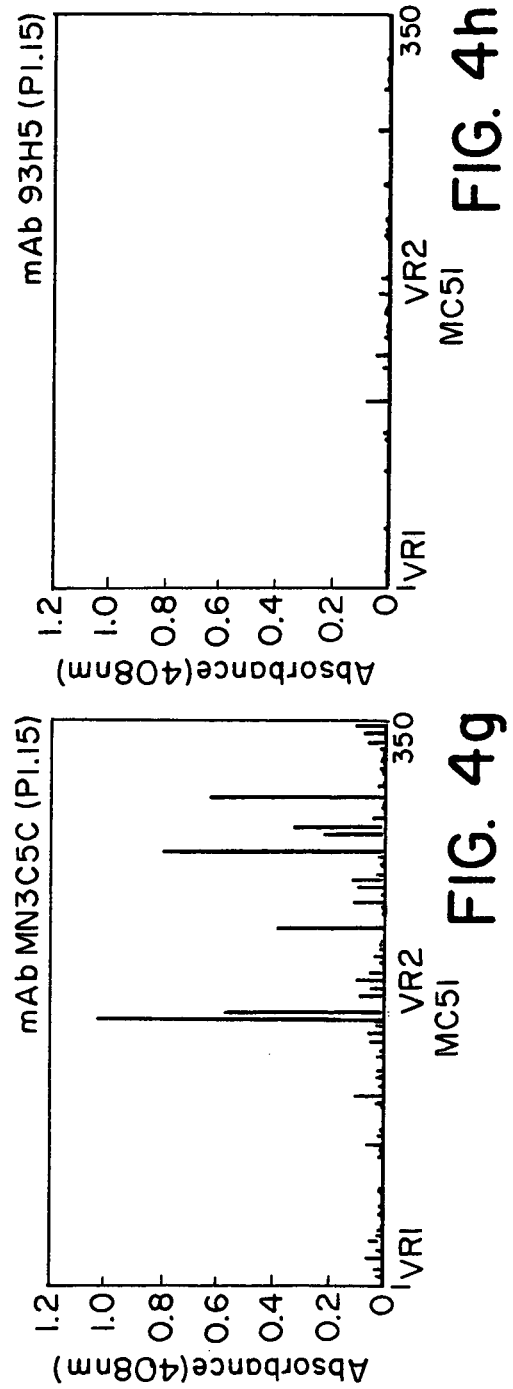

FIG. 7 HYBRID N. MENINGIDITIS FLAGELLIN STRUCTURES

FIG. 8. A representative HPLC of purified pCB12-10-6 showing a single major peak A representative SDS-Page of pCB12-10-6.

| Lane# | Sample |
|---|---|
| 1 | Blank |
| 2 | High Molecular Weight Standard |
| 3 | Dialyzed pCB12-10-6, Step 2 |
| 4 | Fractions off peak pCB12-10-6 |
| 5 | Purified pCB12-10-6 from HPLC,dialyzed in PBS, 20 μg |
| 6 | Purified pCB12-10-6 from HPLC,dialyzed in PBS, 1 μg |
| 7 | LPS - 5828 |
| 8 | Blank |
| 9 | High Molecular Weight Standard |
| 10 | Blank |

Photographs of representative western blot analysis of CB1 and CB2 CRM197 conjugates.

| Lane # | Sample |
|---|---|
| 1 | Molecular Weight Standard |
| 2 | M20-CRM, 10 μg |
| 3 | M20-CRM, 20 μg |
| 4 | Molecular Weight Standard |
| 5 | M21-CRM, 1 μg |

PUTATIVE CONFORMATION MENINGOCOCCAL CLASS I OUTER-MEMBRANE PROTEIN PL.16

(SEQ ID NO:5)

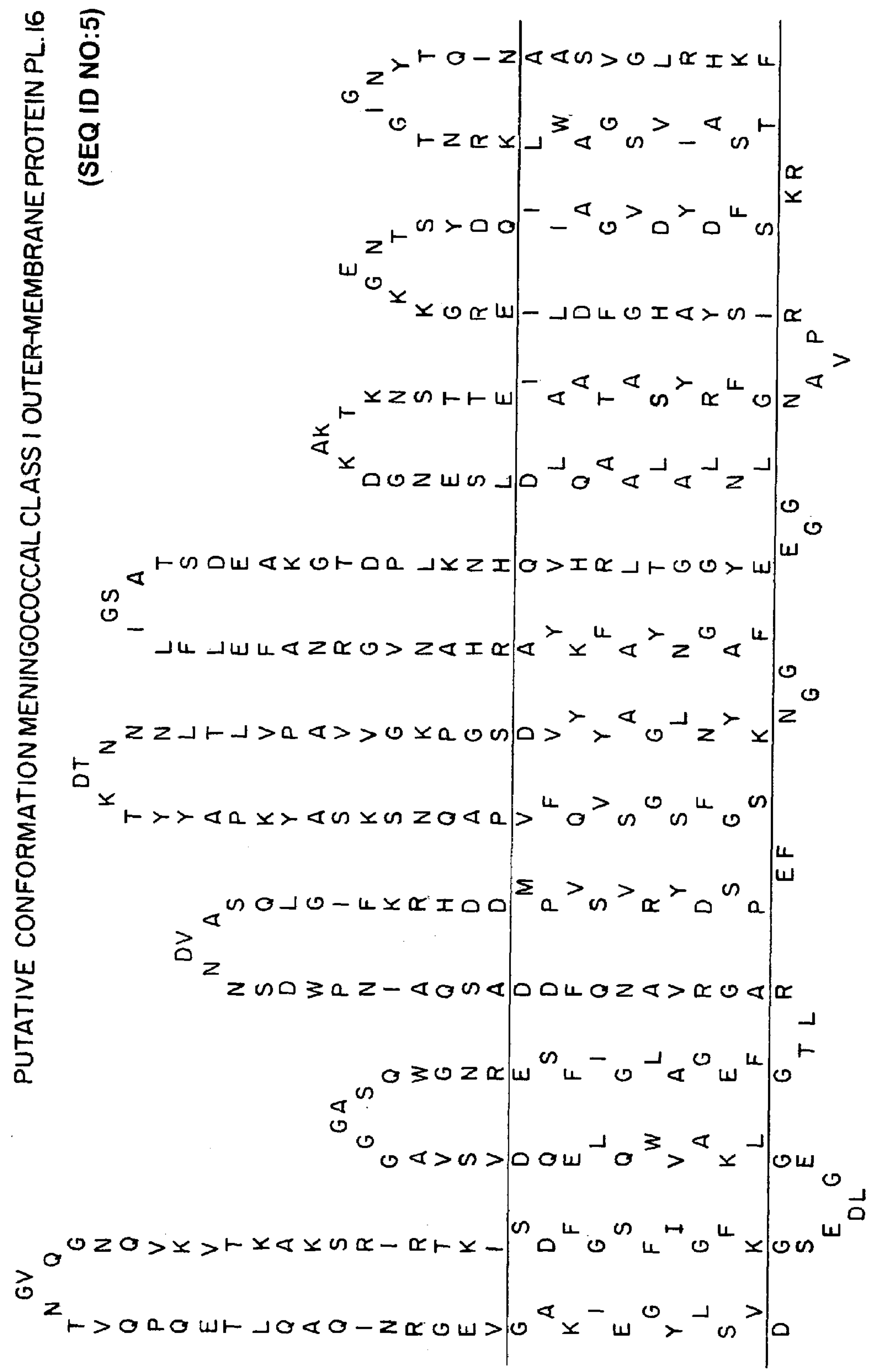

FIG. 11

SEQUENCE LISTING

<160> NUMBER OF SEQ ID NOS: 193

<210> SEQ ID NO 1
<211> LENGTH: 30
<212> TYPE: PRT
<213> ORGANISM: Neisseria meningitidis

```
<220> FEATURE:
<221> NAME/KEY: VARIANT
<222> LOCATION: 26
<223> OTHER INFORMATION: Xaa = Any Amino Acid

<400> SEQUENCE: 1

Asp Val Ser Leu Tyr Gly Glu Ile Lys Ala Gly Val Glu Asp Arg Asn
 1               5                  10                  15

Tyr Gln Leu Gln Leu Thr Glu Ala Gln Xaa Ala Ala Gly Asn
            20                  25                  30

<210> SEQ ID NO 2
<211> LENGTH: 42
<212> TYPE: PRT
<213> ORGANISM: Neisseria meningitidis
<220> FEATURE:
<221> NAME/KEY: VARIANT
<222> LOCATION: 24
<223> OTHER INFORMATION: Xaa = Any Amino Acid

<400> SEQUENCE: 2

Pro Val Ser Val Arg Tyr Asp Ser Pro Glu Phe Ser Gly Phe Ser Gly
 1               5                  10                  15

Ser Val Gln Phe Val Pro Ile Xaa Asn Ser Lys Ser Ala Tyr Thr Pro
            20                  25                  30

Ala Tyr Tyr Thr Lys Asp Thr Asn Asn Asn
            35                  40

<210> SEQ ID NO 3
<211> LENGTH: 30
<212> TYPE: PRT
<213> ORGANISM: Neisseria meningitidis

<400> SEQUENCE: 3

Phe Ser Gly Phe Ser Gly Ser Val Gln Phe Val Pro Ile Gln Asn Ser
 1               5                  10                  15

Lys Ser Ala Tyr Thr Pro Ala Tyr Tyr Thr Lys Asp Thr Asn
            20                  25                  30

<210> SEQ ID NO 4
<211> LENGTH: 37
<212> TYPE: PRT
<213> ORGANISM: Neisseria meningitidis

<400> SEQUENCE: 4

Pro Val Ser Val Arg Tyr Asp Ser Pro Glu Phe Ser Gly Phe Ser Gly
 1               5                  10                  15

Ser Val Gln Phe Val Pro Ile Gln Asn Ser Lys Ser Ala Tyr Thr Pro
            20                  25                  30

Ala Tyr Tyr Thr Lys
            35

<210> SEQ ID NO 5
<211> LENGTH: 374
<212> TYPE: PRT
<213> ORGANISM: Neisseria meningitidis

<400> SEQUENCE: 5

Asp Val Ser Leu Tyr Gly Glu Ile Lys Ala Gly Val Glu Gly Arg Asn
 1               5                  10                  15

Ile Gln Ala Gln Leu Thr Glu Gln Pro Gln Val Thr Asn Gly Val Gln
            20                  25                  30
```

Gly Asn Gln Val Lys Val Thr Lys Ala Lys Ser Arg Ile Arg Thr Lys
            35                  40                  45

Ile Ser Asp Phe Gly Ser Phe Ile Gly Phe Lys Gly Ser Glu Asp Leu
    50                  55                  60

Gly Glu Gly Leu Lys Ala Val Trp Gln Leu Glu Gln Asp Val Ser Val
65                  70                  75                  80

Ala Gly Gly Gly Ala Ser Gln Trp Gly Asn Arg Glu Ser Phe Ile Gly
                85                  90                  95

Leu Ala Gly Glu Phe Gly Thr Leu Arg Ala Gly Arg Val Ala Asn Gln
            100                 105                 110

Phe Asp Asp Ala Ser Gln Ala Ile Asn Pro Trp Asp Ser Asn Asn Asp
            115                 120                 125

Val Ala Ser Gln Leu Gly Ile Phe Lys Arg His Asp Asp Met Pro Val
            130                 135                 140

Ser Val Arg Tyr Asp Ser Pro Glu Phe Ser Gly Phe Ser Gly Ser Val
145                 150                 155                 160

Gln Phe Val Pro Ala Gln Asn Ser Lys Ser Ala Tyr Lys Pro Ala Tyr
                165                 170                 175

Tyr Thr Lys Asp Thr Asn Asn Asn Leu Thr Leu Val Pro Ala Val Val
            180                 185                 190

Gly Lys Pro Gly Ser Asp Val Tyr Tyr Ala Gly Leu Asn Tyr Lys Asn
            195                 200                 205

Gly Gly Phe Ala Gly Asn Tyr Ala Phe Lys Tyr Ala Arg His Ala Asn
            210                 215                 220

Val Gly Arg Asn Ala Phe Glu Leu Phe Leu Ile Gly Ser Ala Thr Ser
225                 230                 235                 240

Asp Glu Ala Lys Gly Thr Asp Pro Leu Lys Asn His Gln Val His Arg
                245                 250                 255

Leu Thr Gly Gly Tyr Glu Glu Gly Leu Asn Leu Ala Leu Ala Ala
            260                 265                 270

Gln Leu Asp Leu Ser Glu Asn Gly Asp Lys Ala Lys Thr Lys Asn Ser
            275                 280                 285

Thr Thr Glu Ile Ala Ala Thr Ala Ser Tyr Arg Phe Gly Asn Ala Val
            290                 295                 300

Pro Arg Ile Ser Tyr Ala His Gly Phe Asp Leu Ile Glu Arg Gly Lys
305                 310                 315                 320

Lys Gly Glu Asn Thr Ser Tyr Asp Gln Ile Ile Ala Gly Val Asp Tyr
                325                 330                 335

Asp Phe Ser Lys Arg Thr Ser Ala Ile Val Ser Gly Ala Trp Leu Lys
            340                 345                 350

Arg Asn Thr Gly Ile Gly Asn Tyr Thr Gln Ile Asn Ala Ala Ser Val
            355                 360                 365

Gly Leu Arg His Lys Phe
    370

<210> SEQ ID NO 6
<211> LENGTH: 368
<212> TYPE: PRT
<213> ORGANISM: Neisseria meningitidis

<400> SEQUENCE: 6

Asp Val Ser Leu Tyr Gly Glu Ile Lys Ala Gly Val Glu Gly Arg Asn
1               5                   10                  15

Phe Gln Leu Gln Leu Thr Glu Pro Pro Ser Lys Ser Gln Pro Gln Val
            20                  25                  30

Lys Val Thr Lys Ala Lys Ser Arg Ile Arg Thr Lys Ile Ser Asp Phe
            35                  40                  45

Gly Ser Phe Ile Gly Phe Lys Gly Ser Glu Asp Leu Gly Glu Gly Leu
 50                  55                  60

Lys Ala Val Trp Gln Leu Glu Gln Asp Val Ser Val Ala Gly Gly Gly
 65                  70                  75                  80

Ala Thr Gln Trp Gly Asn Arg Glu Ser Phe Val Gly Leu Ala Gly Glu
                85                  90                  95

Phe Gly Thr Leu Arg Ala Gly Arg Val Ala Asn Gln Phe Asp Asp Ala
            100                 105                 110

Ser Gln Ala Ile Asp Pro Trp Asp Ser Asn Asn Asp Val Ala Ser Gln
            115                 120                 125

Leu Gly Ile Phe Lys Arg His Asp Asp Met Pro Val Ser Val Arg Tyr
            130                 135                 140

Asp Ser Pro Asp Phe Ser Gly Phe Ser Gly Ser Val Gln Phe Val Pro
145                 150                 155                 160

Ile Gln Asn Ser Lys Ser Ala Tyr Thr Pro Ala His Tyr Thr Arg Gln
                165                 170                 175

Asn Asn Thr Asp Val Phe Val Pro Ala Val Val Gly Lys Pro Gly Ser
            180                 185                 190

Asp Val Tyr Tyr Ala Gly Leu Asn Tyr Lys Asn Gly Gly Phe Ala Gly
            195                 200                 205

Ser Tyr Ala Phe Lys Tyr Ala Arg His Ala Asn Val Gly Arg Asp Ala
            210                 215                 220

Phe Glu Leu Phe Leu Leu Gly Ser Thr Ser Asp Glu Ala Lys Gly Thr
225                 230                 235                 240

Asp Pro Leu Lys Asn His Gln Val His Arg Leu Thr Gly Gly Tyr Glu
                245                 250                 255

Glu Gly Gly Leu Asn Leu Ala Leu Ala Ala Gln Leu Asp Leu Ser Glu
            260                 265                 270

Asn Gly Asp Lys Ala Lys Thr Lys Asn Ser Thr Thr Glu Ile Ala Ala
            275                 280                 285

Thr Ala Ser Tyr Arg Phe Gly Asn Ala Val Pro Arg Ile Ser Tyr Ala
            290                 295                 300

His Gly Phe Asp Leu Ile Glu Arg Gly Lys Lys Gly Glu Asn Thr Ser
305                 310                 315                 320

Tyr Asp Gln Ile Ile Ala Gly Val Asp Tyr Asp Phe Ser Lys Arg Thr
                325                 330                 335

Ser Ala Ile Val Ser Gly Ala Trp Leu Lys Arg Asn Thr Gly Ile Gly
            340                 345                 350

Asn Tyr Thr Gln Ile Asn Ala Ala Ser Val Gly Leu Arg His Lys Phe
            355                 360                 365

<210> SEQ ID NO 7
<211> LENGTH: 373
<212> TYPE: PRT
<213> ORGANISM: Neisseria meningitidis

<400> SEQUENCE: 7

Asp Val Ser Leu Tyr Gly Glu Ile Lys Ala Gly Val Glu Gly Arg Asn
  1               5                  10                  15

Tyr Gln Leu Gln Leu Thr Glu Ala Gln Ala Ala Asn Gly Gly Ala Ser
                 20                  25                  30

Gly Gln Val Lys Val Thr Lys Val Thr Lys Ala Lys Ser Arg Ile Arg

```
                35                  40                  45
Thr Lys Ile Ser Asp Phe Gly Ser Phe Ile Gly Phe Lys Gly Ser Glu
 50                  55                  60

Asp Leu Gly Asp Gly Leu Lys Ala Val Trp Gln Leu Glu Gln Asp Val
 65                  70                  75                  80

Ser Val Ala Gly Gly Ala Thr Gln Trp Gly Asn Arg Glu Ser Phe
                 85                  90                  95

Ile Gly Leu Ala Gly Glu Phe Gly Thr Leu Arg Ala Gly Arg Val Ala
                100                 105                 110

Asn Gln Phe Asp Asp Ala Ser Gln Ala Ile Asp Pro Trp Asp Ser Asn
                115                 120                 125

Asn Asp Val Ala Ser Gln Leu Gly Ile Phe Lys Arg His Asp Asp Met
130                 135                 140

Pro Val Ser Val Arg Tyr Asp Ser Pro Glu Phe Ser Gly Phe Ser Gly
145                 150                 155                 160

Ser Val Gln Phe Val Pro Ile Gln Asn Ser Lys Ser Ala Tyr Thr Pro
                165                 170                 175

Ala Tyr Tyr Thr Lys Asn Thr Asn Asn Leu Thr Leu Val Pro Ala
                180                 185                 190

Val Val Gly Lys Pro Gly Ser Asp Val Tyr Tyr Ala Gly Leu Asn Tyr
                195                 200                 205

Lys Asn Gly Gly Phe Ala Gly Asn Tyr Ala Phe Lys Tyr Ala Arg His
210                 215                 220

Ala Asn Val Gly Arg Asn Ala Phe Glu Leu Phe Leu Ile Gly Ser Gly
225                 230                 235                 240

Ser Asp Gln Ala Lys Gly Thr Asp Pro Leu Lys Asn His Gln Val His
                245                 250                 255

Arg Leu Thr Gly Gly Tyr Glu Gly Gly Leu Asn Leu Ala Leu Ala
                260                 265                 270

Ala Gln Leu Asp Leu Ser Glu Asn Gly Asp Lys Thr Lys Asn Ser Thr
                275                 280                 285

Thr Glu Ile Ala Ala Thr Ala Ser Tyr Arg Phe Gly Asn Ala Val Pro
290                 295                 300

Arg Ile Ser Tyr Ala His Gly Phe Asp Phe Ile Glu Arg Gly Lys Lys
305                 310                 315                 320

Gly Glu Asn Thr Ser Tyr Asp Gln Ile Ile Ala Gly Val Asp Tyr Asp
                325                 330                 335

Phe Ser Lys Arg Thr Ser Ala Ile Val Ser Gly Ala Trp Leu Lys Arg
                340                 345                 350

Asn Thr Gly Ile Gly Asn Tyr Thr Gln Ile Asn Ala Ala Ser Val Gly
                355                 360                 365

Leu Arg His Lys Phe
    370

<210> SEQ ID NO 8
<211> LENGTH: 367
<212> TYPE: PRT
<213> ORGANISM: Neisseria meningitidis

<400> SEQUENCE: 8

Asp Val Ser Leu Tyr Gly Glu Ile Lys Ala Gly Val Glu Gly Arg Asn
 1               5                  10                  15

Ile Gln Leu Gln Leu Thr Glu Pro Leu Gln Asn Ile Gln Gln Pro Gln
                 20                  25                  30
```

-continued

```
Val Thr Lys Ala Lys Ser Arg Ile Arg Thr Lys Ile Ser Asp Phe Gly
         35                  40                  45
Ser Phe Ile Gly Phe Lys Gly Ser Glu Asp Leu Gly Glu Gly Leu Lys
     50                  55                  60
Ala Val Trp Gln Leu Glu Gln Asp Val Ser Val Ala Gly Gly Gly Ala
 65                  70                  75                  80
Thr Arg Trp Gly Asn Arg Glu Ser Phe Val Gly Leu Ala Gly Glu Phe
                 85                  90                  95
Gly Thr Leu Arg Ala Gly Arg Val Ala Asn Gln Phe Asp Asp Ala Ser
            100                 105                 110
Lys Ala Ile Asp Pro Trp Asp Ser Asn Val Val Ala Ser Gln Leu
            115                 120                 125
Gly Ile Phe Lys Arg Met Asp Asp Met Pro Val Ser Val Arg Tyr Asp
        130                 135                 140
Ser Pro Glu Phe Ser Gly Phe Ser Gly Ser Val Gln Phe Val Pro Ala
145                 150                 155                 160
Gln Asn Ser Lys Ser Ala Tyr Thr Pro Ala His Phe Val Gln Gln Thr
                165                 170                 175
Pro Gln Gln Pro Thr Leu Val Pro Ser Ala Val Val Gly Lys Pro Gly
            180                 185                 190
Ser Asp Val Tyr Tyr Ala Gly Leu Asn Tyr Lys Asn Gly Phe Ala
        195                 200                 205
Gly Asn Tyr Ala Phe Lys Tyr Ala Lys His Ala Asn Val Gly Arg Asp
    210                 215                 220
Ala Phe Glu Leu Phe Leu Leu Gly Ser Gly Ser Asp Glu Ala Lys Gly
225                 230                 235                 240
Thr Asp Pro Leu Lys Asn His Gln Val His Arg Leu Thr Gly Gly Tyr
                245                 250                 255
Glu Glu Gly Gly Leu Asn Leu Ala Leu Ala Ala Gln Leu Asp Leu Ser
            260                 265                 270
Glu Asn Ala Asp Lys Thr Lys Asn Ser Thr Thr Glu Ile Ala Ala Thr
        275                 280                 285
Ala Ser Tyr Arg Phe Gly Asn Ala Val Pro Arg Ile Ser Tyr Ala His
290                 295                 300
Gly Phe Asp Phe Ile Glu Arg Gly Lys Lys Gly Glu Asn Thr Ser Tyr
305                 310                 315                 320
Asp Gln Ile Ile Ala Gly Val Asp Tyr Asp Phe Ser Lys Arg Thr Ser
                325                 330                 335
Ala Ile Val Ser Gly Ala Trp Leu Lys Arg Asn Thr Gly Ile Gly Asn
            340                 345                 350
Tyr Thr Gln Ile Asn Ala Ala Ser Val Gly Leu Arg His Lys Phe
        355                 360                 365

<210> SEQ ID NO 9
<211> LENGTH: 41
<212> TYPE: DNA
<213> ORGANISM: Artificial Sequence
<220> FEATURE:
<223> OTHER INFORMATION: PCR primer

<400> SEQUENCE: 9
tgtaaaacga cggccagttt gaagacgtat cgggrgtttg c        41

<210> SEQ ID NO 10
<211> LENGTH: 42
<212> TYPE: DNA
```

-continued

<213> ORGANISM: Artificial Sequence
<220> FEATURE:
<223> OTHER INFORMATION: PCR primer

<400> SEQUENCE: 10
tgtaaaacga cggccagtgg cgaattcggt acgctgcgcg cc         42

<210> SEQ ID NO 11
<211> LENGTH: 42
<212> TYPE: DNA
<213> ORGANISM: Artificial Sequence
<220> FEATURE:
<223> OTHER INFORMATION: PCR primer

<400> SEQUENCE: 11
tgtaaaacga cggccagtca tcaggtacac cgcctgacgg gc         42

<210> SEQ ID NO 12
<211> LENGTH: 40
<212> TYPE: DNA
<213> ORGANISM: Artificial Sequence
<220> FEATURE:
<223> OTHER INFORMATION: PCR primer

<400> SEQUENCE: 12
tgtaaaacga cggccagtgc agattggcag tcagattgca            40

<210> SEQ ID NO 13
<211> LENGTH: 40
<212> TYPE: DNA
<213> ORGANISM: Artificial Sequence
<220> FEATURE:
<223> OTHER INFORMATION: PCR primer

<400> SEQUENCE: 13
tgtaaaacga cggccagtgg gatcggtacc tttggcttga            40

<210> SEQ ID NO 14
<211> LENGTH: 40
<212> TYPE: DNA
<213> ORGANISM: Artificial Sequence
<220> FEATURE:
<223> OTHER INFORMATION: PCR primer

<400> SEQUENCE: 14
tgtaaaacga cggccagtaa ctgattcgca acgcgaccgg            40

<210> SEQ ID NO 15
<211> LENGTH: 24
<212> TYPE: DNA
<213> ORGANISM: Artificial Sequence
<220> FEATURE:
<223> OTHER INFORMATION: PCR primer

<400> SEQUENCE: 15
ttgaaggacg tatcgggtgt ttcg                             24

<210> SEQ ID NO 16
<211> LENGTH: 23
<212> TYPE: DNA
<213> ORGANISM: Artificial Sequence
<220> FEATURE:
<223> OTHER INFORMATION: PCR primer

<400> SEQUENCE: 16
gcagattggc agtcagattg ctt                              23

<210> SEQ ID NO 17
<211> LENGTH: 10
<212> TYPE: PRT
<213> ORGANISM: Neisseria meningitidis

<400> SEQUENCE: 17

Tyr Tyr Thr Lys Asp Thr Asn Asn Asn Leu
1               5                   10

<210> SEQ ID NO 18
<211> LENGTH: 10
<212> TYPE: PRT
<213> ORGANISM: Neisseria meningitidis

<400> SEQUENCE: 18

Tyr Tyr Thr Lys Asn Thr Asn Asn Asn Leu
1               5                   10

<210> SEQ ID NO 19
<211> LENGTH: 11
<212> TYPE: PRT
<213> ORGANISM: Neisseria meningitidis

<400> SEQUENCE: 19

His Tyr Thr Arg Gln Asn Asn Thr Asp Val Phe
1               5                   10

<210> SEQ ID NO 20
<211> LENGTH: 10
<212> TYPE: PRT
<213> ORGANISM: Neisseria meningitidis

<400> SEQUENCE: 20

Ala Gln Ala Ala Asn Gly Gly Ala Ser Gly
1               5                   10

<210> SEQ ID NO 21
<211> LENGTH: 11
<212> TYPE: PRT
<213> ORGANISM: Neisseria meningitidis

<400> SEQUENCE: 21

His Phe Val Gln Gln Thr Pro Gln Ser Gln Pro
1               5                   10

<210> SEQ ID NO 22
<211> LENGTH: 11
<212> TYPE: PRT
<213> ORGANISM: Neisseria meningitidis

<400> SEQUENCE: 22

Gln Pro Gln Val Thr Asn Gly Val Gln Gly Asn
1               5                   10

<210> SEQ ID NO 23
<211> LENGTH: 7
<212> TYPE: PRT
<213> ORGANISM: Neisseria meningitidis

<400> SEQUENCE: 23

Pro Pro Ser Lys Ser Gln Pro
1               5

```
<210> SEQ ID NO 24
<211> LENGTH: 13
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 24

Xaa Gly Gly Tyr Tyr Thr Lys Asp Thr Asn Asn Asn Leu
 1               5                  10

<210> SEQ ID NO 25
<211> LENGTH: 13
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 25

Xaa Gly Gly Ala Gln Ala Ala Asn Gly Gly Ala Ser Gly
 1               5                  10

<210> SEQ ID NO 26
<211> LENGTH: 19
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 26

Xaa Gly Gly Leu Ser Glu Asn Gly Asp Lys Ala Lys Thr Lys Asn Ser
 1               5                  10                  15

Thr Thr Glu

<210> SEQ ID NO 27
<211> LENGTH: 21
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 27

Xaa Gly Gly Asn Ala Phe Glu Leu Phe Leu Ile Gly Ser Ala Thr Ser
 1               5                  10                  15

Asp Glu Ala Lys Gly
                20

<210> SEQ ID NO 28
<211> LENGTH: 24
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 28

Xaa Ala Asn Val Gly Arg Asn Ala Phe Glu Leu Phe Leu Ile Gly Ser
 1               5                  10                  15
```

Ala Thr Ser Asp Glu Ala Lys Gly
            20

<210> SEQ ID NO 29
<211> LENGTH: 17
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 29

Xaa Gly Gly Asp Ser Asn Asn Asp Val Ala Ser Gln Leu Gln Ile Phe
1               5                   10                  15

Lys

<210> SEQ ID NO 30
<211> LENGTH: 21
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 30

Xaa Ala Asp Leu Asn Thr Asp Ala Glu Arg Val Ala Val Asn Thr Ala
1               5                   10                  15

Asn Ala His Pro Val
            20

<210> SEQ ID NO 31
<211> LENGTH: 14
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 31

Xaa Gly Gly Gly Lys Lys Gly Glu Asn Thr Ser Tyr Asp Gln
1               5                   10

<210> SEQ ID NO 32
<211> LENGTH: 16
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 32

Xaa Gly Gly Glu Arg Gly Lys Lys Gly Glu Asn Thr Ser Tyr Asp Gln
1               5                   10                  15

<210> SEQ ID NO 33
<211> LENGTH: 22
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 33

Xaa Gly Gly Val Lys Asp Ala Gly Thr Tyr Lys Ala Gln Gly Gly Lys
 1               5                   10                  15

Ser Lys Thr Ala Thr Gln
            20

<210> SEQ ID NO 34
<211> LENGTH: 16
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 34

Xaa Gly Gly Trp Ser Val Ala Glu Gly Gly Ala Ser Gln Val Gly Asn
 1               5                   10                  15

<210> SEQ ID NO 35
<211> LENGTH: 16
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 35

Xaa Lys Arg Asn Thr Gly Ile Gly Asn Tyr Thr Gln Ile Asn Ala Ala
 1               5                   10                  15

<210> SEQ ID NO 36
<211> LENGTH: 22
<212> TYPE: PRT
<213> ORGANISM: Neisseria meningitidis
<220> FEATURE:
<221> NAME/KEY: VARIANT
<222> LOCATION: 1
<223> OTHER INFORMATION: Xaa = Any Amino Acid

<400> SEQUENCE: 36

Xaa Gly Gly Asn Ile Gln Ala Gln Leu Thr Glu Gln Pro Gln Val Thr
 1               5                   10                  15

Asn Gly Val Gln Gly Asn
            20

<210> SEQ ID NO 37
<211> LENGTH: 15
<212> TYPE: DNA
<213> ORGANISM: Artificial Sequence
<220> FEATURE:
<223> OTHER INFORMATION: linker insertion

<400> SEQUENCE: 37
atgatcgatg gattc                                                    15

<210> SEQ ID NO 38
<211> LENGTH: 21
<212> TYPE: DNA
<213> ORGANISM: Artificial Sequence
<220> FEATURE:
<223> OTHER INFORMATION: linker insertion

<400> SEQUENCE: 38
gatatcatcg atggattcat c                                             21

```
<210> SEQ ID NO 39
<211> LENGTH: 18
<212> TYPE: PRT
<213> ORGANISM: Neisseria meningitidis

<400> SEQUENCE: 39

Tyr Tyr Thr Lys Asp Thr Asn Asn Asn Leu Thr Leu Val Pro Ala Gly
 1               5                  10                  15

Ala Cys

<210> SEQ ID NO 40
<211> LENGTH: 17
<212> TYPE: PRT
<213> ORGANISM: Neisseria meningitidis

<400> SEQUENCE: 40

Ala Gln Ala Ala Asn Gly Gly Ala Ser Gly Gln Val Lys Ala Gly Ala
 1               5                  10                  15

Cys

<210> SEQ ID NO 41
<211> LENGTH: 19
<212> TYPE: PRT
<213> ORGANISM: Neisseria meningitidis

<400> SEQUENCE: 41

Asn Ile Gln Ala Gln Leu Thr Glu Gln Pro Gln Val Thr Asn Gly Val
 1               5                  10                  15

Gln Gly Asn

<210> SEQ ID NO 42
<211> LENGTH: 13
<212> TYPE: PRT
<213> ORGANISM: Neisseria meningitidis

<400> SEQUENCE: 42

Thr Lys Ile Ser Asp Phe Gly Ser Phe Ile Gly Phe Lys
 1               5                  10

<210> SEQ ID NO 43
<211> LENGTH: 15
<212> TYPE: PRT
<213> ORGANISM: Neisseria meningitidis

<400> SEQUENCE: 43

Gly Phe Lys Gly Ser Glu Asp Leu Gly Glu Gly Leu Lys Ala Val
 1               5                  10                  15

<210> SEQ ID NO 44
<211> LENGTH: 13
<212> TYPE: PRT
<213> ORGANISM: Neisseria meningitidis

<400> SEQUENCE: 44

Val Ser Val Ala Gly Gly Gly Ala Ser Gln Trp Gly Asn
 1               5                  10

<210> SEQ ID NO 45
<211> LENGTH: 19
<212> TYPE: PRT
<213> ORGANISM: Neisseria meningitidis

<400> SEQUENCE: 45
```

-continued

Thr Leu Arg Ala Gly Arg Val Ala Asn Gln Phe Asp Asp Ala Ser Gln
1               5                   10                  15

Ala Ile Asn

<210> SEQ ID NO 46
<211> LENGTH: 14
<212> TYPE: PRT
<213> ORGANISM: Neisseria meningitidis

<400> SEQUENCE: 46

Asp Ser Asn Asn Asp Val Ala Ser Gln Leu Gly Ile Phe Lys
1               5                   10

<210> SEQ ID NO 47
<211> LENGTH: 8
<212> TYPE: PRT
<213> ORGANISM: Neisseria meningitidis

<400> SEQUENCE: 47

Gly Gly Phe Ser Gly Phe Ser Gly
1               5

<210> SEQ ID NO 48
<211> LENGTH: 13
<212> TYPE: PRT
<213> ORGANISM: Neisseria meningitidis

<400> SEQUENCE: 48

Ala Val Val Gly Lys Pro Gly Ser Asp Val Tyr Tyr Ala
1               5                   10

<210> SEQ ID NO 49
<211> LENGTH: 14
<212> TYPE: PRT
<213> ORGANISM: Neisseria meningitidis

<400> SEQUENCE: 49

Tyr Ala Phe Lys Tyr Ala Arg Asn Ala His Val Gly Arg Asn
1               5                   10

<210> SEQ ID NO 50
<211> LENGTH: 23
<212> TYPE: PRT
<213> ORGANISM: Neisseria meningitidis

<400> SEQUENCE: 50

Ala Asn Val Gly Arg Asn Ala Phe Glu Leu Phe Leu Ile Gly Ser Ala
1               5                   10                  15

Thr Ser Asp Glu Ala Lys Gly
            20

<210> SEQ ID NO 51
<211> LENGTH: 21
<212> TYPE: PRT
<213> ORGANISM: Neisseria meningitidis

<400> SEQUENCE: 51

Asp Glu Ala Lys Gly Thr Asp Pro Leu Lys Asn His Gln Val His Arg
1               5                   10                  15

Leu Thr Gly Gly Tyr
            20

-continued

```
<210> SEQ ID NO 52
<211> LENGTH: 16
<212> TYPE: PRT
<213> ORGANISM: Neisseria meningitidis

<400> SEQUENCE: 52

Leu Ser Glu Asn Gly Asp Lys Ala Lys Thr Lys Asn Ser Thr Thr Glu
 1               5                  10                  15

<210> SEQ ID NO 53
<211> LENGTH: 19
<212> TYPE: PRT
<213> ORGANISM: Neisseria meningitidis

<400> SEQUENCE: 53

Val Pro Arg Ile Ser Tyr Ala His Gly Phe Asp Leu Ile Glu Arg Gly
 1               5                  10                  15

Lys Lys Gly

<210> SEQ ID NO 54
<211> LENGTH: 13
<212> TYPE: PRT
<213> ORGANISM: Neisseria meningitidis

<400> SEQUENCE: 54

Glu Arg Gly Lys Lys Gly Glu Asn Thr Ser Tyr Asp Gln
 1               5                  10

<210> SEQ ID NO 55
<211> LENGTH: 15
<212> TYPE: PRT
<213> ORGANISM: Neisseria meningitidis

<400> SEQUENCE: 55

Lys Arg Asn Thr Gly Ile Gly Asn Tyr Thr Gln Ile Asn Ala Ala
 1               5                  10                  15

<210> SEQ ID NO 56
<211> LENGTH: 12
<212> TYPE: PRT
<213> ORGANISM: Artificial Sequence
<220> FEATURE:
<223> OTHER INFORMATION: Synthetic peptide

<400> SEQUENCE: 56

Gly Gly Tyr Tyr Thr Lys Asp Thr Asn Asn Asn Leu
 1               5                  10

<210> SEQ ID NO 57
<211> LENGTH: 373
<212> TYPE: PRT
<213> ORGANISM: Neisseria meningitidis

<400> SEQUENCE: 57

Asp Val Ser Leu Tyr Gly Glu Ile Lys Ala Gly Val Glu Gly Arg Asn
 1               5                  10                  15

Ile Gln Ala Gln Leu Thr Glu Gln Pro Gln Val Thr Asn Gly Val Gln
                 20                  25                  30

Gly Asn Gln Val Lys Val Thr Lys Ala Lys Ser Arg Ile Arg Thr Lys
             35                  40                  45

Ile Ser Asp Phe Gly Ser Thr Ile Gly Phe Lys Gly Ser Glu Asp Leu
         50                  55                  60

Gly Glu Gly Leu Lys Ala Val Trp Gln Leu Glu Gln Asp Val Ser Val
```

```
                65                  70                  75                  80
    Ala Gly Gly Gly Ala Ser Gln Trp Gly Asn Arg Glu Ser Phe Ile Gly
                        85                  90                  95

Leu Ala Gly Glu Phe Gly Thr Leu Arg Ala Gly Arg Val Ala Asn Gln
                    100                 105                 110

Phe Asp Asp Ala Ser Gln Ala Ile Asn Pro Trp Asp Ser Asn Asn Asp
                115                 120                 125

Val Ala Ser Gln Leu Gln Ile Phe Lys Arg His Asp Asp Met Pro Val
        130                 135                 140

Ser Val Arg Tyr Asp Ser Pro Glu Phe Ser Phe Ser Gly Ser Val
    145                 150                 155                 160

Gln Phe Val Pro Ala Gln Asn Ser Lys Ser Ala Tyr Lys Pro Ala Tyr
                    165                 170                 175

Tyr Thr Lys Asp Thr Asn Asn Asn Leu Thr Leu Val Pro Ala Val Val
                180                 185                 190

Gly Lys Pro Gly Ser Asp Val Tyr Tyr Ala Gly Leu Asn Tyr Lys Asn
                195                 200                 205

Gly Gly Phe Ala Gly Asn Tyr Ala Phe Lys Tyr Ala Arg His Ala Asn
        210                 215                 220

Val Gly Arg Asn Ala Phe Glu Leu Phe Leu Ile Gly Ser Ala Thr Ser
    225                 230                 235                 240

Asp Glu Ala Lys Gly Thr Asp Pro Leu Lys His Gln Val His Arg Leu
                    245                 250                 255

Thr Gly Gly Tyr Glu Glu Gly Gly Leu Asn Leu Ala Leu Ala Ala Gln
                260                 265                 270

Leu Asp Leu Ser Glu Asn Gly Asp Lys Ala Lys Thr Lys Asn Ser Thr
                275                 280                 285

Thr Glu Ile Ala Ala Thr Ala Ser Tyr Arg Phe Gly Asn Ala Val Pro
        290                 295                 300

Arg Ile Ser Tyr Ala His Gly Phe Asp Leu Ile Glu Arg Gly Lys Lys
    305                 310                 315                 320

Gly Glu Asn Thr Ser Tyr Asp Gln Ile Ile Ala Gly Val Asp Tyr Asp
                    325                 330                 335

Phe Ser Lys Arg Thr Ser Ala Ile Val Ser Gly Ala Trp Leu Lys Arg
                340                 345                 350

Asn Thr Gly Ile Gly Asn Tyr Thr Gln Ile Asn Ala Ala Ser Val Gly
                355                 360                 365

Leu Arg His Lys Phe
        370

<210> SEQ ID NO 58
<211> LENGTH: 328
<212> TYPE: PRT
<213> ORGANISM: Neisseria meningitidis

<400> SEQUENCE: 58

Asp Val Thr Leu Tyr Gly Ala Ile Lys Ala Gly Val Gln Thr Tyr Arg
    1               5                   10                  15

Ser Val Glu His Thr Asp Gly Lys Val Ser Lys Val Glu Thr Gly Ser
                    20                  25                  30

Glu Ile Ala Asp Phe Gly Ser Lys Ile Gly Phe Lys Gly Gln Glu Asp
                35                  40                  45

Leu Gly Asn Gly Leu Lys Ala Val Trp Gln Leu Glu Gln Gly Ala Ser
        50                  55                  60
```

```
Val Ala Gly Thr Asn Thr Gly Trp Gly Asn Lys Gln Ser Phe Val Gly
 65                  70                  75                  80

Leu Lys Gly Gly Phe Gly Thr Ile Arg Ala Gly Ser Leu Asn Ser Pro
                 85                  90                  95

Leu Lys Asn Thr Gly Ala Asn Val Asn Ala Trp Glu Ser Gly Lys Phe
            100                 105                 110

Thr Gly Asn Val Leu Glu Ile Ser Gly Met Ala Gln Arg Glu His Arg
        115                 120                 125

Tyr Leu Ser Val Arg Tyr Asp Ser Pro Glu Phe Ala Gly Phe Ser Gly
130                 135                 140

Ser Val Gln Tyr Ala Pro Lys Asp Asn Ser Ser Asn Gly Glu Ser
145                 150                 155                 160

Tyr His Val Gly Leu Asn Tyr Gln Asn Ser Gly Phe Phe Ala Gln Tyr
                165                 170                 175

Ala Gly Leu Phe Gln Arg Tyr Gly Glu Gly Thr Lys Lys Ile Glu Asp
            180                 185                 190

Asp Gln Thr Tyr Ser Ile Pro Ser Leu Phe Val Glu Lys Leu Gln Val
        195                 200                 205

His Arg Leu Val Gly Gly Tyr Asp Asn Asn Ala Leu Tyr Val Ser Val
210                 215                 220

Ala Ala Gln Gln Gln Asp Ala Lys Leu Tyr Gly Ala Met Ser Gly Asn
225                 230                 235                 240

Ser His Asn Ser Gln Thr Glu Val Ala Ala Thr Ala Ala Tyr Arg Phe
                245                 250                 255

Gly Asn Val Thr Pro Arg Val Ser Tyr Ala His Gly Phe Lys Gly Thr
            260                 265                 270

Val Asp Ser Ala Asn His Asp Asn Thr Tyr Asp Gln Val Val Val Gly
        275                 280                 285

Ala Glu Tyr Asp Phe Ser Lys Arg Thr Ser Ala Leu Val Ser Ala Gly
290                 295                 300

Trp Leu Gln Gly Gly Lys Gly Ala Asp Lys Ile Val Ser Thr Ala Ser
305                 310                 315                 320

Ala Val Val Leu Arg His Lys Phe
                325

<210> SEQ ID NO 59
<211> LENGTH: 326
<212> TYPE: PRT
<213> ORGANISM: Neisseria meningitidis

<400> SEQUENCE: 59

Asp Val Thr Leu Tyr Gly Thr Ile Lys Ala Gly Val Glu Gly Arg Asn
 1               5                  10                  15

Ile Gln Ala Gln Leu Thr Glu Gln Pro Glu Thr Ser Arg Ser Val Ala
            20                  25                  30

His His Gly Ala Gln Ala Asp Arg Val Lys Thr Ala Thr Glu Ile Ala
        35                  40                  45

Asp Leu Gly Ser Lys Ile Gly Phe Lys Gly Gln Glu Asp Leu Gly Asn
 50                 55                  60

Gly Leu Lys Ala Ile Trp Gln Leu Glu Gln Lys Ala Tyr Val Ser Gly
 65                 70                  75                  80

Thr Asp Thr Gly Trp Gly Asn Arg Gln Ser Phe Ile Gly Leu Lys Gly
                 85                  90                  95

Gly Phe Gly Lys Val Arg Val Gly Arg Leu Asn Ser Tyr Leu Lys Asp
            100                 105                 110
```

```
Thr Gly Gly Phe Asn Pro Trp Glu Gly Lys Ser Tyr Tyr Leu Pro Leu
            115                 120                 125

Ser Asn Ile Ala Gln Pro Glu Glu Arg His Val Ser Val Arg Tyr Asp
    130                 135                 140

Ser Pro Glu Phe Ala Gly Phe Arg Ala Val Gln Tyr Val Pro Asn Asp
145                 150                 155                 160

Asn Ser Gly Lys Asn His Ser Glu Ser Tyr His Ala Gly Phe Asn Tyr
                165                 170                 175

Lys Asn Ser Gly Phe Phe Val Gln Tyr Ala Gly Phe Tyr Lys Arg His
                180                 185                 190

Ser Tyr Thr Thr Glu Lys His Phe Glu Leu Phe Leu Leu Gln Val His
                195                 200                 205

Arg Leu Val Gly Gly Tyr Asp His Asp Ala Leu Tyr Ala Ser Val Ala
            210                 215                 220

Val Gln Gln Gln Asp Ala Lys Leu Thr Trp Arg Asn Asp Asn Ser His
225                 230                 235                 240

Asn Ser Gln Thr Glu Val Ala Ala Thr Ala Ala Tyr Arg Phe Gly Asn
                245                 250                 255

Val Thr Pro Arg Val Ser Tyr Ala His Gly Phe Lys Gly Ser Val Tyr
            260                 265                 270

Asp Ala Asp Asn Asp Asn Thr Tyr Asp Gln Val Val Gly Ala Glu
            275                 280                 285

Tyr Asp Phe Ser Lys Arg Thr Ser Ala Leu Val Ser Ala Gly Trp Leu
    290                 295                 300

Gln Arg Gly Lys Gly Thr Glu Lys Phe Val Ala Thr Val Gly Gly Val
305                 310                 315                 320

Gly Leu Arg His Lys Phe
                325

<210> SEQ ID NO 60
<211> LENGTH: 353
<212> TYPE: PRT
<213> ORGANISM: Neisseria meningitidis

<400> SEQUENCE: 60

Asp Val Thr Leu Tyr Gly Thr Ile Lys Ala Gly Val Glu Gly Arg Asn
1               5                   10                  15

Ile Gln Ala Gln Leu Thr Glu Gln Pro Glu Val Ser Arg Val Lys Asp
            20                  25                  30

Ala Gly Thr Tyr Lys Ala Gln Gly Gly Lys Ser Lys Thr Ala Thr Gln
            35                  40                  45

Ile Ala Asp Phe Gly Ser Lys Ile Gly Phe Lys Gly Gln Glu Asp Leu
    50                  55                  60

Gly Asn Gly Leu Lys Ala Ile Trp Gln Leu Glu Gln Lys Ala Ser Ile
65                  70                  75                  80

Ala Gly Thr Asn Ser Gly Trp Gly Asn Arg Gln Ser Phe Ile Gly Leu
                85                  90                  95

Lys Gly Gly Phe Gly Thr Val Arg Ala Gly Asn Leu Asn Thr Val Leu
            100                 105                 110

Lys Asp Ser Gly Asp Asn Val Asn Ala Trp Glu Ser Gly Ser Asn Thr
            115                 120                 125

Glu Asp Val Leu Gly Leu Gly Thr Ile Gly Arg Val Glu Ser Arg Glu
    130                 135                 140

Ile Ser Val Arg Tyr Asp Ser Pro Val Phe Ala Gly Phe Ser Gly Ser
```

```
            145                 150                 155                 160
Val Gln Tyr Val Pro Arg Asp Asn Ala Asn Asp Val Asp Lys Tyr Lys
                165                 170                 175

His Thr Lys Ser Ser Arg Glu Ser Tyr His Ala Gly Leu Lys Tyr Glu
            180                 185                 190

Asn Ala Gly Phe Phe Gly Gln Tyr Ala Gly Ser Phe Ala Lys Tyr Ala
        195                 200                 205

Asp Leu Asn Thr Asp Ala Glu Arg Val Ala Val Asn Thr Ala Asn Ala
    210                 215                 220

His Pro Val Lys Asp Tyr Gln Val His Arg Val Val Ala Gly Tyr Asp
225                 230                 235                 240

Ala Asn Asp Leu Tyr Val Ser Val Ala Gly Gln Tyr Glu Ala Ala Lys
                245                 250                 255

Asn Asn Glu Val Gly Ser Thr Lys Gly Lys Lys His Gln Thr Gln Val
            260                 265                 270

Ala Ala Thr Ala Ala Tyr Arg Phe Gly Asn Val Thr Pro Arg Val Ser
        275                 280                 285

Tyr Ala His Gly Phe Lys Ala Lys Val Asn Gly Val Lys Asp Ala Asn
    290                 295                 300

Tyr Gln Gln Asp Gln Val Ile Val Gly Ala Asp Tyr Asp Phe Ser Lys
305                 310                 315                 320

Arg Thr Ser Ala Leu Val Ser Ala Gly Trp Leu Lys Gln Lys Gly
                325                 330                 335

Thr Gly Lys Val Glu Gln Thr Ala Ser Met Val Gly Leu Arg His Lys
            340                 345                 350

Phe

<210> SEQ ID NO 61
<211> LENGTH: 38
<212> TYPE: PRT
<213> ORGANISM: Neisseria meningitidis

<400> SEQUENCE: 61

Gly Arg Asn Tyr Gln Leu Gln Leu Thr Glu Ala Gln Ala Ala Asn Gly
1               5                   10                  15

Gly Ala Gly Gln Val Lys Val Thr Lys Val Thr Lys Ala Lys Ser Arg
            20                  25                  30

Ile Arg Thr Lys Ile Ser
        35

<210> SEQ ID NO 62
<211> LENGTH: 116
<212> TYPE: DNA
<213> ORGANISM: Neisseria meningitidis

<400> SEQUENCE: 62
ggcaggaact accagctgca attgactgaa gcacaagccg ctaacggtgg agcgagggtc    60
aggtaaaagt tactaaagtt actaaggcca aaagccgcat caggacgaaa atcagt      116

<210> SEQ ID NO 63
<211> LENGTH: 36
<212> TYPE: PRT
<213> ORGANISM: Neisseria meningitidis

<400> SEQUENCE: 63

Ala Gln Leu Thr Glu Gln Pro Gln Ala Thr Asn Gly Val Gln Gly Gly
1               5                   10                  15
```

```
Arg Gln Gly Asn Gln Val Thr Val Thr Lys Val Lys Ser Arg Ile Arg
            20                  25                  30

Thr Glu Ile Ser
        35

<210> SEQ ID NO 64
<211> LENGTH: 122
<212> TYPE: DNA
<213> ORGANISM: Neisseria meningitidis

<400> SEQUENCE: 64
ggcaggaaca tctaggcgca attgaccgag cagccccaag caactaacgg tgtgcaaggg    60
gtcggcaagg caatcaggta acagttacta aggtcaaaag ccgcatcagg acggaaatca   120
gc                                                                 122

<210> SEQ ID NO 65
<211> LENGTH: 33
<212> TYPE: PRT
<213> ORGANISM: Neisseria meningitidis

<400> SEQUENCE: 65

Gly Arg Asn Phe Gln Leu Gln Leu Thr Glu Pro Pro Ser Lys Ser Gln
 1               5                  10                  15

Pro Gln Val Lys Val Thr Lys Ala Lys Ser Arg Ile Arg Thr Lys Ile
            20                  25                  30

Ser

<210> SEQ ID NO 66
<211> LENGTH: 99
<212> TYPE: DNA
<213> ORGANISM: Neisseria meningitidis
<220> FEATURE:
<221> NAME/KEY: CDS
<222> LOCATION: (1)...(99)

<400> SEQUENCE: 66 ggc agg aac ttc cag ctg cag ttg acc gaa ccg ccc tca aag agt caa    48
Gly Arg Asn Phe Gln Leu Gln Leu Thr Glu Pro Pro Ser Lys Ser Gln
 1               5                  10                  15 cct cag gta aaa gtt act aag gcc aaa agc cgc atc agg acg aaa atc    96
Pro Gln Val Lys Val Thr Lys Ala Lys Ser Arg Ile Arg Thr Lys Ile
            20                  25                  30 agt                                                                99
Ser

<210> SEQ ID NO 67
<211> LENGTH: 33
<212> TYPE: PRT
<213> ORGANISM: Neisseria meningitidis

<400> SEQUENCE: 67

Gly Asn Asn Ile Gln Leu Gln Leu Thr Glu Pro Pro Ser Lys Gly Gln
 1               5                  10                  15

Thr Gly Asn Lys Val Thr Lys Ala Lys Ser Arg Ile Arg Thr Lys Ile
            20                  25                  30

Ser

<210> SEQ ID NO 68
<211> LENGTH: 99
<212> TYPE: DNA
```

<213> ORGANISM: Neisseria meningitidis
<220> FEATURE:
<221> NAME/KEY: CDS
<222> LOCATION: (1)...(99)

<400> SEQUENCE: 68

| ggc | aac | aac | att | cag | ctg | caa | ttg | acc | gaa | cca | ccc | tca | aaa | ggt | cag | 48 |
| Gly | Asn | Asn | Ile | Gln | Leu | Gln | Leu | Thr | Glu | Pro | Pro | Ser | Lys | Gly | Gln | |
| 1 | | | | 5 | | | | | 10 | | | | | 15 | | |

| acg | ggc | aat | aaa | gtt | act | aag | gcc | aaa | agc | cgc | atc | agg | acg | aaa | atc | 96 |
| Thr | Gly | Asn | Lys | Val | Thr | Lys | Ala | Lys | Ser | Arg | Ile | Arg | Thr | Lys | Ile | |
| | | | 20 | | | | | 25 | | | | | 30 | | | |

| agt | 99 |
| Ser | |

<210> SEQ ID NO 69
<211> LENGTH: 36
<212> TYPE: PRT
<213> ORGANISM: Neisseria meningitidis

<400> SEQUENCE: 69

Gly Arg Asn Tyr Gln Leu Gln Leu Thr Glu Gln Pro Ser Arg Thr Gln
1               5                   10                  15

Gly Gln Thr Asn Gln Val Lys Val Thr Lys Ala Lys Ser Arg Ile Arg
            20                  25                  30

Thr Lys Ile Ser
            35

<210> SEQ ID NO 70
<211> LENGTH: 110
<212> TYPE: DNA
<213> ORGANISM: Neisseria meningitidis

<400> SEQUENCE: 70
ggcaggaact accagctgca attgactgaa caaccctcaa gaactcaagg tcaaacgaga     60
atcaggtaaa agttactaag gccaaaagcc gcatcaggac gaaaatcagt              110

<210> SEQ ID NO 71
<211> LENGTH: 31
<212> TYPE: PRT
<213> ORGANISM: Neisseria meningitidis

<400> SEQUENCE: 71

Gly Arg Asn Ile Gln Leu Gln Leu Thr Glu Pro Leu Pro Asn Ile Gln
1               5                   10                  15

Pro Gln Val Thr Lys Arg Lys Ser Arg Ile Arg Thr Lys Ile Ser
            20                  25                  30

<210> SEQ ID NO 72
<211> LENGTH: 93
<212> TYPE: DNA
<213> ORGANISM: Neisseria meningitidis
<220> FEATURE:
<221> NAME/KEY: CDS
<222> LOCATION: (1)...(93)

<400> SEQUENCE: 72

| ggc | agg | aac | atc | cag | ctg | cag | ttg | acc | gaa | ccg | ctc | cca | aat | att | caa | 48 |
| Gly | Arg | Asn | Ile | Gln | Leu | Gln | Leu | Thr | Glu | Pro | Leu | Pro | Asn | Ile | Gln | |
| 1 | | | | 5 | | | | | 10 | | | | | 15 | | |

| cct | cag | gtt | act | aag | cgc | aaa | agc | cgc | atc | agg | acg | aaa | atc | agc | 93 |
| Pro | Gln | Val | Thr | Lys | Arg | Lys | Ser | Arg | Ile | Arg | Thr | Lys | Ile | Ser | |
| | | | 20 | | | | | 25 | | | | | 30 | | |

<210> SEQ ID NO 73
<211> LENGTH: 31
<212> TYPE: PRT
<213> ORGANISM: Neisseria meningitidis

<400> SEQUENCE: 73

Gly Arg Asn Ile Gln Leu Gln Leu Thr Glu Pro Leu Pro Asn Ile Gln
1               5                   10                  15

Pro Gln Val Thr Lys Arg Lys Ser Arg Ile Arg Thr Lys Ile Ser
            20                  25                  30

<210> SEQ ID NO 74
<211> LENGTH: 93
<212> TYPE: DNA
<213> ORGANISM: Neisseria meningitidis
<220> FEATURE:
<221> NAME/KEY: CDS
<222> LOCATION: (1)...(93)

<400> SEQUENCE: 74 ggc agg aac atc cag ctg cag ttg acc gaa ccg ctc cca aat att caa    48
Gly Arg Asn Ile Gln Leu Gln Leu Thr Glu Pro Leu Pro Asn Ile Gln
1               5                   10                  15 cct cag gtt act aag cgc aaa agc cgc atc agg acg aaa atc agc        93
Pro Gln Val Thr Lys Arg Lys Ser Arg Ile Arg Thr Lys Ile Ser
            20                  25                  30

<210> SEQ ID NO 75
<211> LENGTH: 131
<212> TYPE: PRT
<213> ORGANISM: Neisseria meningitidis

<400> SEQUENCE: 75

Thr Leu Arg Ala Gly Arg Val Ala Asn Gln Phe Asp Asp Ala Ser Gln
1               5                   10                  15

Ala Ile Asp Pro Trp Asp Ser Asn Asn Asp Val Ala Ser Gln Leu Gly
            20                  25                  30

Ile Phe Lys Arg His Asp Asp Met Pro Val Ser Val Arg Tyr Asp Ser
        35                  40                  45

Pro Glu Phe Ser Gly Phe Ser Gly Ser Val Gln Phe Val Pro Ile Gln
    50                  55                  60

Asn Ser Lys Ser Ala Tyr Thr Pro Ala Tyr Tyr Thr Lys Asp Thr Asn
65                  70                  75                  80

Asn Asn Leu Thr Leu Val Pro Ala Val Val Gly Lys Pro Gly Ser Asp
                85                  90                  95

Val Tyr Tyr Ala Gly Leu Asn Tyr Lys Asn Gly Phe Ala Gly Asn
            100                 105                 110

Tyr Ala Phe Lys Tyr Ala Arg His Ala Asn Val Gly Arg Asn Ala Phe
        115                 120                 125

Glu Leu Phe
    130

<210> SEQ ID NO 76
<211> LENGTH: 393
<212> TYPE: DNA
<213> ORGANISM: Neisseria meningitidis
<220> FEATURE:
<221> NAME/KEY: CDS
<222> LOCATION: (1)...(393)

<400> SEQUENCE: 76

```
acg ctg cgc gcc ggt cgc gtt gcg aat cag ttt gac gat gcc agc caa        48
Thr Leu Arg Ala Gly Arg Val Ala Asn Gln Phe Asp Asp Ala Ser Gln
1               5                   10                  15 gcc att gat cct tgg gac agc aat aat gat gtg gct tcg caa ttg ggt        96
Ala Ile Asp Pro Trp Asp Ser Asn Asn Asp Val Ala Ser Gln Leu Gly
            20                  25                  30 att ttc aaa cgc cac gac gac atg ccg gtt tct gta cgc tac gat tcc       144
Ile Phe Lys Arg His Asp Asp Met Pro Val Ser Val Arg Tyr Asp Ser
        35                  40                  45 ccc gaa ttt tcc ggt ttc agc ggc agc gtt caa ttc gtt ccg atc caa       192
Pro Glu Phe Ser Gly Phe Ser Gly Ser Val Gln Phe Val Pro Ile Gln
    50                  55                  60 aac agc aag tcc gcc tat acg ccg gct tat tat act aag gat aca aac       240
Asn Ser Lys Ser Ala Tyr Thr Pro Ala Tyr Tyr Thr Lys Asp Thr Asn
65                  70                  75                  80 aat aat ctt act ctc gtt ccg gct gtt gtc ggc aag ccc gga tcg gat       288
Asn Asn Leu Thr Leu Val Pro Ala Val Val Gly Lys Pro Gly Ser Asp
                85                  90                  95 gtg tat tat gcc ggt ctg aat tac aaa aat ggc ggt ttt gcc ggg aac       336
Val Tyr Tyr Ala Gly Leu Asn Tyr Lys Asn Gly Gly Phe Ala Gly Asn
            100                 105                 110 tat gcc ttt aaa tat gcg aga cac gcc aat gtc gga cgt aat gct ttt       384
Tyr Ala Phe Lys Tyr Ala Arg His Ala Asn Val Gly Arg Asn Ala Phe
        115                 120                 125 gag ttg ttc                                                           393
Glu Leu Phe
    130
```

<210> SEQ ID NO 77
<211> LENGTH: 130
<212> TYPE: PRT
<213> ORGANISM: Neisseria meningitidis

<400> SEQUENCE: 77

```
Thr Leu Arg Thr Gly Arg Val Ala Asn Gln Phe Asp Asp Ala Ser Gln
1               5                   10                  15

Ala Ile Asp Pro Trp Asp Ser Asn Asn Asp Val Ala Ser Gln Leu Gly
            20                  25                  30

Ile Phe Lys Arg His Asp Asp Met Pro Val Ser Val Arg Tyr Asp Ser
        35                  40                  45

Pro Asp Phe Ser Gly Phe Ser Gly Ser Val Gln Phe Val Pro Ala Gln
    50                  55                  60

Asn Ser Lys Ser Ala Tyr Thr Pro Ala Tyr Val Ala Val Glu Asn Gly
65                  70                  75                  80

Val Ala Lys Lys Val Ala Val Val Gly Lys Pro Gly Ser Asp Val
                85                  90                  95

Tyr Tyr Ala Gly Leu Asn Tyr Lys Asn Gly Gly Phe Ala Gly Asn Tyr
            100                 105                 110

Ala Phe Lys Tyr Ala Lys His Ala Asn Val Gly Arg Asp Ala Phe Glu
        115                 120                 125

Leu Phe
    130
```

<210> SEQ ID NO 78
<211> LENGTH: 390
<212> TYPE: DNA
<213> ORGANISM: Neisseria meningitidis
<220> FEATURE:
<221> NAME/KEY: CDS

<222> LOCATION: (1)...(390)

<400> SEQUENCE: 78

```
acg ctg cgc acc ggt cgc gtt gcg aat cag ttt gac gat gcc agc caa    48
Thr Leu Arg Thr Gly Arg Val Ala Asn Gln Phe Asp Asp Ala Ser Gln
  1               5                  10                  15 gcc att gat cct tgg gac agc aat aat gat gtg gct tcg caa ttg ggt    96
Ala Ile Asp Pro Trp Asp Ser Asn Asn Asp Val Ala Ser Gln Leu Gly
             20                  25                  30 att ttc aaa cgc cac gac gat atg ccg gtt tct gta cgc tac gac tct   144
Ile Phe Lys Arg His Asp Asp Met Pro Val Ser Val Arg Tyr Asp Ser
         35                  40                  45 ccg gac ttt tcc ggt ttc agc ggc agc gtc caa ttc gtt ccg gct caa   192
Pro Asp Phe Ser Gly Phe Ser Gly Ser Val Gln Phe Val Pro Ala Gln
 50                  55                  60 aac agc aag tcc gcc tat acg ccg gct tat gtg gcg gtg gaa aat ggc   240
Asn Ser Lys Ser Ala Tyr Thr Pro Ala Tyr Val Ala Val Glu Asn Gly
 65                  70                  75                  80 gta gct aaa aaa gtt gcg gct gtt gtc ggc aag ccc gga tcg gat gtg   288
Val Ala Lys Lys Val Ala Ala Val Val Gly Lys Pro Gly Ser Asp Val
                 85                  90                  95 tat tat gcc ggt ctg aat tat aag aat ggc ggt ttt gcc ggg aac tat   336
Tyr Tyr Ala Gly Leu Asn Tyr Lys Asn Gly Gly Phe Ala Gly Asn Tyr
             100                 105                 110 gcc ttt aaa tat gcg aaa cac gcc aat gtc gga cgt gat gct ttt gag   384
Ala Phe Lys Tyr Ala Lys His Ala Asn Val Gly Arg Asp Ala Phe Glu
         115                 120                 125 ttg ttc                                                            390
Leu Phe
    130
```

<210> SEQ ID NO 79
<211> LENGTH: 130
<212> TYPE: PRT
<213> ORGANISM: Neisseria meningitidis
<220> FEATURE:
<221> NAME/KEY: VARIANT
<222> LOCATION: 3
<223> OTHER INFORMATION: Xaa = Leu, Pro, His, Gln or Arg
<220> FEATURE:
<221> NAME/KEY: VARIANT
<222> LOCATION: 4
<223> OTHER INFORMATION: Xaa = Any Amino Acid

<400> SEQUENCE: 79

```
Thr Leu Xaa Xaa Gly Arg Val Ala Asn Gln Phe Asp Asp Ala Ser Gln
  1               5                  10                  15

Ala Ile Asp Pro Trp Asp Ser Asn Asn Asp Val Ala Ser Gln Leu Gly
             20                  25                  30

Ile Phe Lys Arg His Asp Asp Met Pro Val Ser Val Arg Tyr Asp Ser
         35                  40                  45

Pro Asp Phe Ser Gly Phe Ser Gly Ser Val Gln Phe Val Pro Ile Gln
 50                  55                  60

Asn Ser Lys Ser Ala Tyr Thr Pro Ala His Asn Thr Arg Gln Asn Asn
 65                  70                  75                  80

Ala Asp Val Phe Val Pro Ala Val Val Gly Lys Pro Gly Ser Asp Val
                 85                  90                  95

Tyr Tyr Ala Gly Leu Asn Tyr Lys Asn Gly Gly Phe Ala Gly Arg Tyr
             100                 105                 110

Ala Phe Lys Tyr Ala Arg His Ala Asn Val Gly Arg Asp Ala Phe Glu
         115                 120                 125
```

```
<210> SEQ ID NO 80
<211> LENGTH: 390
<212> TYPE: DNA
<213> ORGANISM: Neisseria meningitidis
<220> FEATURE:
<221> NAME/KEY: misc_feature
<222> LOCATION: 8, 9, 10, 11, 12
<223> OTHER INFORMATION: n = A,T,C or G
<220> FEATURE:
<221> NAME/KEY: CDS
<222> LOCATION: (1)...(390)

<400> SEQUENCE: 80
```

| | | | | | | | | | | | | | | | | |
|---|---|---|---|---|---|---|---|---|---|---|---|---|---|---|---|---|
| acg | ctg | cnn | nnn | ggt | cgc | gtc | gcg | aat | cag | ttt | gac | gat | gcc | agc | caa | 48 |
| Thr | Leu | Xaa | Xaa | Gly | Arg | Val | Ala | Asn | Gln | Phe | Asp | Asp | Ala | Ser | Gln | |
| 1 | | | | 5 | | | | | 10 | | | | | 15 | | |
| gcc | att | gat | cct | tgg | gac | agc | aac | aat | gat | gtg | gct | tcg | caa | ttg | ggt | 96 |
| Ala | Ile | Asp | Pro | Trp | Asp | Ser | Asn | Asn | Asp | Val | Ala | Ser | Gln | Leu | Gly | |
| | | | 20 | | | | | 25 | | | | | 30 | | | |
| att | ttc | aaa | cgc | cac | gac | gat | atg | ccg | gtt | tct | gta | cgc | tac | gac | tct | 144 |
| Ile | Phe | Lys | Arg | His | Asp | Asp | Met | Pro | Val | Ser | Val | Arg | Tyr | Asp | Ser | |
| | | 35 | | | | | 40 | | | | | 45 | | | | |
| ccg | gac | ttt | tcc | ggt | ttc | agc | ggc | agc | gtc | caa | ttc | gtt | ccg | atc | caa | 192 |
| Pro | Asp | Phe | Ser | Gly | Phe | Ser | Gly | Ser | Val | Gln | Phe | Val | Pro | Ile | Gln | |
| 50 | | | | | 55 | | | | | 60 | | | | | | |
| aac | agc | aag | tcc | gcc | tat | acg | ccg | gct | cat | aat | act | agg | cag | aac | aat | 240 |
| Asn | Ser | Lys | Ser | Ala | Tyr | Thr | Pro | Ala | His | Asn | Thr | Arg | Gln | Asn | Asn | |
| 65 | | | | | 70 | | | | | 75 | | | | | 80 | |
| gct | gat | gtt | ttc | gtt | ccg | gct | gtt | gtc | ggc | aag | ccc | gga | tcg | gat | gtg | 288 |
| Ala | Asp | Val | Phe | Val | Pro | Ala | Val | Val | Gly | Lys | Pro | Gly | Ser | Asp | Val | |
| | | | | 85 | | | | | 90 | | | | | 95 | | |
| tat | tat | gcc | ggt | ctg | aat | tac | aaa | aat | ggc | ggt | ttt | gcc | ggg | cgc | tat | 336 |
| Tyr | Tyr | Ala | Gly | Leu | Asn | Tyr | Lys | Asn | Gly | Gly | Phe | Ala | Gly | Arg | Tyr | |
| | | | 100 | | | | | 105 | | | | | 110 | | | |
| gcc | ttt | aaa | tat | gcg | aga | cac | gcc | aat | gtc | gga | cgt | gat | gct | ttt | gag | 384 |
| Ala | Phe | Lys | Tyr | Ala | Arg | His | Ala | Asn | Val | Gly | Arg | Asp | Ala | Phe | Glu | |
| | | 115 | | | | | 120 | | | | | 125 | | | | |
| ttg | ttc | | | | | | | | | | | | | | | 390 |
| Leu | Phe | | | | | | | | | | | | | | | |
| | 130 | | | | | | | | | | | | | | | |

```
<210> SEQ ID NO 81
<211> LENGTH: 132
<212> TYPE: PRT
<213> ORGANISM: Neisseria meningitidis

<400> SEQUENCE: 81
```

Thr Leu Arg Thr Gly Arg Val Ala Asn Gln Phe Asp Asp Ala Ser Gln
1               5                   10                  15

Ala Ile Asp Pro Trp Asp Ser Asn Asn Asp Val Ala Ser Gln Leu Gly
            20                  25                  30

Ile Phe Lys Arg His Asp Asp Met Ser Val Ser Val Arg Tyr Asp Ser
        35                  40                  45

Pro Glu Phe Ser Gly Phe Ser Gly Ser Val Gln Phe Val Pro Ala Gln
50                  55                  60

Asn Ser Lys Ser Ala Tyr Thr Pro Ala His Phe Val Gln Asn Lys Gln
65                  70                  75                  80

Asn Gln Arg Pro Thr Leu Val Pro Ala Val Val Gly Lys Pro Gly Ser

```
                    85                  90                  95
Asp Val Tyr Tyr Ala Gly Leu Asn Tyr Lys Asn Gly Phe Ala Gly
            100                 105                 110

Asn Tyr Ala Phe Lys Tyr Ala Lys His Ala Asn Val Gly Arg Asp Ala
        115                 120                 125

Phe Glu Leu Phe
    130

<210> SEQ ID NO 82
<211> LENGTH: 396
<212> TYPE: DNA
<213> ORGANISM: Neisseria meningitidis
<220> FEATURE:
<221> NAME/KEY: CDS
<222> LOCATION: (1)...(396)

<400> SEQUENCE: 82 acg ctg cgc acc ggt cgc gtt gca aat cag ttt gac gat gcc agc caa      48
Thr Leu Arg Thr Gly Arg Val Ala Asn Gln Phe Asp Asp Ala Ser Gln
 1               5                  10                  15 gcc att gat cct tgg gac agc aat aat gat gtg gct tcg caa ttg ggt      96
Ala Ile Asp Pro Trp Asp Ser Asn Asn Asp Val Ala Ser Gln Leu Gly
            20                  25                  30 att ttc aaa cgc cac gac gat atg tcg gtt tct gta cgc tac gat tcc     144
Ile Phe Lys Arg His Asp Asp Met Ser Val Ser Val Arg Tyr Asp Ser
        35                  40                  45 ccc gaa ttt tcc ggt ttt agc ggc agc gtc caa ttc gtt ccg gcc caa     192
Pro Glu Phe Ser Gly Phe Ser Gly Ser Val Gln Phe Val Pro Ala Gln
    50                  55                  60 aac agc aag tcc gcc tat acg ccg gct cat ttt gtt cag aat aag caa     240
Asn Ser Lys Ser Ala Tyr Thr Pro Ala His Phe Val Gln Asn Lys Gln
65                  70                  75                  80 aat cag cgg cct act ctc gtt ccg gct gtt gtc ggc aag ccg ggg tcg     288
Asn Gln Arg Pro Thr Leu Val Pro Ala Val Val Gly Lys Pro Gly Ser
                85                  90                  95 gat gtg tat tat gcc ggt ctg aat tac aaa aat ggc ggt ttt gcc ggg     336
Asp Val Tyr Tyr Ala Gly Leu Asn Tyr Lys Asn Gly Gly Phe Ala Gly
            100                 105                 110 aac tat gcc ttt aaa tac gcg aaa cac gcc aat gtg ggc cgt gat gct     384
Asn Tyr Ala Phe Lys Tyr Ala Lys His Ala Asn Val Gly Arg Asp Ala
        115                 120                 125 ttt gag ttg ttc                                                      396
Phe Glu Leu Phe
    130

<210> SEQ ID NO 83
<211> LENGTH: 132
<212> TYPE: PRT
<213> ORGANISM: Neisseria meningitidis

<400> SEQUENCE: 83

Thr Leu Arg Thr Gly Arg Val Ala Asn Gln Phe Asp Asp Ala Ser Gln
 1               5                  10                  15

Ala Ile Asp Pro Trp Asp Ser Asn Asn Asp Val Ala Ser Gln Leu Gly
            20                  25                  30

Ile Phe Lys Arg His Asp Asp Met Ser Val Ser Val Arg Tyr Asp Ser
        35                  40                  45

Pro Glu Phe Ser Gly Phe Ser Gly Ser Val Gln Phe Val Pro Ala Gln
    50                  55                  60

Asn Ser Lys Ser Ala Tyr Thr Pro Ala His Phe Val Gln Asn Lys Gln
```

```
                65                  70                  75                  80
Asn Gln Arg Pro Thr Leu Val Pro Ala Val Val Gly Lys Pro Gly Ser
                    85                  90                  95

Asp Val Tyr Tyr Ala Gly Leu Asn Tyr Lys Asn Gly Gly Phe Ala Gly
            100                 105                 110

Asn Tyr Ala Phe Lys Tyr Ala Lys His Ala Asn Val Gly Arg Asp Ala
        115                 120                 125

Phe Glu Leu Phe
    130

<210> SEQ ID NO 84
<211> LENGTH: 396
<212> TYPE: DNA
<213> ORGANISM: Neisseria meningitidis
<220> FEATURE:
<221> NAME/KEY: CDS
<222> LOCATION: (1)...(396)

<400> SEQUENCE: 84 acg ctg cgc acc ggt cgc gtt gca aat cag ttt gac gat gcc agc caa       48
Thr Leu Arg Thr Gly Arg Val Ala Asn Gln Phe Asp Asp Ala Ser Gln
1               5                   10                  15 gcc att gat cct tgg gac agc aat aat gat gtg gct tcg caa ttg ggt       96
Ala Ile Asp Pro Trp Asp Ser Asn Asn Asp Val Ala Ser Gln Leu Gly
            20                  25                  30 att ttc aaa cgc cac gac gat atg tcg gtt tct gta cgc tac gat tcc      144
Ile Phe Lys Arg His Asp Asp Met Ser Val Ser Val Arg Tyr Asp Ser
        35                  40                  45 ccc gaa ttt tcc ggt ttt agc ggc agc gtc caa ttc gtt ccg gcc caa      192
Pro Glu Phe Ser Gly Phe Ser Gly Ser Val Gln Phe Val Pro Ala Gln
    50                  55                  60 aac agc aag tcc gcc tat acg ccg gct cat ttt gtt cag aat aag caa      240
Asn Ser Lys Ser Ala Tyr Thr Pro Ala His Phe Val Gln Asn Lys Gln
65                  70                  75                  80 aat cag cgg cct act ctc gtt ccg gct gtt gtc ggc aag ccg ggg tcg      288
Asn Gln Arg Pro Thr Leu Val Pro Ala Val Val Gly Lys Pro Gly Ser
                85                  90                  95 gat gtg tat tat gcc ggt ctg aat tac aaa aat ggc ggt ttt gcc ggg      336
Asp Val Tyr Tyr Ala Gly Leu Asn Tyr Lys Asn Gly Gly Phe Ala Gly
            100                 105                 110 aac tat gcc ttt aaa tac gcg aaa cac gcc aat gtg ggc cgt gat gct      384
Asn Tyr Ala Phe Lys Tyr Ala Lys His Ala Asn Val Gly Arg Asp Ala
        115                 120                 125 ttt gag ttg ttc                                                      396
Phe Glu Leu Phe
    130

<210> SEQ ID NO 85
<211> LENGTH: 87
<212> TYPE: PRT
<213> ORGANISM: Neisseria meningitidis

<400> SEQUENCE: 85

Arg Tyr Asp Ser Pro Asp Phe Ser Gly Phe Ser Gly Ser Val Gln Phe
1               5                   10                  15

Val Pro Ala Gln Asn Ser Lys Ser Ala Tyr Thr Pro Thr Tyr Thr
            20                  25                  30

Val Asp Ser Ser Gly Val Val Thr Pro Val Pro Ala Val Val Gly Lys
        35                  40                  45

Pro Gly Ser Asp Val Tyr Tyr Ala Gly Leu Asn Tyr Lys Asn Gly Gly
```

```
                  50                  55                  60
Phe Ala Gly Asn Tyr Ala Phe Lys Tyr Ala Lys His Ala Asn Val Gly
 65                  70                  75                  80

Arg Asp Ala Phe Asn Leu Phe
                85
```

<210> SEQ ID NO 86
<211> LENGTH: 261
<212> TYPE: DNA
<213> ORGANISM: Neisseria meningitidis
<220> FEATURE:
<221> NAME/KEY: CDS
<222> LOCATION: (1)...(261)

<400> SEQUENCE: 86

```
cgc tac gac tct ccg gac ttt tcc ggt ttc agc ggc agc gtc caa ttc      48
Arg Tyr Asp Ser Pro Asp Phe Ser Gly Phe Ser Gly Ser Val Gln Phe
  1               5                  10                  15 gtt ccg gcc caa aac agc aaa tcc gcc tat acg ccg gct act tat act      96
Val Pro Ala Gln Asn Ser Lys Ser Ala Tyr Thr Pro Ala Thr Tyr Thr
                 20                  25                  30 gtg agt agt ggt gtt gtt act ccc gtt cct gct gtt gtc ggc aag         144
Val Asp Ser Ser Gly Val Val Thr Pro Val Pro Ala Val Val Gly Lys
             35                  40                  45 ccc gga tcg gat gtg tat tat gcc ggt ctg aat tac aaa aat ggc ggt     192
Pro Gly Ser Asp Val Tyr Tyr Ala Gly Leu Asn Tyr Lys Asn Gly Gly
         50                  55                  60 ttt gcc ggg aac tat gcc ttt aaa tac gcg aaa cac gcc aat gtg ggc     240
Phe Ala Gly Asn Tyr Ala Phe Lys Tyr Ala Lys His Ala Asn Val Gly
 65                  70                  75                  80 cgt gat gct ttt aat ttg ttc                                         261
Arg Asp Ala Phe Asn Leu Phe
                 85
```

<210> SEQ ID NO 87
<211> LENGTH: 83
<212> TYPE: PRT
<213> ORGANISM: Neisseria meningitidis

<400> SEQUENCE: 87

```
Arg Tyr Asp Ser Pro Asp Phe Ser Gly Phe Ser Gly Ser Val Gln Phe
  1               5                  10                  15

Val Pro Ala Gln Asn Ser Lys Ser Ala Tyr Lys Pro Ala Tyr Val Asp
                 20                  25                  30

Glu Lys Lys Met Val His Ala Ala Val Val Gly Lys Pro Gly Ser Asp
             35                  40                  45

Val Tyr Tyr Ala Gly Leu Asn Tyr Lys Asn Gly Gly Phe Ala Gly Asn
         50                  55                  60

Tyr Ala Phe Lys Tyr Ala Lys His Ala Asn Val Gly Arg Asp Ala Phe
 65                  70                  75                  80

Asn Leu Phe
```

<210> SEQ ID NO 88
<211> LENGTH: 249
<212> TYPE: DNA
<213> ORGANISM: Neisseria meningitidis
<220> FEATURE:
<221> NAME/KEY: CDS
<222> LOCATION: (1)...(249)

<400> SEQUENCE: 88

-continued

```
cgc tac gac tct ccg gac ttt tcc ggt ttc agc ggt agc gtc caa ttc        48
Arg Tyr Asp Ser Pro Asp Phe Ser Gly Phe Ser Gly Ser Val Gln Phe
 1               5                  10                  15 gtt ccg gct caa aac agc aag tcc gcc tat aag ccg gct tat gtg gat        96
Val Pro Ala Gln Asn Ser Lys Ser Ala Tyr Lys Pro Ala Tyr Val Asp
             20                  25                  30 gag aag aaa atg gtt cat gcg gct gtt gtc ggc aag ccc gga tcg gat       144
Glu Lys Lys Met Val His Ala Ala Val Val Gly Lys Pro Gly Ser Asp
         35                  40                  45 gtg tat tat gcc ggt ctg aat tac aaa aat ggc ggt ttt gcc ggg aac       192
Val Tyr Tyr Ala Gly Leu Asn Tyr Lys Asn Gly Gly Phe Ala Gly Asn
     50                  55                  60 tat gcc ttt aaa tat gcg aaa cac gcc aat gtg ggc cgt gat gct ttt       240
Tyr Ala Phe Lys Tyr Ala Lys His Ala Asn Val Gly Arg Asp Ala Phe
 65                  70                  75                  80 aat ttg ttc                                                           249
Asn Leu Phe
```

<210> SEQ ID NO 89
<211> LENGTH: 10
<212> TYPE: PRT
<213> ORGANISM: Neisseria meningitidis

<400> SEQUENCE: 89

```
Thr Glu Gln Pro Gln Val Thr Asn Gly Val
 1               5                  10
```

<210> SEQ ID NO 90
<211> LENGTH: 10
<212> TYPE: PRT
<213> ORGANISM: Neisseria meningitidis

<400> SEQUENCE: 90

```
Glu Gln Pro Gln Val Thr Asn Gly Val Gln
 1               5                  10
```

<210> SEQ ID NO 91
<211> LENGTH: 10
<212> TYPE: PRT
<213> ORGANISM: Neisseria meningitidis

<400> SEQUENCE: 91

```
Gln Pro Gln Val Thr Asn Gly Val Gln Gly
 1               5                  10
```

<210> SEQ ID NO 92
<211> LENGTH: 10
<212> TYPE: PRT
<213> ORGANISM: Neisseria meningitidis

<400> SEQUENCE: 92

```
Pro Gln Val Thr Asn Gly Val Gln Gly Asn
 1               5                  10
```

<210> SEQ ID NO 93
<211> LENGTH: 10
<212> TYPE: PRT
<213> ORGANISM: Neisseria meningitidis

<400> SEQUENCE: 93

```
Gln Val Thr Asn Gly Val Gln Gly Asn Gln
 1               5                  10
```

```
<210> SEQ ID NO 94
<211> LENGTH: 10
<212> TYPE: PRT
<213> ORGANISM: Neisseria meningitidis

<400> SEQUENCE: 94

Val Thr Asn Gly Val Gln Gly Asn Gln Val
1               5                   10

<210> SEQ ID NO 95
<211> LENGTH: 10
<212> TYPE: PRT
<213> ORGANISM: Neisseria meningitidis

<400> SEQUENCE: 95

Thr Asn Gly Val Gln Gly Asn Gln Val Lys
1               5                   10

<210> SEQ ID NO 96
<211> LENGTH: 10
<212> TYPE: PRT
<213> ORGANISM: Neisseria meningitidis

<400> SEQUENCE: 96

Asn Gly Val Gln Gly Asn Gln Val Lys Val
1               5                   10

<210> SEQ ID NO 97
<211> LENGTH: 10
<212> TYPE: PRT
<213> ORGANISM: Neisseria meningitidis

<400> SEQUENCE: 97

Gly Val Gln Gly Asn Gln Val Lys Val Thr
1               5                   10

<210> SEQ ID NO 98
<211> LENGTH: 10
<212> TYPE: PRT
<213> ORGANISM: Neisseria meningitidis

<400> SEQUENCE: 98

Val Gln Gly Asn Gln Val Lys Val Thr Lys
1               5                   10

<210> SEQ ID NO 99
<211> LENGTH: 10
<212> TYPE: PRT
<213> ORGANISM: Neisseria meningitidis

<400> SEQUENCE: 99

Gln Gly Asn Gln Val Lys Val Thr Lys Ala
1               5                   10

<210> SEQ ID NO 100
<211> LENGTH: 10
<212> TYPE: PRT
<213> ORGANISM: Neisseria meningitidis

<400> SEQUENCE: 100

Gly Asn Gln Val Lys Val Thr Lys Ala Lys
1               5                   10

<210> SEQ ID NO 101
<211> LENGTH: 10
```

```
<212> TYPE: PRT
<213> ORGANISM: Neisseria meningitidis

<400> SEQUENCE: 101

Asn Gln Val Lys Val Thr Lys Ala Lys Ser
1               5                   10

<210> SEQ ID NO 102
<211> LENGTH: 10
<212> TYPE: PRT
<213> ORGANISM: Neisseria meningitidis

<400> SEQUENCE: 102

Tyr Lys Pro Ala Tyr Tyr Thr Lys Asp Thr
1               5                   10

<210> SEQ ID NO 103
<211> LENGTH: 10
<212> TYPE: PRT
<213> ORGANISM: Neisseria meningitidis

<400> SEQUENCE: 103

Lys Pro Ala Tyr Tyr Thr Lys Asp Thr Asn
1               5                   10

<210> SEQ ID NO 104
<211> LENGTH: 10
<212> TYPE: PRT
<213> ORGANISM: Neisseria meningitidis

<400> SEQUENCE: 104

Pro Ala Tyr Tyr Thr Lys Asp Thr Asn Asn
1               5                   10

<210> SEQ ID NO 105
<211> LENGTH: 10
<212> TYPE: PRT
<213> ORGANISM: Neisseria meningitidis

<400> SEQUENCE: 105

Ala Tyr Tyr Thr Lys Asp Thr Asn Asn Asn
1               5                   10

<210> SEQ ID NO 106
<211> LENGTH: 10
<212> TYPE: PRT
<213> ORGANISM: Neisseria meningitidis

<400> SEQUENCE: 106

Tyr Tyr Thr Lys Asp Thr Asn Asn Asn Leu
1               5                   10

<210> SEQ ID NO 107
<211> LENGTH: 10
<212> TYPE: PRT
<213> ORGANISM: Neisseria meningitidis

<400> SEQUENCE: 107

Tyr Thr Lys Asp Thr Asn Asn Asn Leu Thr
1               5                   10

<210> SEQ ID NO 108
<211> LENGTH: 10
<212> TYPE: PRT
<213> ORGANISM: Neisseria meningitidis
```

<400> SEQUENCE: 108

Thr Lys Asp Thr Asn Asn Asn Leu Thr Leu
1               5                   10

<210> SEQ ID NO 109
<211> LENGTH: 10
<212> TYPE: PRT
<213> ORGANISM: Neisseria meningitidis

<400> SEQUENCE: 109

Lys Asp Thr Asn Asn Asn Leu Thr Leu Val
1               5                   10

<210> SEQ ID NO 110
<211> LENGTH: 10
<212> TYPE: PRT
<213> ORGANISM: Neisseria meningitidis

<400> SEQUENCE: 110

Asp Thr Asn Asn Asn Leu Thr Leu Val Pro
1               5                   10

<210> SEQ ID NO 111
<211> LENGTH: 10
<212> TYPE: PRT
<213> ORGANISM: Neisseria meningitidis

<400> SEQUENCE: 111

Thr Asn Asn Asn Leu Thr Leu Val Pro Ala
1               5                   10

<210> SEQ ID NO 112
<211> LENGTH: 10
<212> TYPE: PRT
<213> ORGANISM: Neisseria meningitidis

<400> SEQUENCE: 112

Asn Asn Asn Leu Thr Leu Val Pro Ala Val
1               5                   10

<210> SEQ ID NO 113
<211> LENGTH: 10
<212> TYPE: PRT
<213> ORGANISM: Neisseria meningitidis

<400> SEQUENCE: 113

Asn Asn Leu Thr Leu Val Pro Ala Val Val
1               5                   10

<210> SEQ ID NO 114
<211> LENGTH: 10
<212> TYPE: PRT
<213> ORGANISM: Neisseria meningitidis

<400> SEQUENCE: 114

Asn Leu Thr Leu Val Pro Ala Val Val Gly
1               5                   10

<210> SEQ ID NO 115
<211> LENGTH: 10
<212> TYPE: PRT
<213> ORGANISM: Neisseria meningitidis

<400> SEQUENCE: 115

Leu Thr Leu Val Pro Ala Val Val Gly Lys
 1               5                  10

<210> SEQ ID NO 116
<211> LENGTH: 10
<212> TYPE: PRT
<213> ORGANISM: Neisseria meningitidis

<400> SEQUENCE: 116

Thr Glu Ala Gln Ala Ala Asn Gly Gly Ala
 1               5                  10

<210> SEQ ID NO 117
<211> LENGTH: 10
<212> TYPE: PRT
<213> ORGANISM: Neisseria meningitidis

<400> SEQUENCE: 117

Glu Ala Gln Ala Ala Asn Gly Gly Ala Ser
 1               5                  10

<210> SEQ ID NO 118
<211> LENGTH: 10
<212> TYPE: PRT
<213> ORGANISM: Neisseria meningitidis

<400> SEQUENCE: 118

Ala Gln Ala Ala Asn Gly Gly Ala Ser Gly
 1               5                  10

<210> SEQ ID NO 119
<211> LENGTH: 10
<212> TYPE: PRT
<213> ORGANISM: Neisseria meningitidis

<400> SEQUENCE: 119

Gln Ala Ala Asn Gly Gly Ala Ser Gly Gln
 1               5                  10

<210> SEQ ID NO 120
<211> LENGTH: 10
<212> TYPE: PRT
<213> ORGANISM: Neisseria meningitidis

<400> SEQUENCE: 120

Ala Ala Asn Gly Gly Ala Ser Gly Gln Val
 1               5                  10

<210> SEQ ID NO 121
<211> LENGTH: 10
<212> TYPE: PRT
<213> ORGANISM: Neisseria meningitidis

<400> SEQUENCE: 121

Ala Asn Gly Gly Ala Ser Gly Gln Val Lys
 1               5                  10

<210> SEQ ID NO 122
<211> LENGTH: 10
<212> TYPE: PRT
<213> ORGANISM: Neisseria meningitidis

<400> SEQUENCE: 122

Asn Gly Gly Ala Ser Gly Gln Val Lys Val 1               5                   10

<210> SEQ ID NO 123
<211> LENGTH: 10
<212> TYPE: PRT
<213> ORGANISM: Neisseria meningitidis

<400> SEQUENCE: 123

Gly Gly Ala Ser Gly Gln Val Lys Val Thr
1               5                   10

<210> SEQ ID NO 124
<211> LENGTH: 10
<212> TYPE: PRT
<213> ORGANISM: Neisseria meningitidis

<400> SEQUENCE: 124

Gly Ala Ser Gly Gln Val Lys Val Thr Lys
1               5                   10

<210> SEQ ID NO 125
<211> LENGTH: 10
<212> TYPE: PRT
<213> ORGANISM: Neisseria meningitidis

<400> SEQUENCE: 125

Ala Ser Gly Gln Val Lys Val Thr Lys Val
1               5                   10

<210> SEQ ID NO 126
<211> LENGTH: 10
<212> TYPE: PRT
<213> ORGANISM: Neisseria meningitidis

<400> SEQUENCE: 126

Ser Gly Gln Val Lys Val Thr Lys Val Thr
1               5                   10

<210> SEQ ID NO 127
<211> LENGTH: 10
<212> TYPE: PRT
<213> ORGANISM: Neisseria meningitidis

<400> SEQUENCE: 127

Gly Gln Val Lys Val Thr Lys Val Thr Lys
1               5                   10

<210> SEQ ID NO 128
<211> LENGTH: 10
<212> TYPE: PRT
<213> ORGANISM: Neisseria meningitidis

<400> SEQUENCE: 128

Gln Val Lys Val Thr Lys Val Thr Lys Ala
1               5                   10

<210> SEQ ID NO 129
<211> LENGTH: 10
<212> TYPE: PRT
<213> ORGANISM: Neisseria meningitidis

<400> SEQUENCE: 129

Val Lys Val Thr Lys Val Thr Lys Ala Lys
1               5                   10

```
<210> SEQ ID NO 130
<211> LENGTH: 10
<212> TYPE: PRT
<213> ORGANISM: Neisseria meningitidis

<400> SEQUENCE: 130

Lys Val Thr Lys Val Thr Lys Ala Lys Ser
1               5                   10

<210> SEQ ID NO 131
<211> LENGTH: 10
<212> TYPE: PRT
<213> ORGANISM: Neisseria meningitidis

<400> SEQUENCE: 131

Val Thr Lys Val Thr Lys Ala Lys Ser Arg
1               5                   10

<210> SEQ ID NO 132
<211> LENGTH: 10
<212> TYPE: PRT
<213> ORGANISM: Neisseria meningitidis

<400> SEQUENCE: 132

Thr Lys Val Thr Lys Ala Lys Ser Arg Ile
1               5                   10

<210> SEQ ID NO 133
<211> LENGTH: 10
<212> TYPE: PRT
<213> ORGANISM: Neisseria meningitidis

<400> SEQUENCE: 133

Lys Val Thr Lys Ala Lys Ser Arg Ile Arg
1               5                   10

<210> SEQ ID NO 134
<211> LENGTH: 10
<212> TYPE: PRT
<213> ORGANISM: Neisseria meningitidis

<400> SEQUENCE: 134

Ser Ala Tyr Thr Pro Ala Tyr Tyr Thr Lys
1               5                   10

<210> SEQ ID NO 135
<211> LENGTH: 10
<212> TYPE: PRT
<213> ORGANISM: Neisseria meningitidis

<400> SEQUENCE: 135

Ala Tyr Thr Pro Ala Tyr Tyr Thr Lys Asp
1               5                   10

<210> SEQ ID NO 136
<211> LENGTH: 10
<212> TYPE: PRT
<213> ORGANISM: Neisseria meningitidis

<400> SEQUENCE: 136

Tyr Thr Pro Ala Tyr Tyr Thr Lys Asp Thr
1               5                   10

<210> SEQ ID NO 137
```

```
<211> LENGTH: 10
<212> TYPE: PRT
<213> ORGANISM: Neisseria meningitidis

<400> SEQUENCE: 137

Thr Pro Ala Tyr Tyr Thr Lys Asp Thr Asn
1               5                   10

<210> SEQ ID NO 138
<211> LENGTH: 10
<212> TYPE: PRT
<213> ORGANISM: Neisseria meningitidis

<400> SEQUENCE: 138

Pro Ala Tyr Tyr Thr Lys Asp Thr Asn Asn
1               5                   10

<210> SEQ ID NO 139
<211> LENGTH: 10
<212> TYPE: PRT
<213> ORGANISM: Neisseria meningitidis

<400> SEQUENCE: 139

Ala Tyr Tyr Thr Lys Asp Thr Asn Asn Asn
1               5                   10

<210> SEQ ID NO 140
<211> LENGTH: 10
<212> TYPE: PRT
<213> ORGANISM: Neisseria meningitidis

<400> SEQUENCE: 140

Tyr Tyr Thr Lys Asp Thr Asn Asn Asn Leu
1               5                   10

<210> SEQ ID NO 141
<211> LENGTH: 10
<212> TYPE: PRT
<213> ORGANISM: Neisseria meningitidis

<400> SEQUENCE: 141

Tyr Thr Lys Asp Thr Asn Asn Asn Leu Thr
1               5                   10

<210> SEQ ID NO 142
<211> LENGTH: 10
<212> TYPE: PRT
<213> ORGANISM: Neisseria meningitidis

<400> SEQUENCE: 142

Thr Lys Asp Thr Asn Asn Asn Leu Thr Leu
1               5                   10

<210> SEQ ID NO 143
<211> LENGTH: 10
<212> TYPE: PRT
<213> ORGANISM: Neisseria meningitidis

<400> SEQUENCE: 143

Lys Asp Thr Asn Asn Asn Leu Thr Leu Val
1               5                   10

<210> SEQ ID NO 144
<211> LENGTH: 10
<212> TYPE: PRT
```

<213> ORGANISM: Neisseria meningitidis

<400> SEQUENCE: 144

Asp Thr Asn Asn Asn Leu Thr Leu Val Pro
 1               5                   10

<210> SEQ ID NO 145
<211> LENGTH: 10
<212> TYPE: PRT
<213> ORGANISM: Neisseria meningitidis

<400> SEQUENCE: 145

Thr Asn Asn Asn Leu Thr Leu Val Pro Ala
 1               5                   10

<210> SEQ ID NO 146
<211> LENGTH: 10
<212> TYPE: PRT
<213> ORGANISM: Neisseria meningitidis

<400> SEQUENCE: 146

Asn Asn Asn Leu Thr Leu Val Pro Ala Val
 1               5                   10

<210> SEQ ID NO 147
<211> LENGTH: 10
<212> TYPE: PRT
<213> ORGANISM: Neisseria meningitidis

<400> SEQUENCE: 147

Asn Asn Leu Thr Leu Val Pro Ala Val Val
 1               5                   10

<210> SEQ ID NO 148
<211> LENGTH: 10
<212> TYPE: PRT
<213> ORGANISM: Neisseria meningitidis

<400> SEQUENCE: 148

Asn Leu Thr Leu Val Pro Ala Val Val Gly
 1               5                   10

<210> SEQ ID NO 149
<211> LENGTH: 10
<212> TYPE: PRT
<213> ORGANISM: Neisseria meningitidis

<400> SEQUENCE: 149

Leu Thr Leu Val Pro Ala Val Val Gly Lys
 1               5                   10

<210> SEQ ID NO 150
<211> LENGTH: 10
<212> TYPE: PRT
<213> ORGANISM: Neisseria meningitidis

<400> SEQUENCE: 150

Thr Glu Pro Pro Ser Lys Ser Gln Pro Gln
 1               5                   10

<210> SEQ ID NO 151
<211> LENGTH: 10
<212> TYPE: PRT
<213> ORGANISM: Neisseria meningitidis

<400> SEQUENCE: 151

Glu Pro Pro Ser Lys Ser Gln Pro Gln Val
 1               5                  10

<210> SEQ ID NO 152
<211> LENGTH: 10
<212> TYPE: PRT
<213> ORGANISM: Neisseria meningitidis

<400> SEQUENCE: 152

Pro Pro Ser Lys Ser Gln Pro Gln Val Lys
 1               5                  10

<210> SEQ ID NO 153
<211> LENGTH: 10
<212> TYPE: PRT
<213> ORGANISM: Neisseria meningitidis

<400> SEQUENCE: 153

Pro Ser Lys Ser Gln Pro Gln Val Lys Val
 1               5                  10

<210> SEQ ID NO 154
<211> LENGTH: 10
<212> TYPE: PRT
<213> ORGANISM: Neisseria meningitidis

<400> SEQUENCE: 154

Ser Lys Ser Gln Pro Gln Val Lys Val Thr
 1               5                  10

<210> SEQ ID NO 155
<211> LENGTH: 10
<212> TYPE: PRT
<213> ORGANISM: Neisseria meningitidis

<400> SEQUENCE: 155

Lys Ser Gln Pro Gln Val Lys Val Thr Lys
 1               5                  10

<210> SEQ ID NO 156
<211> LENGTH: 10
<212> TYPE: PRT
<213> ORGANISM: Neisseria meningitidis

<400> SEQUENCE: 156

Ser Gln Pro Gln Val Lys Val Thr Lys Ala
 1               5                  10

<210> SEQ ID NO 157
<211> LENGTH: 10
<212> TYPE: PRT
<213> ORGANISM: Neisseria meningitidis

<400> SEQUENCE: 157

Gln Pro Gln Val Lys Val Thr Lys Ala Lys
 1               5                  10

<210> SEQ ID NO 158
<211> LENGTH: 10
<212> TYPE: PRT
<213> ORGANISM: Neisseria meningitidis

<400> SEQUENCE: 158

```
Pro Gln Val Lys Val Thr Lys Ala Lys Ser
1               5                   10
```

<210> SEQ ID NO 159
<211> LENGTH: 10
<212> TYPE: PRT
<213> ORGANISM: Neisseria meningitidis

<400> SEQUENCE: 159

```
Gln Val Lys Val Thr Lys Ala Lys Ser Arg
1               5                   10
```

<210> SEQ ID NO 160
<211> LENGTH: 10
<212> TYPE: PRT
<213> ORGANISM: Neisseria meningitidis

<400> SEQUENCE: 160

```
Val Lys Val Thr Lys Ala Lys Ser Arg Ile
1               5                   10
```

<210> SEQ ID NO 161
<211> LENGTH: 10
<212> TYPE: PRT
<213> ORGANISM: Neisseria meningitidis

<400> SEQUENCE: 161

```
Lys Val Thr Lys Ala Lys Ser Arg Ile Arg
1               5                   10
```

<210> SEQ ID NO 162
<211> LENGTH: 10
<212> TYPE: PRT
<213> ORGANISM: Neisseria meningitidis

<400> SEQUENCE: 162

```
Asn Ser Lys Ser Ala Tyr Thr Pro Ala His
1               5                   10
```

<210> SEQ ID NO 163
<211> LENGTH: 10
<212> TYPE: PRT
<213> ORGANISM: Neisseria meningitidis

<400> SEQUENCE: 163

```
Ser Lys Ser Ala Tyr Thr Pro Ala His Tyr
1               5                   10
```

<210> SEQ ID NO 164
<211> LENGTH: 10
<212> TYPE: PRT
<213> ORGANISM: Neisseria meningitidis

<400> SEQUENCE: 164

```
Lys Ser Ala Tyr Thr Pro Ala His Tyr Thr
1               5                   10
```

<210> SEQ ID NO 165
<211> LENGTH: 10
<212> TYPE: PRT
<213> ORGANISM: Neisseria meningitidis

<400> SEQUENCE: 165

```
Ser Ala Tyr Thr Pro Ala His Tyr Thr Arg
1               5                   10
```

```
<210> SEQ ID NO 166
<211> LENGTH: 10
<212> TYPE: PRT
<213> ORGANISM: Neisseria meningitidis

<400> SEQUENCE: 166

Ala Tyr Thr Pro Ala His Tyr Thr Arg Gln
 1               5                  10

<210> SEQ ID NO 167
<211> LENGTH: 10
<212> TYPE: PRT
<213> ORGANISM: Neisseria meningitidis

<400> SEQUENCE: 167

Tyr Thr Pro Ala His Tyr Thr Arg Gln Asn
 1               5                  10

<210> SEQ ID NO 168
<211> LENGTH: 10
<212> TYPE: PRT
<213> ORGANISM: Neisseria meningitidis

<400> SEQUENCE: 168

Thr Pro Ala His Tyr Thr Arg Gln Asn Asn
 1               5                  10

<210> SEQ ID NO 169
<211> LENGTH: 10
<212> TYPE: PRT
<213> ORGANISM: Neisseria meningitidis

<400> SEQUENCE: 169

Pro Ala His Tyr Thr Arg Gln Asn Asn Thr
 1               5                  10

<210> SEQ ID NO 170
<211> LENGTH: 10
<212> TYPE: PRT
<213> ORGANISM: Neisseria meningitidis

<400> SEQUENCE: 170

Ala His Tyr Thr Arg Gln Asn Asn Thr Asp
 1               5                  10

<210> SEQ ID NO 171
<211> LENGTH: 10
<212> TYPE: PRT
<213> ORGANISM: Neisseria meningitidis

<400> SEQUENCE: 171

His Tyr Thr Arg Gln Asn Asn Thr Asp Val
 1               5                  10

<210> SEQ ID NO 172
<211> LENGTH: 10
<212> TYPE: PRT
<213> ORGANISM: Neisseria meningitidis

<400> SEQUENCE: 172

Tyr Thr Arg Gln Asn Asn Thr Asp Val Phe
 1               5                  10
```

```
<210> SEQ ID NO 173
<211> LENGTH: 10
<212> TYPE: PRT
<213> ORGANISM: Neisseria meningitidis

<400> SEQUENCE: 173

Thr Arg Gln Asn Asn Thr Asp Val Phe Val
 1               5                  10

<210> SEQ ID NO 174
<211> LENGTH: 10
<212> TYPE: PRT
<213> ORGANISM: Neisseria meningitidis

<400> SEQUENCE: 174

Arg Gln Asn Asn Thr Asp Val Phe Val Pro
 1               5                  10

<210> SEQ ID NO 175
<211> LENGTH: 10
<212> TYPE: PRT
<213> ORGANISM: Neisseria meningitidis

<400> SEQUENCE: 175

Gln Asn Asn Thr Asp Val Phe Val Pro Ala
 1               5                  10

<210> SEQ ID NO 176
<211> LENGTH: 10
<212> TYPE: PRT
<213> ORGANISM: Neisseria meningitidis

<400> SEQUENCE: 176

Asn Asn Thr Asp Val Phe Val Pro Ala Val
 1               5                  10

<210> SEQ ID NO 177
<211> LENGTH: 10
<212> TYPE: PRT
<213> ORGANISM: Neisseria meningitidis

<400> SEQUENCE: 177

Asn Thr Asp Val Phe Val Pro Ala Val Val
 1               5                  10

<210> SEQ ID NO 178
<211> LENGTH: 10
<212> TYPE: PRT
<213> ORGANISM: Neisseria meningitidis

<400> SEQUENCE: 178

Thr Asp Val Phe Val Pro Ala Val Val Gly
 1               5                  10

<210> SEQ ID NO 179
<211> LENGTH: 10
<212> TYPE: PRT
<213> ORGANISM: Neisseria meningitidis

<400> SEQUENCE: 179

Asp Val Phe Val Pro Ala Val Val Gly Lys
 1               5                  10

<210> SEQ ID NO 180
<211> LENGTH: 10
```

```
<212> TYPE: PRT
<213> ORGANISM: Neisseria meningitidis

<400> SEQUENCE: 180

Val Phe Val Pro Ala Val Val Gly Lys Pro
 1               5                   10

<210> SEQ ID NO 181
<211> LENGTH: 10
<212> TYPE: PRT
<213> ORGANISM: Neisseria meningitidis

<400> SEQUENCE: 181

Phe Val Pro Ala Val Val Gly Lys Pro Gly
 1               5                   10

<210> SEQ ID NO 182
<211> LENGTH: 18
<212> TYPE: DNA
<213> ORGANISM: Artificial Sequence
<220> FEATURE:
<223> OTHER INFORMATION: linker insertion
<220> FEATURE:
<221> NAME/KEY: CDS
<222> LOCATION: (1)...(18)

<400> SEQUENCE: 182 gat atc atc gat gga ttc                                         18
Asp Ile Ile Asp Gly Phe
 1               5

<210> SEQ ID NO 183
<211> LENGTH: 36
<212> TYPE: DNA
<213> ORGANISM: Artificial Sequence
<220> FEATURE:
<223> OTHER INFORMATION: linker insertion
<220> FEATURE:
<221> NAME/KEY: CDS
<222> LOCATION: (3)...(35)

<400> SEQUENCE: 183 ga tca gct gct aac ggt ggt gct tca ggt cag gtt g                36
   Ser Ala Ala Asn Gly Gly Ala Ser Gly Gln Val
    1               5                   10

<210> SEQ ID NO 184
<211> LENGTH: 36
<212> TYPE: DNA
<213> ORGANISM: Artificial Sequence
<220> FEATURE:
<223> OTHER INFORMATION: linker insertion

<400> SEQUENCE: 184
gatccaacct gacctgaagc accaccgtta gcagct                         36

<210> SEQ ID NO 185
<211> LENGTH: 14
<212> TYPE: PRT
<213> ORGANISM: Artificial Sequence
<220> FEATURE:
<223> OTHER INFORMATION: peptide linker

<400> SEQUENCE: 185

Gly Ser Ala Ala Asn Gly Gly Ala Ser Gly Gln Val Gly Ser
 1               5                   10
```

```
<210> SEQ ID NO 186
<211> LENGTH: 36
<212> TYPE: DNA
<213> ORGANISM: Artificial Sequence
<220> FEATURE:
<223> OTHER INFORMATION: linker insertion
<220> FEATURE:
<221> NAME/KEY: CDS
<222> LOCATION: (3)...(35)

<400> SEQUENCE: 186 ga tca acc aaa gac acc aat aac aac ctc acc cta g         36
   Ser Thr Lys Asp Thr Asn Asn Asn Leu Thr Leu
    1               5                  10

<210> SEQ ID NO 187
<211> LENGTH: 36
<212> TYPE: DNA
<213> ORGANISM: Artificial Sequence
<220> FEATURE:
<223> OTHER INFORMATION: linker insertion

<400> SEQUENCE: 187
gatcctaggg tgaggttgtt attggtgtct ttggtt                  36

<210> SEQ ID NO 188
<211> LENGTH: 14
<212> TYPE: PRT
<213> ORGANISM: Artificial Sequence
<220> FEATURE:
<223> OTHER INFORMATION: peptide linker

<400> SEQUENCE: 188

Gly Ser Thr Lys Asp Thr Asn Asn Asn Leu Thr Leu Gly Ser
 1               5                  10

<210> SEQ ID NO 189
<211> LENGTH: 12
<212> TYPE: PRT
<213> ORGANISM: Neisseria meningitidis

<400> SEQUENCE: 189

Tyr Tyr Thr Lys Asp Thr Asn Asn Leu Thr Leu
 1               5                  10

<210> SEQ ID NO 190
<211> LENGTH: 12
<212> TYPE: PRT
<213> ORGANISM: Neisseria meningitidis

<400> SEQUENCE: 190

Tyr Tyr Thr Lys Asn Thr Asn Asn Asn Leu Thr Leu
 1               5                  10

<210> SEQ ID NO 191
<211> LENGTH: 393
<212> TYPE: PRT
<213> ORGANISM: Neisseria meningitidis

<400> SEQUENCE: 191

Met Arg Lys Lys Leu Thr Ala Leu Val Leu Ser Ala Leu Pro Leu Ala
 1               5                  10                  15

Ala Val Ala Asp Val Ser Leu Tyr Gly Glu Ile Lys Ala Gly Val Glu
                20                  25                  30

Gly Arg Asn Ile Gln Ala Gln Leu Thr Glu Gln Pro Gln Val Thr Asn
            35                  40                  45
```

```
Gly Val Gln Gly Asn Gln Val Lys Val Thr Lys Ala Lys Ser Arg Ile
 50                  55                  60

Arg Thr Lys Ile Ser Asp Phe Gly Ser Phe Ile Gly Phe Lys Gly Ser
 65                  70                  75                  80

Glu Asp Leu Gly Glu Gly Leu Lys Ala Val Trp Gln Leu Glu Gln Asp
                 85                  90                  95

Val Ser Val Ala Gly Gly Ala Ser Gln Trp Gly Asn Arg Glu Ser
            100                 105                 110

Phe Ile Gly Leu Ala Gly Glu Phe Gly Thr Leu Arg Ala Gly Arg Val
            115                 120                 125

Ala Asn Gln Phe Asp Asp Ala Ser Gln Ala Ile Asn Pro Trp Asp Ser
        130                 135                 140

Asn Asn Asp Val Ala Ser Gln Leu Gly Ile Phe Lys Arg His Asp Asp
145                 150                 155                 160

Met Pro Val Ser Val Arg Tyr Asp Ser Pro Glu Phe Ser Gly Phe Ser
                165                 170                 175

Gly Ser Val Gln Phe Val Pro Ala Gln Asn Ser Lys Ser Ala Tyr Lys
            180                 185                 190

Pro Ala Tyr Tyr Thr Lys Asp Thr Asn Asn Asn Leu Thr Leu Val Pro
        195                 200                 205

Ala Val Val Gly Lys Pro Gly Ser Asp Val Tyr Ala Gly Leu Asn
210                 215                 220

Tyr Lys Asn Gly Gly Phe Ala Gly Asn Tyr Ala Phe Lys Tyr Ala Arg
225                 230                 235                 240

His Ala Asn Val Gly Arg Asn Ala Phe Glu Leu Phe Leu Ile Gly Ser
                245                 250                 255

Ala Thr Ser Asp Glu Ala Lys Gly Thr Asp Pro Leu Lys Asn His Gln
            260                 265                 270

Val His Arg Leu Thr Gly Gly Tyr Glu Glu Gly Gly Leu Asn Leu Ala
        275                 280                 285

Leu Ala Ala Gln Leu Asp Leu Ser Glu Asn Gly Asp Lys Ala Lys Thr
290                 295                 300

Lys Asn Ser Thr Thr Glu Ile Ala Ala Thr Ala Ser Tyr Arg Phe Gly
305                 310                 315                 320

Asn Ala Val Pro Arg Ile Ser Tyr Ala His Gly Phe Asp Leu Ile Glu
                325                 330                 335

Arg Gly Lys Lys Gly Glu Asn Thr Ser Tyr Asp Gln Ile Ile Ala Gly
            340                 345                 350

Val Asp Tyr Asp Phe Ser Lys Arg Thr Ser Ala Ile Val Ser Gly Ala
        355                 360                 365

Trp Leu Lys Arg Asn Thr Gly Ile Gly Asn Tyr Thr Gln Ile Asn Ala
370                 375                 380

Ala Ser Val Gly Leu Arg His Lys Phe
385                 390

<210> SEQ ID NO 192
<211> LENGTH: 6
<212> TYPE: PRT
<213> ORGANISM: Artificial Sequence
<220> FEATURE:
<223> OTHER INFORMATION: linker peptide

<400> SEQUENCE: 192

Asp Ile Ile Asp Gly Ser
 1               5
```

```
<210> SEQ ID NO 193
<211> LENGTH: 4
<212> TYPE: PRT
<213> ORGANISM: Neisseria meningitidis

<400> SEQUENCE: 193

Gly Arg Asn Ile
1
```

RECOMBINANT MICROORGANISM EXPRESSING MENINGOCOCCAL CLASS 1 OUTER MEMBRANE PROTEIN

This application is Divisional of application Ser. No. 08/204,808, filed Feb. 15, 1994, now U.S. Pat. No. 7,118, 757, which if a file-wrapper continuation of application Ser. No. 07/691,005, filed Aug. 22, 1991, now abandoned, which is the national phase 371 application of PCT/US89/05678, filed Dec. 19, 1989, which claims foreign priority to the Netherlands patent applications 8803111, filed Dec. 19, 1998; 8900036 filed Jan. 6, 1989; and 8901612, filed Jun. 26, 1989.

BACKGROUND OF THE INVENTION

Bacterial meningitis is an inflammatory disease of the central nervous system caused by the growth of bacteria in and adjacent to the leptomeninges. Meningitis is an acute infectious disease which affects children and young adults and is caused by the *Neisseria meningitidis*, amongst other agents including other bacterial and viral pathogens.

Meningococci are subdivided into serological groups depending on the presence of either capsular or cell wall antigens. Currently recognized sero-groups include A, B, C, D, W-135, X, Y, Z, and 29E as segregated by seroagglutination. The polysaccharides responsible for the serogroup specificity of the group A, B, C, X, W-135 and Y have been purified.

The carrier rate for meningococci is much higher than the incidence of the disease. Some persons are temporary carriers, while others are chronic carriers, discharging meningococci either more or less continuously or in a sporadic fashion. The meningococcal carrier state is an immunizing process, and within two weeks of colonization, production of antibodies to meningococci can be identified. It appears that bactericidal antibodies are directed against both the capsular polysaccharide and other cell wall antigens.

Studies have shown that meningococcal outer membranes have three to five major proteins, with the predominant 41,000 Mr or 38,000 Mr proteins carrying the serotype specific determinants. There is a considerable degree of interstrain heterogeneity in the profiles of the outer membrane proteins on sodium dodecyl sulfate-polyacrylamide electrophoretic gels (SDS-PAGE). As defined by peptide mapping studies, the proteins comprise five classes, designated 1 through 5, based upon common peptide structures. Bactericidal monoclonal antibodies have been produced against the 46,000 Mr Class 1 proteins which are shared to some extent among strains of different serotypes. (Frasch, C. E. et al., (1985) pg. 633, "New Developments in Meningococcal Vaccines", in G. K. Schoolnik et al. (ed.) *The Pathogenic Nisseriae,* American Society for Microbiology, Washington, D.C.).

The capsular polysaccharide of groups A, C, W-135 and Y meningococci have been used to develop vaccines against the organism. Although these vaccines have been effective in the short term, they do not induce immunological memory and subjects must be revaccinated within approximately 3 years to maintain their resistance. The group B polysaccharide is poorly immunogenic and successful vaccines have not been produced. A possible explanation for the low activity may be due to tolerance to the group B polysaccharide induced by crossreactive antigens found in human tissues such as the brain. Furthermore, studies show that most of the bactericidal antibodies in the convelescent sera of patients who have had group B meningococcal disease are directed against outer membrane proteins.

Vaccines for protecting against group B meningococcal disease have been developed in which non-covalent complexes of outer membrane proteins (OMP) and group B polysaccharide were administered. Beuvery, et al. (1983) *Infect. Immun.* 40:369–380. However, the B polysaccharide is known to induce a transient IgM antibody response, which does not confer immunoprotection. Furthermore, there is great antigenic diversity and variability in the meningoococci outer membrane proteins from strain to strain. Additionally, lipopolysaccharides are present in the OMP and exhibit antigenic variability as well.

There is a need for safe and effective vaccines against meningococcal disease which provide immunity from infection, particularly in infants and the elderly.

SUMMARY OF THE INVENTION

This invention pertains to isolated outer membrane vesicles (OMV's), to substantially purified Class 1 outer membrane protein (OMP) of *Neisseria meningitidis,* to fragments of the Class 1 OMP and to oligopeptides derived from the Class 1 OMP which contain continuous or discontinuous, immunogenic and protective B cell epitopes reactive with bactericidal antibodies against *N. meningitidis* and to the use of isolated OMV's, the meningococcal Class 1 OMP, fragments or oligopeptides for vaccination against *N. meningitidis.*

The isolated OMV's, meningococcal Class 1 OMP, fragments or oligopeptides derived therefrom can be used in univalent or multivalent subunit vaccines alone, in mixtures, or as chemical conjugates or genetic fusions. In preferred vaccines, epitopes from different epidemiologically relevant meningococcal strains are used. In addition, isolated OMV's, the Class 1 OMP, fragments or oligopeptides can be used in conjunction (as mixtures, fusion or conjugates) with other antigens of *N. meningitidis.* For example, they can be used in conjunction with capsular polymers or oligomers (or fragments thereof) of *N. meningitidis* or with Class 1 outer membrane proteins (or epitopes thereof) of different subtypes. In addition, they can be used with antigens of other infectious bacteria, viruses, fungi or parasites. Class 1 OMP T cell epitopes also are defined and these can be used in conjunction with other vaccine components to enhance the protective immune response to the vaccines.

This invention also pertains to the methods of producing isolated OMV's, the Class 1 OMP, fragments and oligopeptides and to various vaccine formulations containing them. The isolated OMV's Class 1 OMP can be produced by mutant meningococcal strains which do not express the Class 2/3 outer membrane protein. Fragments can be produced by cyanogen bromide cleavage and subsequent purification. Isolated OMV's, the Class 1 OMP, fragments or oligopeptides can be produced by recombinant DNA techniques, chemical synthesis or chemical or enzymatic cleavage. These materials, in turn, can be conjugated or fused to carrier peptides or proteins, to other antigens of *N. meningitidis* or to antigens of other microorganisms by chemical or genetic coupling technique to produce multivalent antigenic conjugates and fusion peptides or proteins. They can be modified for conjugation such as by the addition of amino acids of other coupling groups. For vaccination, isolated OMV's, the Class 1 OMP, fragments or oligopeptides, in any of the forms described, can be formulated in pharmaceutically acceptable vehicles with optional additives such as adjuvants.

This invention also pertains to isolated nucleic acids which encode class 1 OMP, fragments or oligopeptides. The nucleic acids can be incorporated into appropriate expression systems for production of isolated OMV's, Class 1 OMP, fragments or any oligopeptides derived therefrom. These nucleic acids can be modified as genetic fusions to contain sequences encoding additional polypeptides useful in enhancing the immune response to the vaccine formulation containing the expressed fusion polypeptides. In addition, Class 1 OMP of N. meningitidis is homologous in amino acid sequence and structure to porin proteins of other gram negative pathogens and thus the Class 1 OMP, fragments and oligopeptides of this invention allow for the development of vaccines for other gram negative pathogens.

BRIEF DESCRIPTION OF THE FIGURES

FIG. 1. Scheme for amplification of genes encoding meningococcal Class 1 outer membrane protein by PCR (Polymerase Chain Reaction).

FIG. 2. (see also SEQ ID NOs 61–74) 5' gene sequences encoding VR1 (first variable region) of Class 1 outer membrane proteins of several N. meningitidis subtypes. Also shown are the amino acid translations of the gene sequences.

Figure 3C:
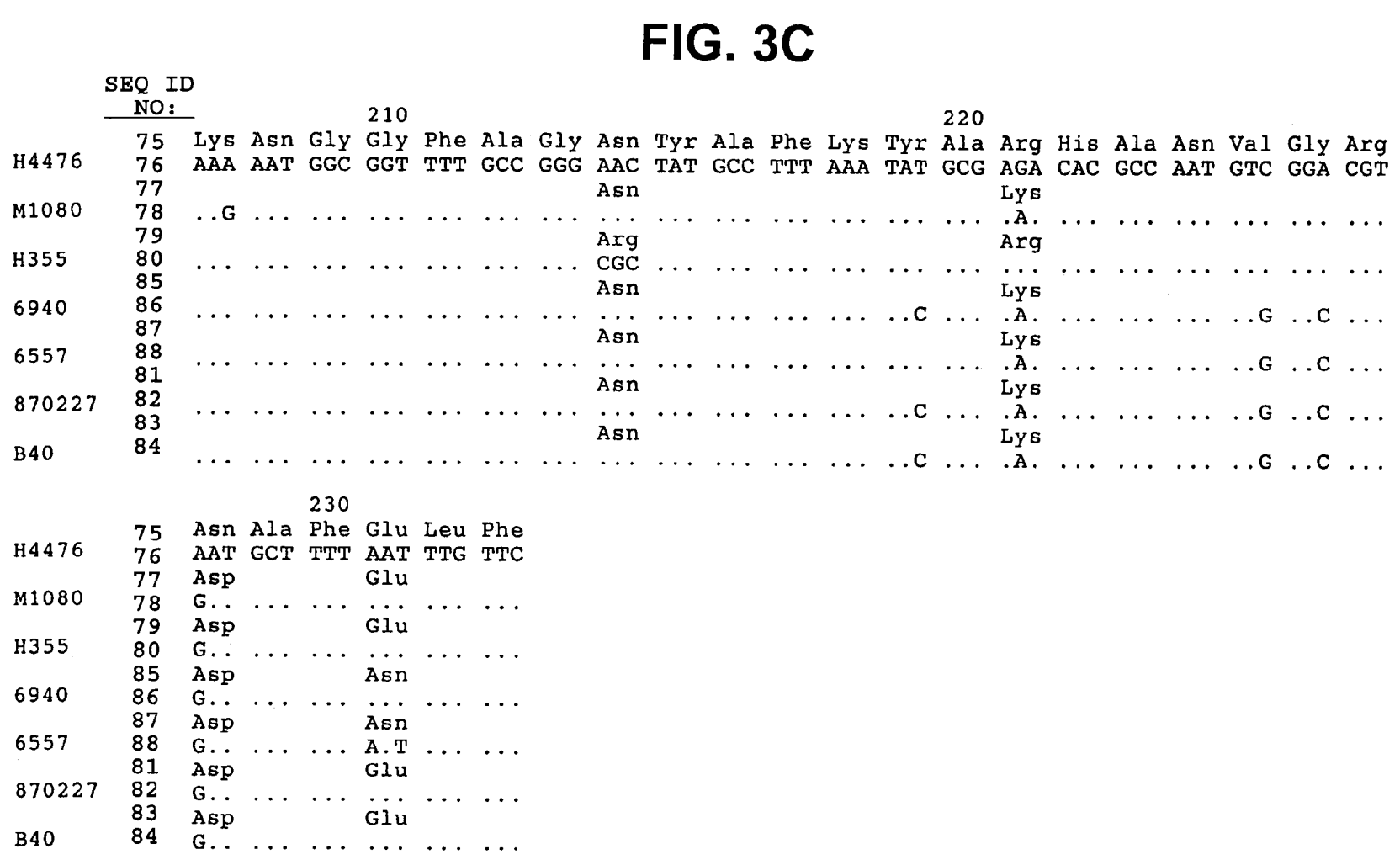

FIGS. 3A, 3B and 3C (see also SEQ ID NOs 75–84) 3' gene sequences encoding VR2 (second variable region) of Class 1 outer membrane proteins of several N. meningitidis subtypes. Also shown are the amino acid translations of the gene sequences.

FIGS. 4a, 4b, 4c, 4d, 4e, 4f, 4g and 4h. Epitope scanning by reaction of monoclonal antibodies with solid phase decapeptides spanning the predicted amino acid sequences of Class 1 proteins from strains P1.7,16, P1.16 and P1.15. Adjacent decapeptides differ by five amino residues. Annotations show the strain from which the sequence was derived, the mAb used and its subtype specificity.

FIG. 11. (see also SEQ ID NO:5) Putative conformation of N. meningitidis Class 1 OMP subtype P1.16.

DETAILED DESCRIPTION OF THE INVENTION

Figure 5A:
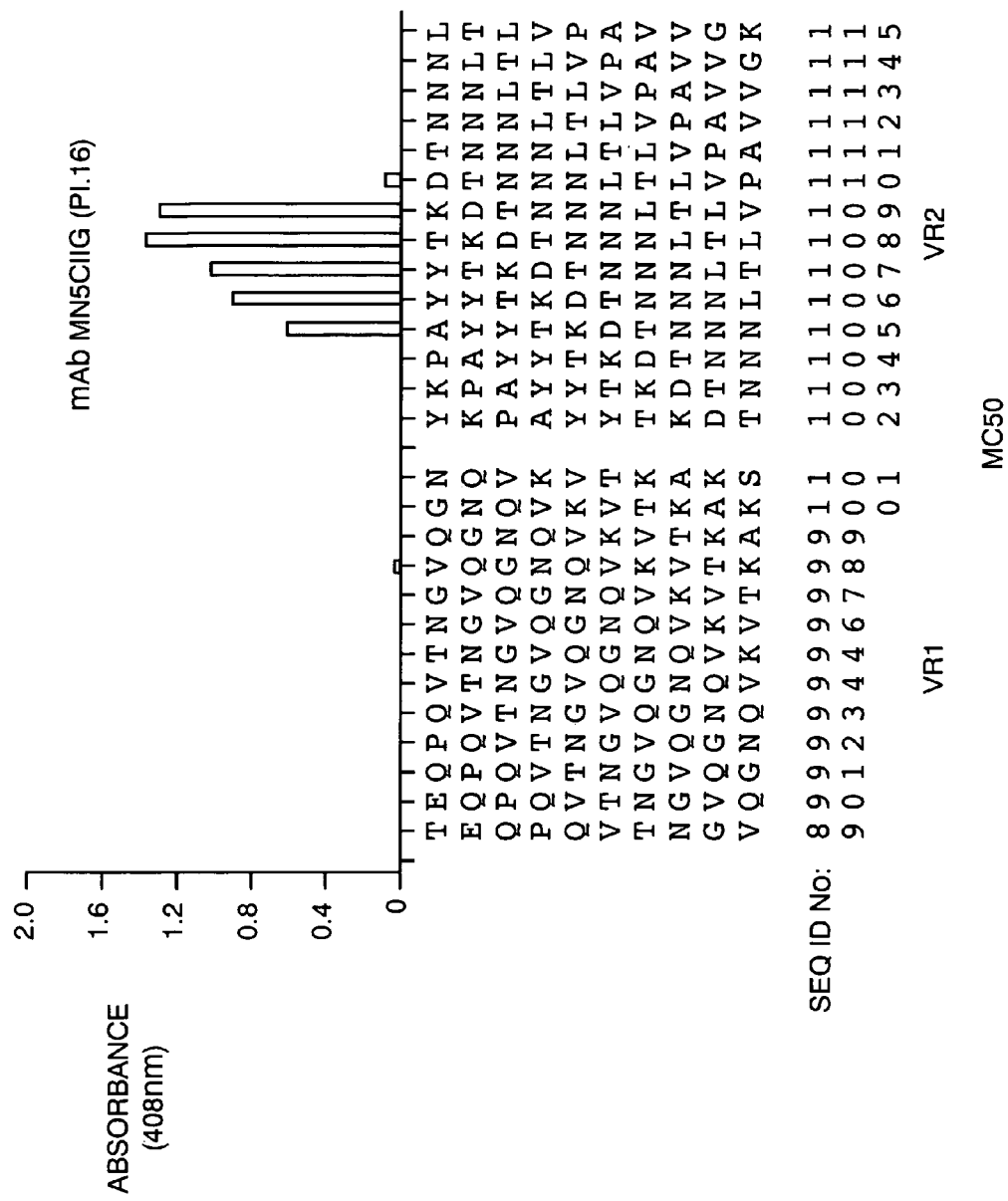
FIGS. 5a, 5b, 5c, 5d, 5e, 5f, 5g and 5h (see also SEQ ID NOs 89 181). Reaction of the monoclonal antibodies with series of overlapping decapeptides corresponding to variable regions VR1 and VR2, with adjacent peptides differing by a single amino acid residue. Annotations show the strain from which the sequence was derived, the mAb used and its subtype specificity.
Figure 5B:
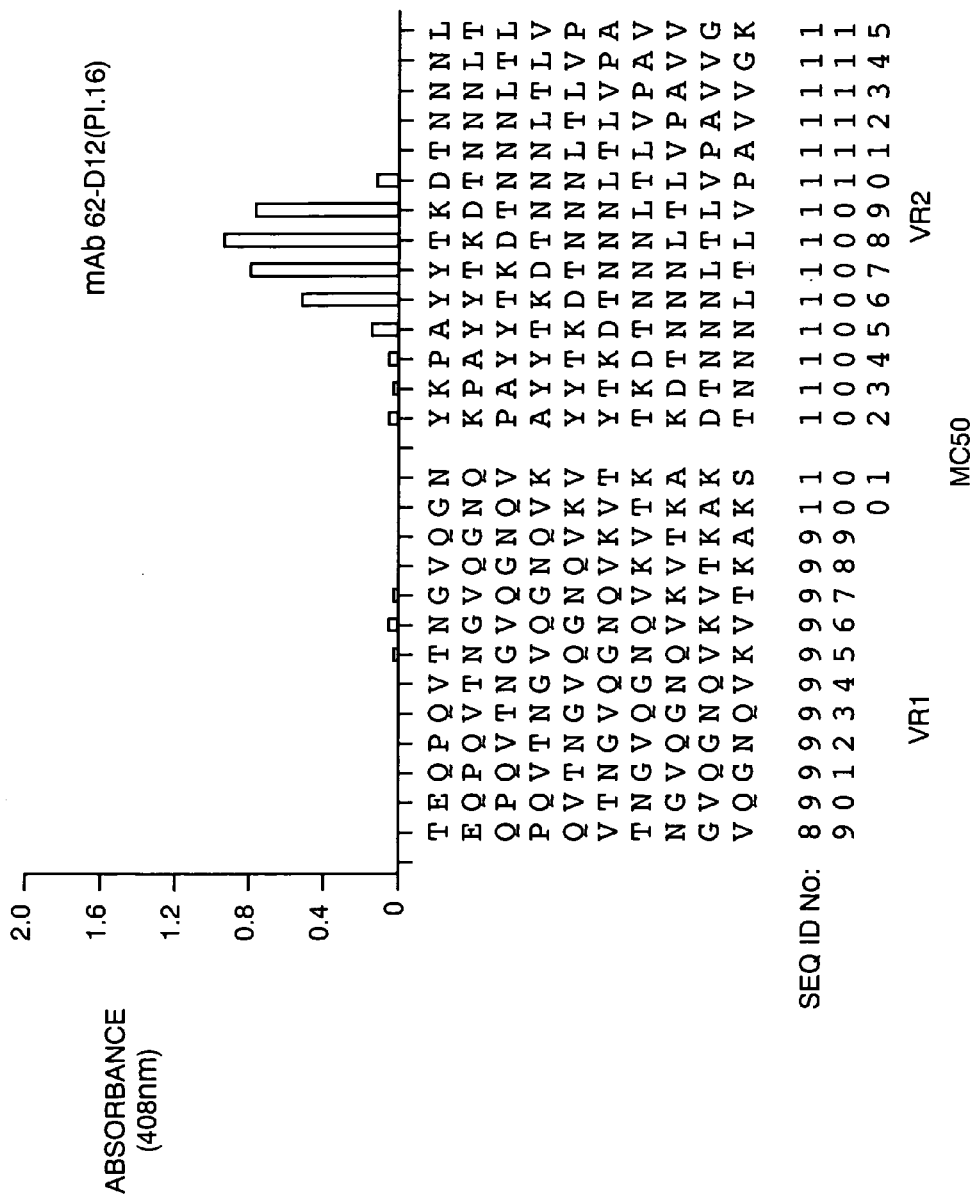
Figure 5C:
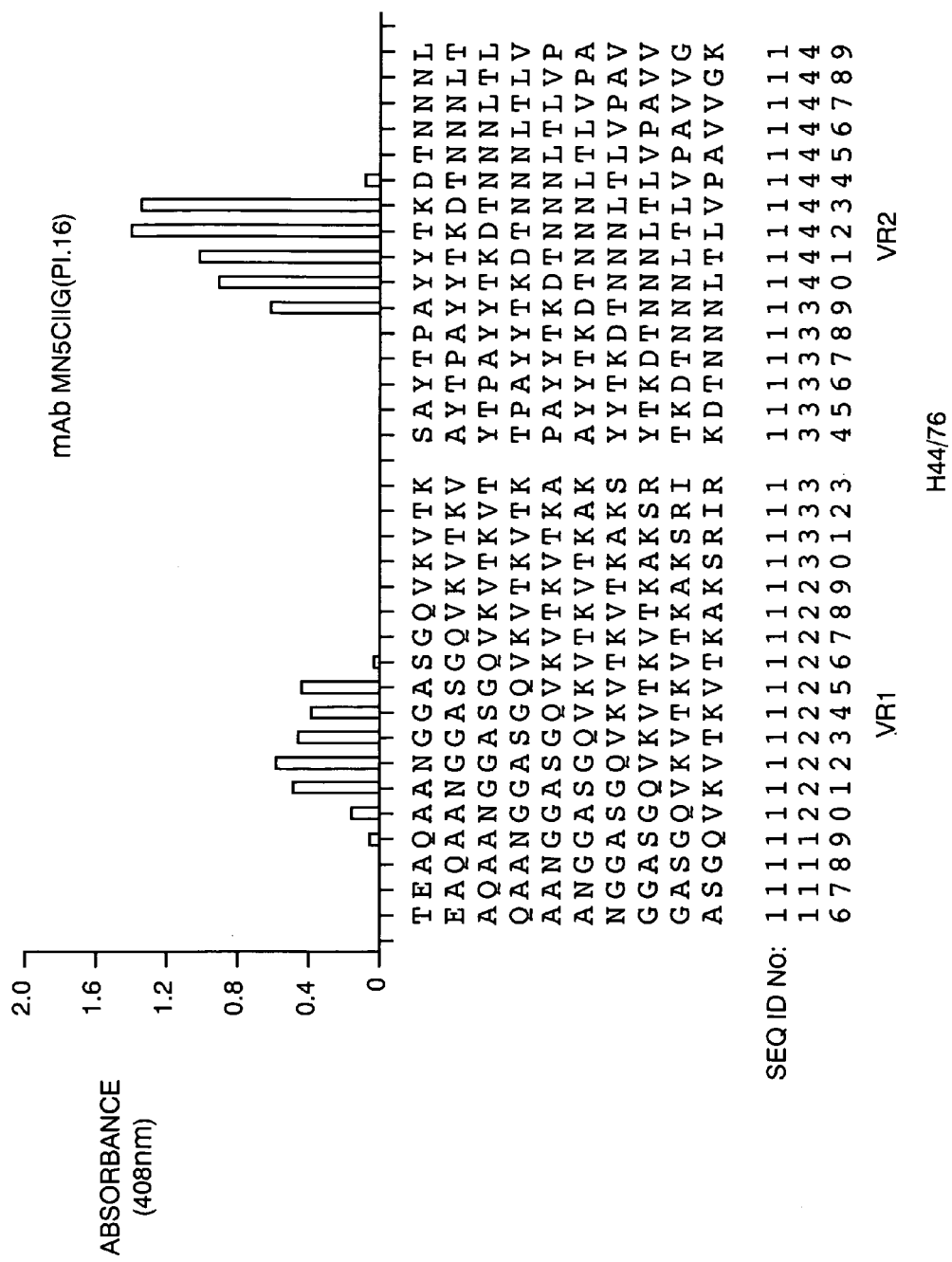
Figure 5D:
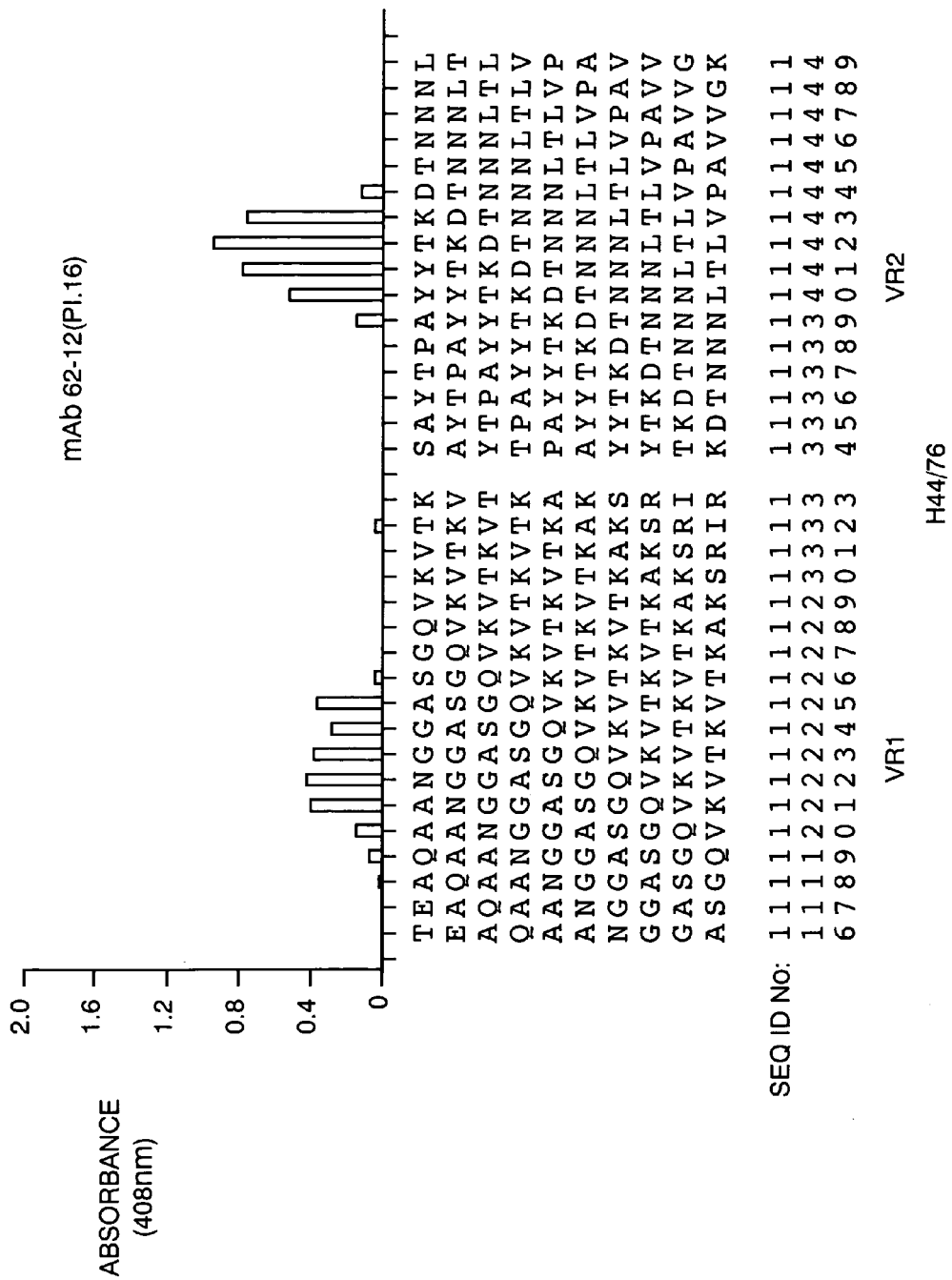
Figure 5E:
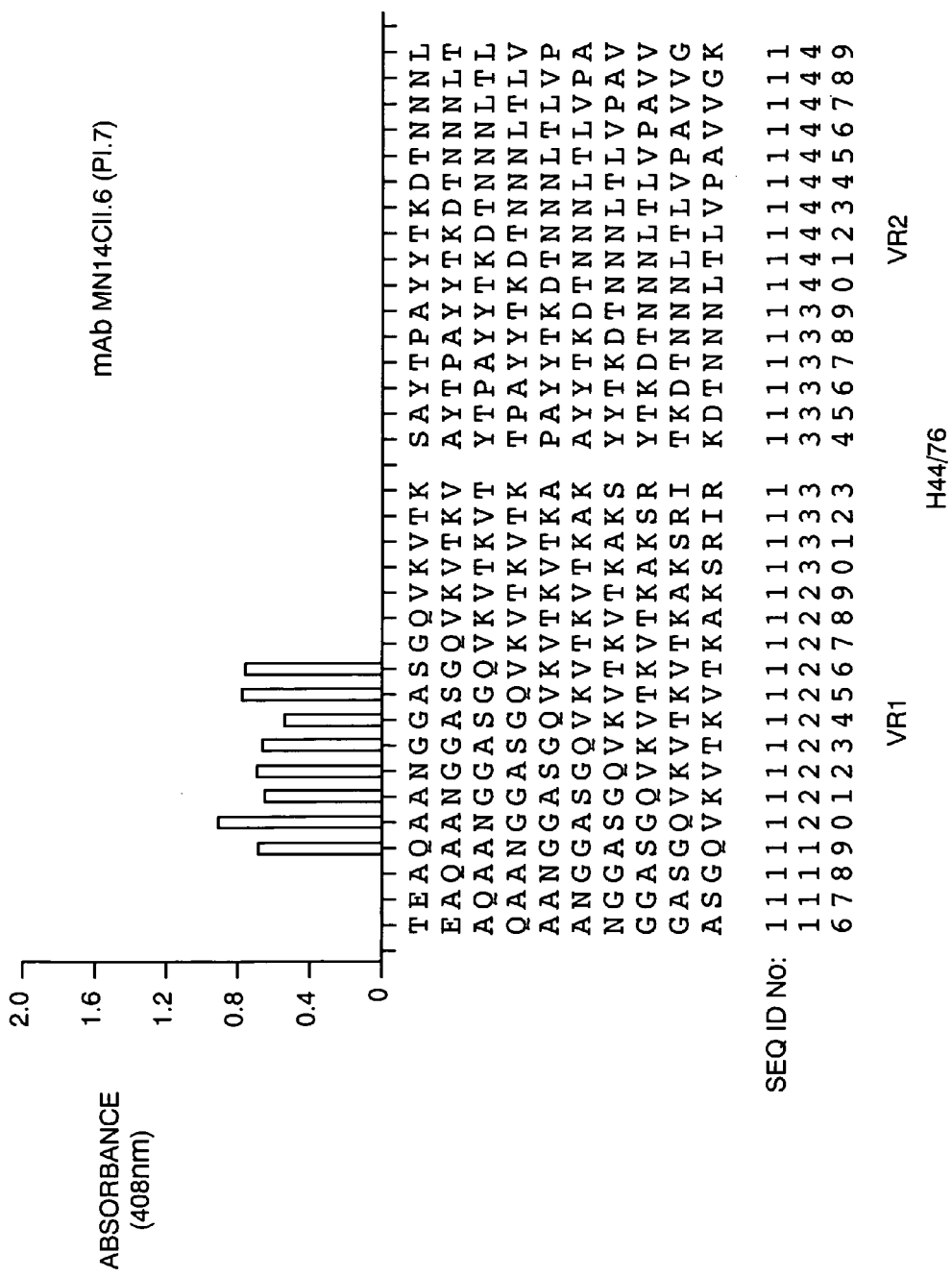
Figure 5F:
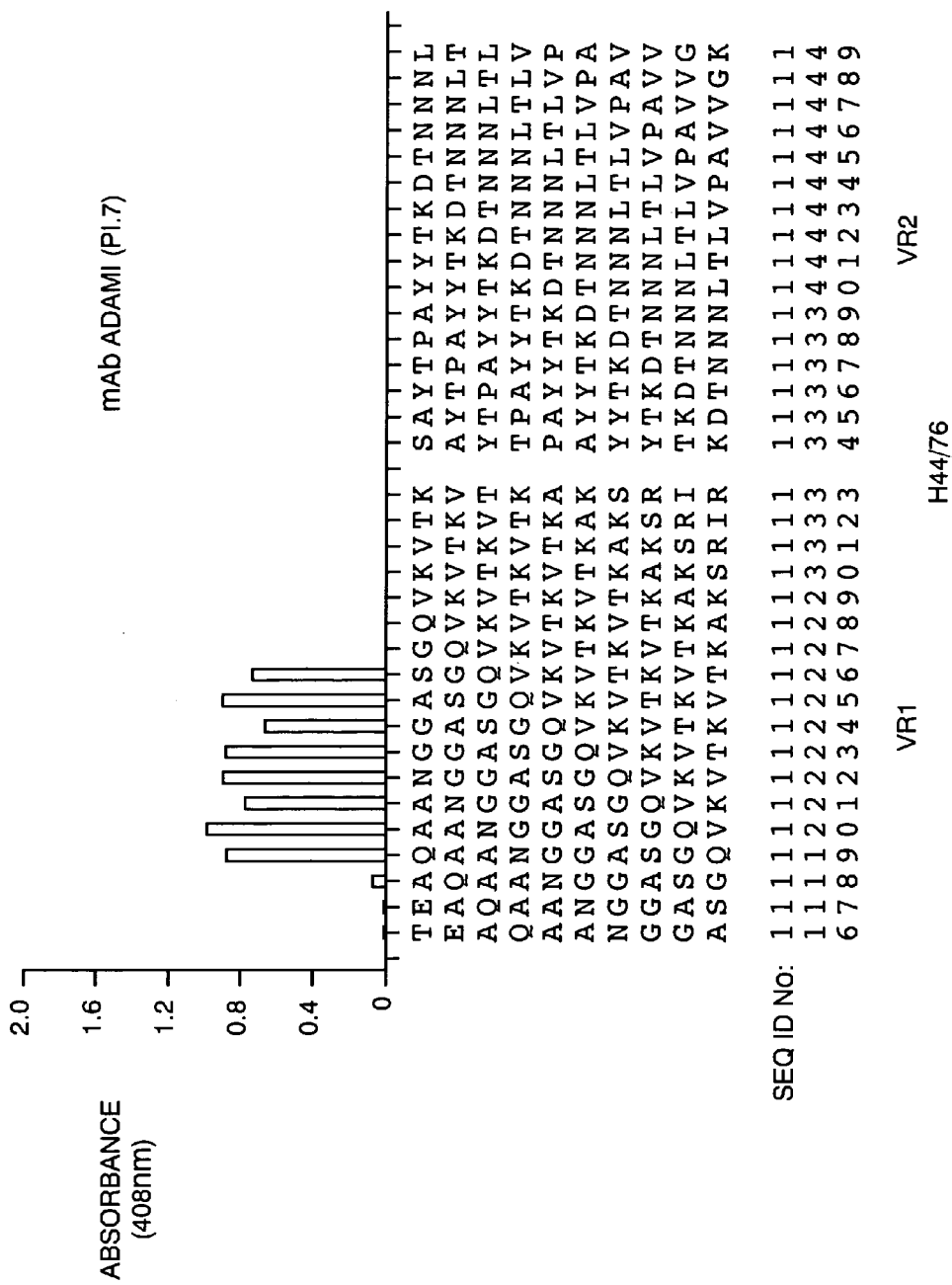
Figure 5G:
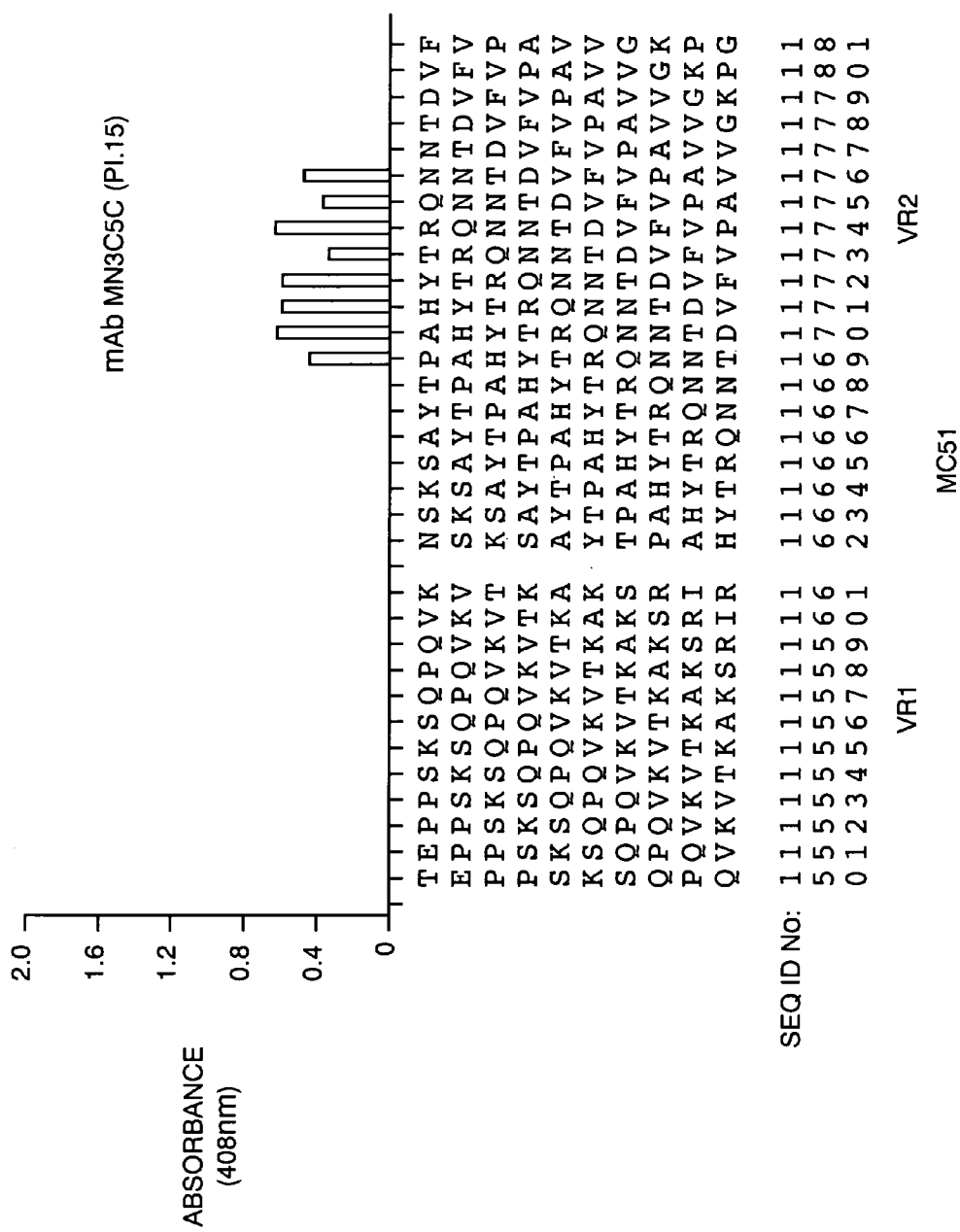
Figure 5H:
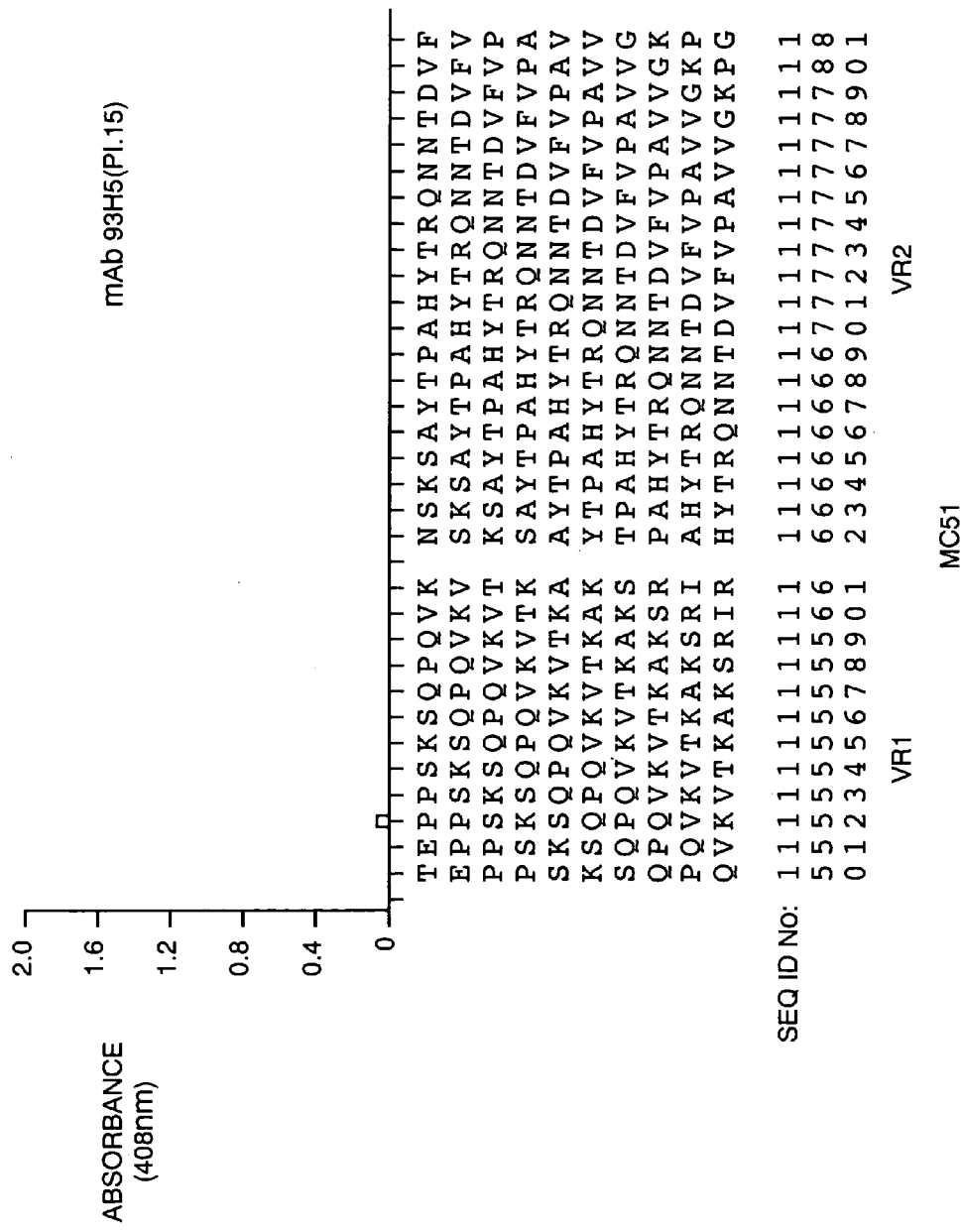
Figure 6:
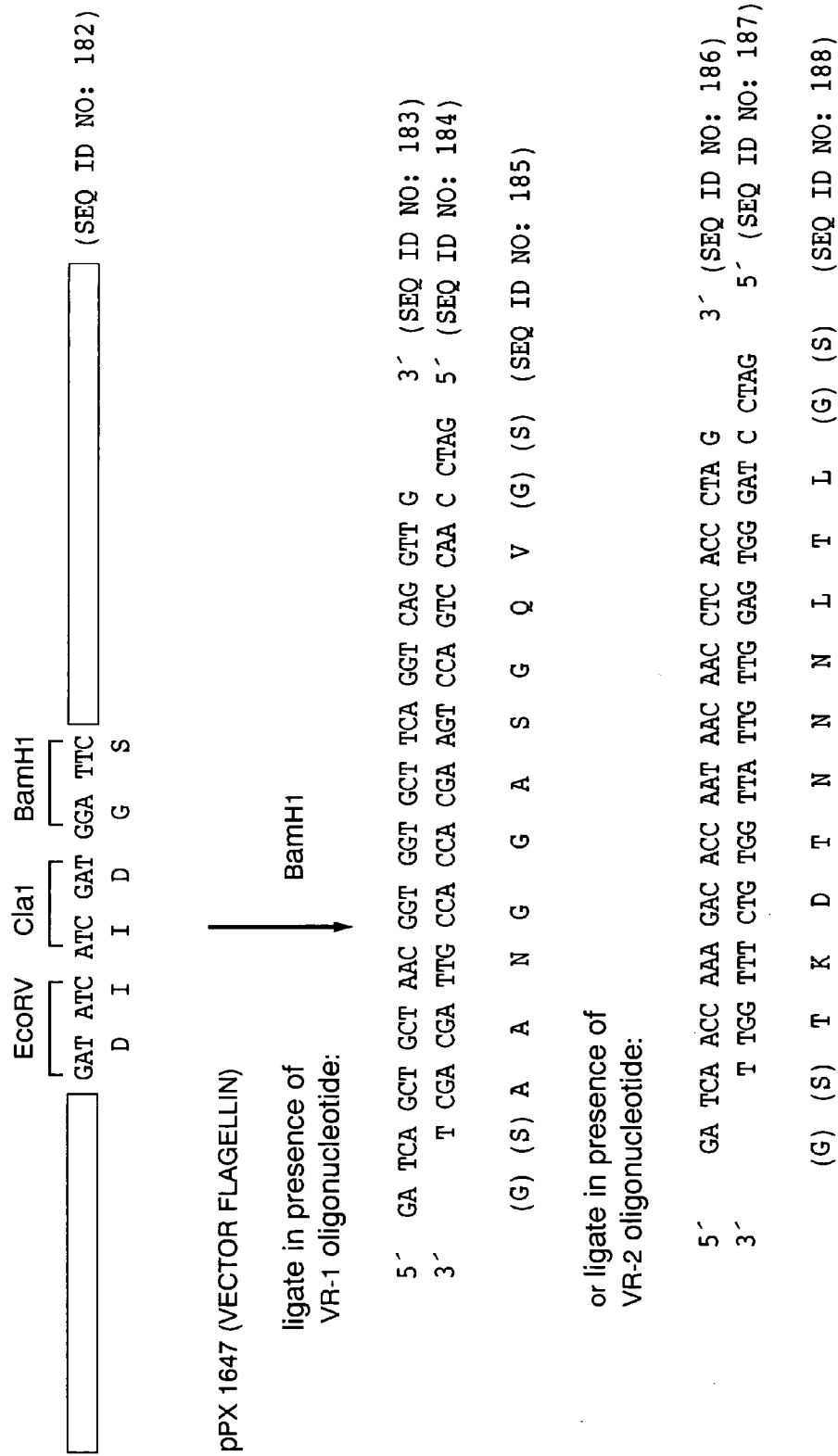
FIG. 6. (see also SEQ ID NOs 182–188) Construction of recombinant flagellins expressing variable region epitopes of N. meningitidis Class 1 OMP subtype P1.6,16.
Figure 7:
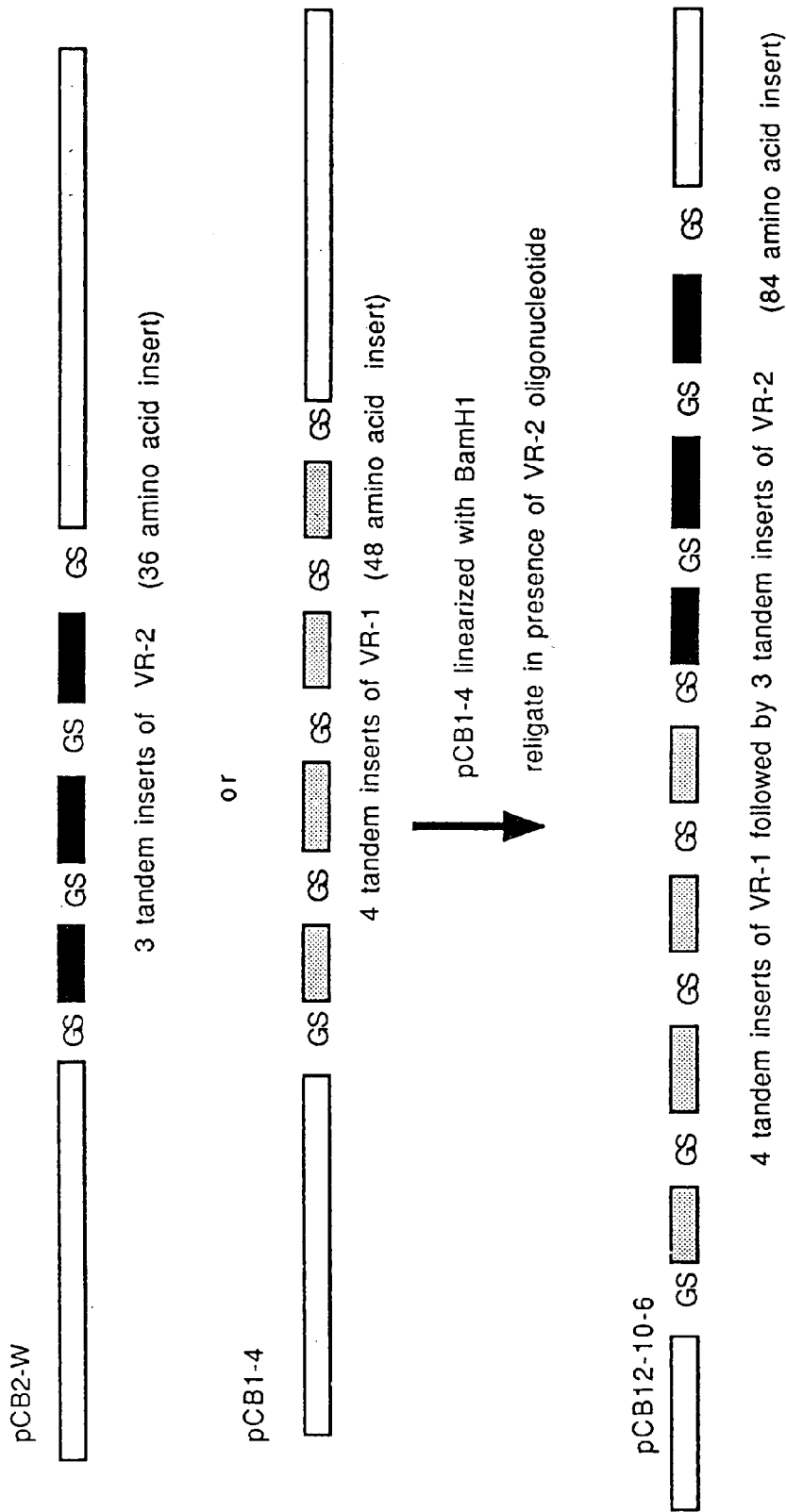
FIG. 7. Structure of recombinant flagellins expressing variable region epitopes of N. meningitidis Class 1 OMP subtype P1.6,16.

This invention pertains to vaccines comprising isolated OMV's, meningococcal Class 1 OMP, fragments of the OMP (e.g., prepared by the application of cyanogen bromide) and oligopeptides bearing epitopes of the OMP; the preparation of isolated OMV's, pure Class 1 outer-membrane proteins, using mutant strains which do not express the Class 2/3 outer-membrane protein; the preparation of isolated OMV's pure Class 1 outer-membrane proteins with the aid of cloned DNA in recombinant DNA expression vectors. This invention also comprises the application of genetic engineering with the object of producing isolated OMV, Class 1 OMP or portions thereof, genetic fusions of Class 1 OMP, portions or epitopes therof; and the preparation of multivalent Class 1 outer-membrane vaccine through peptide synthesis, as the epitopes with a short peptide chain can be synthetically prepared.

It has emerged that meningococcal Class 1 outer-membrane proteins induce a strong bactericidal immune response to the strains containing the appropriate subtype epitopes, irrespective of whether these are from group A, B, C, W-135, and Y strains. The polysaccharide vaccine can be enhanced or replaced by a vaccine according to the invention as a vaccine with broad, extensive action again most serotypes. The protective bactericidal monoclonal antibodies specific for the Class 1 outer-membrane protein react strongly with fragments that have been split off and short synthetic peptides which have been prepared using the amino acid sequence of Class 1 outer-membrane proteins. Since meningococcal disease is currently caused chiefly by group B meningococci and because the Class 1 outer-membrane proteins occurring in group B meningococci also occur in group A, C, W-135, and Y meningococci, vaccines of this invention which comprise one or more Class 1 OMP epitopes derived from N. meningitidis group B should be effective in preventing disease caused by group A, C, W-135 and Y. Preferably, the preparation of such a vaccine starts from at least two different immunogenic and protective epitopes which have been selected on epidemiological grounds. Vaccines according to the invention comprise, for example, at least one protein which is obtained either in OMV formulation or by purification from mutant strains producing one or more Class 1 OMP or at least two fragments prepared through a cyanogen bromide fragmentation or at least two synthetic peptides, chosen from about 10 major epitopes, or products obtained by gene expression via recombinant DNA technology, which contain the desired epitopes. To maximize efficacy to a broad range of meningococcal strains, the greater number of different protective epitopes in the vaccine the better. In addition, the vaccines according to the invention may advantageously contain meningococci A and C or optionally W-135 and Y polysaccharides and/or detergents. Preferably, the A and C polysaccharides are covalently coupled to a protein or polypeptide carrier. These carriers include, for example, isolated OMV, the Class 1 OMP protein, T-helper epitopes, bacterial toxins, toxoids, nontoxic mutants (CRM's), recombinant Salmonella flagelln and viral particles such as rotavirus VP6 protein, Hepatitis B surface antigen or parvovirus VP1 and VP2 proteins. Both zwitterionogenic, cationogenic, anionogenic and nonionogenic detergents can be used. Examples of such detergents are ZWITTERGENT 3-10, ZWITTERGENT 3-14 (N-tetradecyl-N,N-dimethyl-3-ammonia-1-propane sulphonate), TWEEN 20, sodium deoxycholate, sodium cholate and octylglucoside. The vaccines according to the invention may also contain an adsorbent such as aluminium hydroxide, calcium phosphate; or advantageously, aluminium phosphate. The fragments, proteins, and peptides can also be processed in immuno-stimulating complexes (ISCOMS), liposomes or microspheres for delivering and/or use as an adjuvant or in connection with other adjuvants so that greater immunogenicity is obtained.

This invention encompasses isolated OMV, substantially pure meningococcal Class 1 outer membrane proteins (of any subtype) and fragments of the proteins containing epitopes thereof. The fragments can be any portions of the molecular weight of 25 kD or less which contain epitopes which are bound by protective bactericidal antibodies against *N. meningitidis*. These include proteolytic fragments and synthetic oligopeptides which are comprised of amino acid sequences which correspond, at least in part, to epitopes of a Class 1 OMP.

The isolated OMV's, Class 1 OMP, fragments or epitope-containing oligopeptides derived therefrom can be comprised of amino acid sequences which are different, but essentially biologically equivalent to the natural sequences. These sequences can include sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include glycine, alanine, leucine, isoleucine, valine, proline, phenylalanine, tryptophan and methionine. The polar neutral amino acids include serine, threonine, cysteine, tyrosine, asparagine, and glutamine. The charged (basic) amino acids include arginine, lysine and histidine. The negatively charged (acidic) amino acids include aspartic and glutamic acids.

Additionally, isolated OMV's, the class 1 OMP, fragments or the oligopeptides can be modified for conjugation to other molecules (e.g., by the attachment of coupling groups such as the amino acids cysteine and/or lysine or other linking groups and/or spacer groups) including other Class 1 OMP of a different subtype, T cell epitopes, B cell epitopes, carrier peptides or proteins or adjuvanting molecules.

As described in detail below, the Class 1 OMP fragments or oligopeptides can be used in many different forms (e.g., alone, in mixtures, or as conjugates and genetic fusions produced from recombinant DNA vectors) in vaccines. For these purposes, the materials can be produced by isolation from *N. meningitidis,* by proteolytic digestion, by chemical synthesis, or by expression as recombinant molecules. The methods of production and use of the isolated OMV's, the class 1 OMP and the fragments and the oligopeptides of Class 1 OMP are described below.

Protein modeling and structure analysis of the Class 1 OMPs were performed using the principles for several *E. coli* outer membrane proteins. (Vogel, H. et al., *J. Mol. Bio.,* 190:191 (1986); Ference, T. et al., *J. Mol. Bio.,* 201:493 (1988) and Tommassen, J. in "Membrane Biogenesis", *NATO ASI Series H*16, pp351, Springer-Verlag, NY (1988)). The derived amino acid sequence of the Class 1 OMPs were used for the modeling studies and comparison. The amino acid sequence homology was compared to other gram negative bacterial porin proteins and similarity was established for the protein structure. Exposed surface loops and transmembrane structure were very similar for these porin proteins. With the information revealed concerning variable and constant region protective epitopes of *N. meningitidis* and their structure, one can predict based upon the amino acid sequence where protective epitopes may reside for other pathogenic gram negative bacteria to be evaluated and included in vaccines for the same.

Production of isolated OMV's

OMV's can be produced either from the culture supernatant or from the bacterial cells after fragmentation as described by Beuvery et al. (1983) *Infect. Immun.* 40:369–380. OMV's carrying proteins from more than one meningococcus can be isolated from strains manipulated to express heterologous proteins.

Production and Purification of Class 1 OMP and CNBr fragments thereof

Class 1 and Class 3 outer membrane proteins can be isolated as described by Beuvery, E. C. et al., Antonie van Leeuvenhoek *J. Microbiol.* 52:232 (1986). The production of substantially pure Class 1 OMP free of Class 2 or 3 OMP's is achieved by this method using mutant meningococcal strains which do not express Class 2/3 OMP. A preferred strain of production of Class 1 OMP is the HIII5 strain, deposited as CBS 636.89.

Fragments can be produced by cyanogen bromide cleavage as described by Teerlink T. et al., *J. Exp. Med.* 166:63 (1987) for a gonococcal protein. The N-terminal fragment is referred to as CB-1 and the C-terminal fragment is referred to as CB-2. These CNBr fragments can be purified via reverse phase HPLC on a Vydax™ C4 or an Aquapor™ R-300 column using a water/acetonitrile gradient. Alternatively, the fragment can be purified by multiple cold trichloroacetic acid precipitations. These procedures remove greater than 95% of interferring contaminants (e.g., buffer salts, detergents and fragment contaminants).

Preparation of fragments and oligopeptides containing epitopes of class 1 OMP

A. Preparation by proteolytic digestion

Oligopeptides containing epitopes reactive with bactericidal antibodies against *N. meningitidis* can be produced by digestion of the class 1 OMP, CB-1 or CB-2 fragments with proteinases such as endoLys-C, endoArg-C, endoGlu-C and staphylococcins V8-protease. The digested fragments can be purified by, for example, high performance liquid chromatographic (HPLC) techniques.

B. Preparation by Chemical synthesis

Oligopeptides of this invention can be synthesized by standard solid peptide synthesis (Barany, G. and Merrifield, R. B., *The Peptides* 2:1–284, Gross, E. and Meienhofer, J., Eds., Academic Press, New York) using tert-butyloxycarbonyl amino acids and phenylacetamidomethyl resins (Mitchell, A. R. et al., *J. Org. Chem.* 43:2845–2852 (1978)) or 9-fluorenylmethyloxycarbonyl amino acids on a polyamide suppport (Dryland, A. and Sheppard, R. C., *J. Chem. So. Perkin Trans. I,* 125–137 (1986)). Alternatively, synthetic peptides can be prepared by pepscan synthesis (Geysen, H. M. et al., *J. Immunol. Methods* 03:259 (1987); *Proc. Natl. Acad. Sci. USA* 81:3998 (1984)), Cambridge Research Biochemicals, Cambridge, U.K. or by standard liquid phase peptide synthesis. The deletion or substitution of amino acids (and including extensions and additions to amino acids) in other ways which do not substantially detract from the immunological properties of the oligopeptide.

The Class 1 OMP, fragments and oligopeptides which exhibit epitopes of the Class 1 OMP can be produced by recombinant DNA techniques. In general, these entail obtaining DNA sequences which encode the desired OMP, [Barlow et al., (1989) *Mol. Micro.,* 3:131) fragment or oligopeptide sequences and introducing into an an appropriate vector/host expression system one or more similar or different DNA sequences of Class 1 OMP's where it is expressed. The DNA can consist of the gene encoding the Class 1 OMP or any segment of the gene which encodes a functional epitope of the OMP. By recombinant methods one can produce, for example, a recombinant microorganism which expresses a peptide comprising an amino acid sequence selected from the group consisting of QPQVT-NGVQGN (SEQ ID NO:22), PPSKSQP (SEQ ID NO:23), AQAANGGASG (SEQ ID NO:20), YYTKNTNNNLTL (SEQ ID NO:190), YYTKDTNNNL (SEQ ID NO:17), YYTKNTNNNL (SEQ ID NO:18), HFVQQTPQSQP (SEQ ID NO:21) and HYTRQNNTDVF (SEQ ID NO:19). The DNA can be fused to DNA encoding other antigens of *N. meningitidis* (such as other outer membrane proteins either of the same or different class) or antigens of other bacteria, viruses, parasites or fungi to create genetically fused (sharing a common peptide backbone), multi-valent antigens. For example, Class 1 OMP fragments can be fused to another Class 1 outer membrane protein of a different subtype (or fragments or epitopes thereof) of *N. meningitidis* to yield fusion proteins comprising multiple Class 1 outer membrane protein subtype determinants.

Genetic engineering techniques can also be used to characterize, modify and/or adapt the encoded peptides or proteins. For example, site directed mutagenesis to modify an OMP fragment in regions outside the protective domains, for example, to increase the solubility of the subfragment to allow easier purification. DNA can also be manipulated to effect superproduction of OMP fragments or combinations thereof in various organisms.

DNA encoding a Class 1 OMP, fragments or oligopeptides can be synthesized or isolated and sequenced as described by Barlow, A. K. et al. *Infect. Immune* 55:2734–40 (1987) and Barlow, A. K. et al., *Mol. Micro.* 3:131 (1989). Class 1 OMP genes can be amplified from bacterial DNA by the methods of Mullis and Faloona, (1987) Method. Enzym. 155:335–350, using the primer sequences disclosed herein. Related DNA sequences for Class 1 OMP of different subtypes can be obtained by the procedures described and the amino acid sequences deduced.

A variety of host-vector systems can be used to express the oligopeptides of this invention. Primarily the vector system must be compatible with the host cell used. Host-vector systems include but are not limited to the following: bacteria transformed with bacteriophage DNA, plasmid DNA or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

In order to obtain efficient expression of the cloned DNA, a promoter must be present in the expression vector. RNA polymerase normally binds to the promoter and initiates transcription of a gene of a group of linked genes and regulatory elements (called an operon). Promoters vary in their "strength", i.e., their ability to promote transcription. It is desirable to use strong promoters in order to obtain a high level of transcription and, hence, a high level of DNA expression. Depending upon the host cell system any one of a number of suitable promoters can be used. For instance, for *E. coli,* its bacteriophages or plasmids, promoters such as the lac promoter, trp promoter, recA promoter, ribosomal RNA promoter, and $P_R$ or $P_L$ promoters of coliphage lambda and others including but not limited to lacUV5, ompF, bla, lpp and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted DNA.

Bacterial host cells and expression vectors may be chosen which inhibit the action of the promoter unless specifically induced. In certain operons the addition of specific inducers is necessary for efficient transcription of the inserted DNA; for example, the lac operon is induced by the addition of lactose or IPTG (isopropylthio-beta-D-galactoside). A variety of other operons, such as trp, etc., are under different controls. The trp operon is induced when tryptophan is absent in the growth media; and the $P_L$ promoter of lambda can be induced by an increase in temperature in host cells containing a temperature sensitive lambda repressor, e.g., cI857. In this way, greater than 95% of the promoter-directed transcription may be inhibited in uninduced cells. Thus, expression of the recombinant peptide or protein can be controlled. This is important if the expression product of the DNA is lethal or detrimental to the host cells. In such cases, transformants may be cultured under conditions such that the promoter is not induced; then, when the cells reach a suitable density in the growth medium, the promoter can be induced for production of the protein.

One such promoter/operator system is the "tac" or trp-lac promoter/operator system (Russell and Bennett, 1982, Gene 20:2312–243; DeBoer, European Patent Application, 67, 540 filed May 18, 1982). This hybrid promoter is constructed by combining the −35 b.p. (−35 region) of the trp promoter and the −10 b.p. (−10 region or Pribnow box) of the lac promoter (the sequences of DNA which are the RNA polymerase binding site). In addition to maintaining the strong promoter characteristics of the tryptophan promoter, tac is also controlled by the lac repressor.

When cloning in a eukaryotic host cell, enhancer sequences (e.g., the 72 bp tandem repeat of SV40 DNA or the retroviral long terminal repeats or LTRs, etc.) may be inserted to increase transcriptional efficiency. Enhancer sequences are a set of eucaryotic DNA elements that appear to increase transcriptional efficiency in a manner relatively independent of their position and orientation with respect to a nearby gene. Unlike the classic promoter elements (e.g., the polymerase binding site and the Goldberg-Hogness "TATA" box) which must be located immediately 5' to the gene, enhancer sequences have a remarkable ability to function upstream from, within, or downstream from eucaryotic genes; therefore, the position of the enhancer sequence with respect to the inserted DNA is less critical.

Specific initiation signals are also required for efficient gene transcription and translation in procaryotic cells. These transcription and translation initiation signals may vary in "strength" as measured by the quantitiy of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno (SD) sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Any of the methods described for the insertion of DNA into an expression vector can be used to ligate a promoter and other genetic control elements into specific sites within the vector. N. meningitidis sequences for expression can be ligated into an expression vector at a specific site in relation to the vector promoter and control elements so that when the recombinant DNA molecule is introduced into a host cell the foreign genetic sequence can be expressed (i.e., transcribed and translated) by the host cell.

The recombinant DNA vector can be introduced into appropriate host cells (bacteria, virus, yeast, mammalian cells or the like) by transformation, transduction or transfection (depending upon the vector/host cell system). Host cells containing the vector are selected based upon the expression of one or more appropriate gene markers normally present in the vector, such as ampicillin resistance or tetracycline resistance in pBR322, or thymidine kinase activity in eucaryotic host systems. Expression vectors may be derived from cloning vectors, which usually contain a marker function. Such cloning vectors may include, but are not limited to the following: SV40 and adenovirus, vaccinia virus vectors, insect viruses such as baculoviruses, yeast vector, bacteriophage vectors such as lambda gt-WES-lambda B, Charon 28, Charon 4A, lambda gt-1-lambda BC, lambda gt-1-lambda B, M13mp7, M13mp8, M13mp9, or plasmid DNA vectors such as pBR322, pAC105, pVA51, pACYC177, pKH47, pACYC184, pUB110, pMB9, pBR325, Col E1, pSC101, pBR313, pML21, RSF2124, pCR1, RP4, pBR328 and the like.

Expression vectors containing the DNA inserts can be identified by three general approaches: (1) DNA-DNA hybridization using probes comprising sequences that are homologous to the inserted gene; (2) presence or absence of "marker" gene functions (e.g., resistance to antibiotics, transformation phenotype, thymidine kinase activity, etc.); and (3) expression of inserted sequences based on the physical immunological or functional properties of the gene product.

Once a putative recombinant clone which expresses a desired Class 1 OMP amino acid sequence is identified, the gene product can be analyzed as follows. Immunological analysis is especially important because the ultimate goal is to use the gene products in vaccine formulations and/or as antigens in diagnostic immunoassays. The expressed peptide or protein should be immunoreactive with bactericidal antibodies against *N. meningitidis*. This reactivity may be demonstrated by standard immunological techniques, such as radioimmuno-precipitation, radioimmune competition, ELISA or immunoblots.

Once the gene product is identified as a Class 1 OMP fragment or an oligopeptide containing a functional epitope thereof, it can be isolated and purified by standard methods including chromatography (e.g., ion exchange, affinity, and sizing column chromatography), centrifugation, differential solubility, or by any other standard techniques for the purification or proteins. Several techniques exist for purification of heterologous protein from prokaryotic cells. See e.g., Olson, U.S. Pat. No. 4,518,526, Wetzel, U.S. Pat. No. 4,599,197 and Hung et al., U.S. Pat. No. 4,734,362. The purified preparation however produced should be substantially free of host toxins which might be harmful to humans. In particular, when expressed in gram negative bacterial host cells such as *E. coli* or *Salmonella,* the purified peptide or protein should be substantially free of endotoxin contamination.

Class 1 OMP, fragments and oligopeptides of this invention can be formulated as univalent and multivalent vaccines. These materials can be used as produced or isolated by the methods described above. They can be mixed, conjugated or fused with other antigens, including B or T cell epitopes of other antigens. In addition, they can be conjugated to a carrier protein as described below for oligopeptides.

When a haptenic oligopeptide is used (i.e., a peptide which reacts with cognate antibodies, but cannot itself elicit an immune response), it can be conjugated to an immunogenic carrier molecule. Conjugation to an immunogenic carrier can render the oligopeptide immunogenic. The conjugation can be performed by standard procedures. Preferred carrier proteins for the haptenic oligopeptides are toxins, toxoids or any mutant crossreactive material (CRM) of the toxin from tetanus, diphtheria, pertussis, *Pseudomonas, E. coli, Staphylcoccus,* and *Streptococcus.* A particularly preferred carrier is $CRM_{197}$ of diphtheria toxin, derived from *P. diphtheriae* strain C7 (β197) which produces $CRM_{197}$ protein. This strain has ATCC accession no. 53281. Alternatively, a fragment or epitope of the carrier protein or other immunogenic protein can be used. For example, the hapten can be coupled to a T cell epitope of a bacterial toxin, toxoid or CRM. See U.S. patent application Ser. No. 150,688, filed Feb. 1, 1988, entitled "Synthetic Peptides Representing a T-Cell Epitope as a Carrier Molecule For Conjugate Vaccines", the teachings of which are incorporated herein. Other carriers include viral particles composed of Rotavirus VP6, Hepatitis B surface antigen or parvovirus VP1 and VP2.

The peptides or proteins of this invention can be administered as multivalent subunit vaccines in combination with antigens of *N. meningitidis* or antigens of other organisms. Some of the other organisms include the pathogenic bacteria *H. influenzae, N. meningitidis, B. catarrhalis, N. gonorrhoeae, E. coli, S. pneumoniae,* etc. For example, they may be administered in conjunction with oligo- or polysaccharide capsular components of *N. meningitidis.* The capsular components can be derived from any of the serological groups, including A, B, C, D, X, Y, Z, 29E and W135.

Class 1 outer membrane proteins of different subtypes can be used. These may be used in combination to evoke bactericidal antibodies against *N. meningitidis.* For example, a fragment derived from Class 1 outer membrane protein of the P1.7.16 subtype can be used together with outer membrane proteins or fragments of outer membrane proteins of other subtypes, such as P1.1, P1.1.16; P1.2; P1.6; P1.9; P1.15; P1.16; or P1.4 (Abdillahi, H. et al. 1988 *Micro. Pathog.* 4:27) or with meningococcal polysaccharides in mixtures or as chemical conjugates. For combined administration with epitopes of other outer membrane proteins, they can be administered separately, as a mixture or as a conjugate or genetic fusion peptide or protein. The conjugates can be formed by standard techniques for coupling proteinaceous materials or techniques for coupling saccharide polymers to proteins. Fusions can be expressed from fused gene constructs prepared by recombinant DNA techniques as described.

As mentioned, Class 1 OMP, fragment or any oligopeptides derived therefrom can be used in conjunction with antigens (e.g., polymer capsules or saccharide units, envelope or surface proteins) of other pathogenic organisms (e.g. bacteria (encapsulated or nonencapsulated), viruses, fungi and parasites). Additional examples of other organisms include respiratory syncytial virus, rotavirus, malaria parasites, and *Cryptococcus neoformans.*

In formulating the vaccine compositions with the peptide or protein, alone or in the various combinations described, the immunogen is adjusted to an appropriate concentration and formulated with any suitable vaccine adjuvant. Suitable adjuvants include, but are not limited to: surface active substances, e.g., hexadecylamine, octadecylamine, octadecyl amino acid esters, lysolecithin, dimethyl-dioctadecylammonium bromide), methoxyhexadecylgylcerol, and pluronic polyols; polyamines, e.g., pyran, dextransulfate, poly IC, carbopol; peptides, e.g., muramyl dipeptide and derivatives, dimethylglycine, tuftsin; oil emulsions; and mineral gels, e.g., aluminum hydroxide, aluminum phosphate, etc., lymphokines and immune stimulating complexes (ISCOMS). The immunogen may also be incorporated into liposomes, microspheres, or conjugated to polysaccharides and/or other polymers for use in a vaccine formulation.

The vaccines can be administered to a human or animal in a variety of ways. These include intradermal, intramuscular, intraperitoneal, intravenous, subcutaneous, oral and intranasal routes of administration.

Live vaccines

The peptide and proteins of this invention can be administered as live vaccines. To this end, recombinant microorganisms are prepared that express the peptides or proteins. The vaccine recipient is inoculated with the recombinant microorganism which multiplies in the recipient, expresses the Class 1 OMP, fragment or oligopeptide thereof and evokes a immune response to N. meningitidis. Live vaccine vectors include: adenovirus, cytomegalovirus and preferably, pox viruses such as vaccinia (Paoletti and Panicali, U.S. Pat. No. 4,603,112) and attenuated *Salmonella* strains (Stocker, U.S. Pat. No. 4,550,081 and Curtiss et al., *Vaccine* 6:155–160 (1988)). In addition, class 1 OMP epitopes can be incorporated into the flagella of attenuated bacterial strains.

Live vaccines are particularly advantageous because they lead to a prolonged stimulus which can confer substantially long-lasting immunity. When the immune response is protective against subsequent N. meningitidis infection, the live vaccine itself may be used in a preventative vaccine against N. meningitidis.

Multivalent live vaccines can be prepared from a single or a few recombinant microorganisms that express different epitopes of N. meningitidis (e.g., other outer membrane proteins from other subtypes or epitopes thereof). In addition, epitopes of other pathogenic microorganisms can be incorporated into the vaccine. For example, a vaccinia virus can be engineered to contain coding sequences for other epitopes in addition to those of N. meningitidis. Such a recombinant virus itself can be used as the immunogen in a multivalent vaccine. Alternatively, a mixture of vaccinia or other viruses, each expressing a different gene encoding for different epitopes of outer membrane proteins of N. meningitidis and/or epitopes of other disease causing organisms can be formulated as a multivalent vaccine.

An inactivated virus vaccine may be prepared. Inactivated vaccines are "killed", i.e., infectivity has been destroyed, usually by chemical treatment (e.g., formaldehyde treatment). Ideally, the infectivity of the virus is destroyed without affecting the proteins which carry the immunogenicity of the virus. In order to prepare inactivated vaccines, large quantities of the recombinant virus expressing the desired epitopes are grown in culture to provide the necessary quantity of relevant antigens. A mixture of inactivated viruses express different epitopes may be used for the formulation of "multivalent" vaccines. In certain instances, these "multivalent" inactivated vaccines may be preferable to live vaccine formulation because of potential difficulties arising from mutual interference of live viruses administered together. In either case, the inactivated virus or mixture of viruses may be formulated in a suitable adjuvant in order to enhance the immunological response to the antigens. Suitable adjuvants include: surface active substances, e.g., hexadecylamine, octadecyl amino acid esters, octadecylamine, lysolecithin, dimethyl-dioctadecylammonium bromide, N,N-dicocta-decyl-N',N'bis(2-hydroxyethyl-propane diamine), methoxyhexadecylglycerol, and pluronic polyols; polyamines, e.g., pyran, dextransulfate, poly IC, carbopol; peptides, e.g., muramyl dipeptide and derivatives thereof, dimethylglycine, tuftsin; oil emulsions; and mineral gels, e.g., aluminum hydroxide, aluminum phosphate, and lymphokines.

EXEMPLIFICATION

EXAMPLE 1

Monoclonal Antibodies Against Class 1 OMP's and Their Biological Activity

Type specific monoclonal antibodies were prepared against various meningococci Class 1 outer-membrane proteins. These monoclonal antibodies recognize the following subtypes: P1,1; P1,2; P1,6; P1,7; P1,9; P1,10; P1,15; P1,16; and P1,17 (now called P1,14). The monoclonal antibodies are available as "Monoclonal Kit Serotyping Meningococci" from the RIVM, Bilthoven, The Netherlands. All these monoclonal antibodies react with the SDS (sodium dodecyl sulfate) denatured protein when tested by Western blotting. It also emerged that a number of these monoclonal antibodies reacted with a 25 Kd CNBr fragment of the 42 Kd Class 1 outer-membrane protein (see below). This result implied that the Class 1 outer-membrane protein epitopes are mainly of linear type and can therefore be copied with synthetic peptides. The epidemiological results of these carried out by the Applicants show that the described monoclonal antibodies can subtype most of the group A, B, C meningococci which suggests a limited heterogenity. Each Class 1 outer membrane protein also appears to contain two individual type specific epitopes (Abdillahi and Poolman, Microb. Pathogen, 1988, 4: pages 27–32; idem FEMS Microbiol. Immunol. 47: pages 139–144).

The purified Class 1 outer-membrane protein (see below), subtype P1,7.16, originating from the culture of the Class 2/3 free mutant (HIII5) appeared to induce a bactericidal antibody response of 1:64 serum dilution in a dose of 2.5 µg in mice. The monoclonal antibodies against meningococci Class 1 outer-membrane proteins, Class 2/3 outer-membrane proteins and lipopolysaccharides were compared as to bacteridical effect. The monoclonal antibodies against the Class 1 outer-membrane proteins appeared to possess the strongest bactericidal activity (see Table 1). The bactericidal response was determined as per Poolman, J. T. (1985), in Schoolnick, G. K. et al. Eds. 'The Pathogenic Neisseriae' ASM Publications, Washington, D.C., page 562.

TABLE 1

Bactericidal activity of a collection of monoclonal antibodies, directed against the Class 1 (cl 1), Class 2/3 (cl 2/3) and lipopolysaccharide (LPS) of meningococci. (ND = not determined).

| Test strain strain (Gp:serotype: subtype:LPS type) | Bactericidal activity of antibody pool (titre) | | |
|---|---|---|---|
| | Cl 2/3 pool | Cl 1 pool | LPS pool |
| 3006 (B:26:P1.2:L2) | 1000 | 8000 | ND |
| M981 (B:4P1.—:L5) | 10 | ND | 2000 |
| M990 (B:6:P1.6:L/) | 10 | 2000 | ND |
| M978 (B:8:P1.1:L1.8) | ND | 8000 | 1000 |
| M982 (B:9:P1.9:L3.7) | 500 | 2000 | 1000 |
| H355 (B:15:P1.15:L1.8) | 1000 | 8000 | 1000 |
| H44/76 (B:15:P1.7.16:L3.7) | 1000 | 8000 | 4000 |

The bactericidal activity of these monoclonal antibodies appears to correlate well with the in vivo protective activity as measured in the rat meningitis model of Saukkonen et al., 1987, *Microbial Pathogen* 3:261.

EXAMPLE 1A

Construction of Meningococcal Strains Carrying Multiple Class 1 Genes

Replacement of chromosomal genes by clones, slightly different versions has been described for *Neisseria gonorrhoeae* (Stein, D. C., *Clin. Microbiol. Rev.* 2 (Suppl.), S146–S149 (1989).) We have found that this method can be applied to the Class 1 gene in *Neisseria meningitidis*. This was done in the following way:

(i) The Class 1 gene of strain 2996 (subtype P1.2) was cloned into the vector pTZ19R. (Mead, D. A. et al., *Protein Engineering* 1, 67 (1986).) The complete gene is located on a 2.2 kb XbaI fragment that was ligated to XbaI digested vector DNA.

(ii) The resulting plasmid was used for transformation of strain H44/76 (subtype P1.7,16). Cells of the acceptor strain were incubated with plasmid DNA in the presence of $Mg^{2+}$ and normal meningococcal medium; they were subsequently diluted and plated, and the resulting colonies were tested for their ability to bind P1.2-specific monoclonal antibody. Such transformants were found with a frequency of approximately $10^{-3}$. Further characterization showed that replacement of the H44/76 Class 1 gene had indeed occurred. An essential feature of the method is the presence of the donor gene on a circular plasmid DNA molecule that is not able to replicate in *N. meningitidis,* since the use of linearized DNA yielded no transformants at all.

Construction of a strain with two Class 1 genes was done by a modification of the method described above. For this purpose, the P1.2 Class 1 gene was inserted into a clones Class 5 gene. The Class 5 gene family has two features which make it particularly suitable for this construction. (Meyer, T. F. and Van Putten, J. P. M., *Clin. Microbiol. Rev.,* 2 (Suppl.) S139–S145 (1989): (i) there are four or five Class 5 genes present in the meningococcal genome, and (ii) expression of these genes is not necessary for growth under laboratory conditions. A Class 5 gene was cloned from strain H44/76 and the P1.2 gene was inserted into an SphI site located in or very close to the Class 5 gene. The resulting hybrid plasmid, pMC22, was used for transformation of strain HIII5, a Class 3-deficient mutant of H44.76. Colonies reacting with the P1.2-specific monoclonal antibody were isolated and characterized. Out of 10 such transformants, nine were found to have lost the P1.16 epitope of the acceptor strain. This indicates that in all these cases recombination has only occurred between the Class 1 genes, resulting in subtype replacement. However, one transformant was found which made both Class 1 subtypes, i.e., P1.7,16 and P1.2, suggesting that recombination between the Class 5 gene sequences on plasmid and chromosome must have occurred. This was confirmed by Western blotting, which revealed the presence of both types of Class 1 protein and by Southern blotting, which demonstrated the acquisition of a second Class 1 gene.

By continuing this construction with other Class 1 subtypes, it is possible to make a strain with four or five different Class 1 genes. The same Class 5 gene can be used in each subsequent transformation step, the different Class 5 genes can be clones and used separately. These recombinant strains can be used to prepare mixtures of different purified Class 1 OMPs.

EXAMPLE 1B

Purification of Isolated OMV's from Bacteriological Culture

The purification is carried out according to Beuvery et al. (1983) Infect. Immun. 40: 369–380.

This culture can be done with the desired wild type strains, mutant meningococci strains without Class 2/3 outer-membrane proteins and/or homologeous and heterologeous recombinant microorganisms which express one or more of the desired meningococci Class 1 outer-membrane protein and/or epitopes by overproducing vectors either through or not through existing open reading frames and/or manipulated reading frames so that fusion proteins or proteins with exchanged epitopes can be prepared.

Readily available of wild strains are: H44/76 (B:15:P1,7.16) (Holten E., Norway, deposited as CBS 635-89); 187 (B:4:P1,7) (Etienne J., France); M1080 (B:1:P1,1.7) (Frasch C., USA); Swiss4 (B:4:P1,15) (Hirschel B., Switzerland); B2106I (B:4:P1,2) (Berger U., West-Germany); 395 (B:NT:P1,9) (Jonsdottir K., Iceland): M990 (B:6:P1,6) (Frasch C., USA); 2996 (B:2b:P1,2) RIVM, The Netherlands; M982 (B:9:P1,9) (Frasch C., USA); S3446 (B:14:P1,6) (Frasch C., USA); H355 (B:15:P1,15) (Holten E., Norway); 6557 (B:17:P1,17) (Zollinger W., USA) and B40 (A:4:P1,10) (Achtman M., West-Germany). An example of a Class 3 negative mutant is HIII5 (B:-:P1.16) deposit # CBS 636.89.

These strains were inoculated from precultures at −70° C. into shake flasks and transferred from these into 40, 150 or 350 liter fermenter cultures. The semisynthetic medium had the following composition: L-glutamic acid 1.3 g/l, L-cysteine.HCl 0.02 g/l, $Na_2HPO_4.2H_2O$ 10 g/l, KCl 0.09 g/l, NaCl 6 g/l, $NH_4Cl$ 1.25 g/l, $MgSO_4.7H_2O$ 0.6 g/l, glucose 5 g/l, $Fe(NO_3)_3$ 100 μM, yeast dialysate.

During culturing in the fermenter, the pH and $PO_2$ were monitored and automatically regulated to a pH of 7.0–7.2 and an air saturation of 10%. The cells were grown to early stationary phase harvested by means of centrifuging and washing with sterile 0.1 M NaCl and stored at −20° C. or freeze-dried.

EXAMPLE 2

Purification of Class 1 Outer-Membrane Proteins from Bacteriological Culture

This culture can be done with the desired wild type strains, mutant meningococci strains without Class 2/3 outer-membrane proteins and/or homologeous and heterologeous recombinant microorganisms which express one or more of the desired meningococci Class 1 outer-membrane protein and/or epitopes by overproducing vectors either through or not through existing open reading frames and/or manipulated reading frames so that fusion proteins or proteins with exchanged epitopes can be prepared.

Readily available of wild strains are: H44/76 (B:15:P1,7.16) (Holten E., Norway, deposited as CBS 635-89); 187 (B:4:P1,7) (Etienne J., France); M1080 (B:1:P1,1.7) (Frasch C., USA); Swiss4 (B:4:P1,15) (Hirschel B., Switzerland); B2106I (B:4:P1,2) (Berger U., West-Germany); 395 (B:NT:P1,9) (Jonsdottir K., Iceland): M990 (B:6:P1,6) (Frasch C., USA); 2996 (B:2b:P1,2) RIVM, The Netherlands; M982 (B:9:P1,9) (Frasch C., USA); S3446 (B:14:P1,6) (Frasch C., USA); H355 (B:15:P1,15) (Holten E., Norway); 6557 (B:17:P1,17) (Zollinger W., USA) and B40 (A:4:P1,10) (Achtman M., West-Germany). An example of a Class 3 negative mutant is HIII5 (B:-:P1.16) deposit # CBS 636.89.

These strains were inoculated from precultures at −70° C. into shake flasks and transferred from these into 40, 150 or 350 liter fermenter cultures. The semisynthetic medium had the following composition: L-glutamic acid 1.3 g/l, L-cysteine.HCl 0.02 g/l, $Na_2HPO_4.2H_2O$ 10 g/l, KCl 0.09 g/l, NaCl 6 g/l, $NH_4Cl$ 1.25 g/l, $MgSO_4.7H_2O$ 0.6 g/l, glucose 5 g/l, $Fe(NO_3)_3$ 100 μM, yeast dialysate.

During culturing in the fermenter, the pH and $PO_2$ were monitored and automatically regulated to a pH of 7.0–7.2 and an air saturation of 10%. The cells were grown to early stationary phase harvested by means of centrifuging and washing with sterile 0.1 M NaCl and stored at −20° C. or freeze-dried.

The bacterial mass was for example extracted with the aid of 0.5 M $CaCl_2$, 1% (w/v) ZWITTERGENT 3-14 (Zw 3-14) and 0.14 M NaCl, pH 4.0, using 100 ml per gram of freeze-dried bacterial mass. The suspension was stirred for 1 hour at room temperature and then centrifuged (1 hour, 3000×g), after which the supernatant was collected in a sterile manner. 20% ethanol (v/v) was added to the supernatant and after stirring for 30 min. the product was centrifuged (30 min., 10,000×g), after which the supernatant was collected aspectically. The supernatant was then concentrated by means of diafiltration in an Amicon Hollow Fiber System (HID×50, cut off 50,000) and $CaCl_2$ and ethanol were removed. The concentrate was diluted with 0.1 M sodium acetate, 25 mM EDTA, 0.05% Zw 3-14 having a pH of 6.0 to the original volume and then concentrated again by means of diafiltration. This procedure was repeated five times. The pH of the final concentrate was adjusted to a value of 4.0. 20% (v/v) ethanol was added to the concentrate and, after stirring for 30 min., the product was centrifuged (30 min., 10,000×g). The whole proteins are purified with the aid of column chromatography in the presence of detergent, for example Zw 3-14. Often gel filtration over SEPHACRYL S-300 as well as the ion exchange over DEAE SEPHAROSE is applied (Beuvery et al., (1986) supra). The used extraction method, detergents, column chromotography are not the only applicable method yet only serve as examples and must not be regarded as restrictive.

EXAMPLE 3B

Preparaton and Characterization of Class 1 OMP Peptide Fragments

Cyanogen bromide was used to prepare fragments of meningococcal Class 1 outer-membrane proteins. The purified Class 1 or mixtures of Class 1 or 3 outer-membrane proteins were taken up in 70% (v/v) formic acid and treated with a 10-fold excess of CNBr for 16 hours at room temperature. The CNBr and the formic acid were removed by means of evaporation and replaced by 0.2 M Tris-HCl, 6 M urea solution, pH 7.2. The supernatant was prepurified by means of gel filtration over SEPHACRYL S-200 and subsequently purified with the aid of TSK-2000 gel filtration via HPLC. Beuvery et al., (1986) supra.

Enzymatic digestion of CB2 fragments

To further delineate the epitopes, the meningococcal CB2 fragment was subjected to digestion with EndoArg-C, Endo-Glu-C or V-8 and the resulting fragments isolated by HPLC. Briefly, 20 nMoles of CB2 fragment in 1 ml of 25 mM phosphate/0.1 mM tris buffer (pH 8.0) containing 3M urea was digested at 37° C. with 0.2 nMoles of EndoArg-C (1 mg/ml in distilled water) or 0.22 nMoles of EndoGlu-C or V-8 (1 mg/ml in distilled water) for 14–18 hours. The resulting digesting fragments were separated by reverse phase HPLC using a VYDAC C4 column and a trifluoroacetic acid-acetonitrile gradient. The main peak eluted from the EndoArg-C digestion had an apparent molecular weight of 7–9 Kdal while the main peak observed following Endo-Glu-C or V-8 had an apparent molecular weight of 4–6 Kdals. The isolated peaks were subsequently shown by Western blot to react to a pool of monoclonal antibodies (Adam I, 62-D12-8, MN5-C11G and MN14-C116).

The P1.16 epitope appears to be present on the C-terminal CNBr fragment of the Class 1 outer-membrane protein of strain H44/76 (B:15:P1,7.16). Further characterisation of the P1,16 epitope was carried out through amino acid sequence determination of the 17 Kd (N-terminal) and 25 Kd (C-terminal) CNBr fragments. The C-terminal 25 Kd is further fragmented with V8 protease, endoLysC, endoGlu-C and endoArg-C. Fragments which were positive with the P1,16 monoclonal antibody were sequenced as far as possible. The sequences which were obtained are as follows:

```
N-terminus of whole protein:              (SEQ ID NO:1)
DVSLYGEIKAGVEDRNYQLQLTEAQUAAGN N-terminus of 25 Kd C-terminal            (SEQ ID NO:2)
CNBr fragment:
(M) PVSVRYDSPEFSGFSGSVQFVPIONSKSAYTPAYYTKDTNNN
```

Fragments which react with P1,16 monoclonal antibodies were isolated using V8 protease and endoArg-C fragmentation with a molecular weight of 7–9 Kd and 4–6 Kd respectively. The N-terminal sequences hereof are as follows:

```
V8 7-9 Kd fragment:                       (SEQ ID NO:3)
FSGFSGSVQFVPIQNSKSAYTPAYYTKDTN Arg-C 4-6 Kd fragment:                    (SEQ ID NO:4)
PVSVRYDSPEFSGFSGSVQFVPIQNSKSAYTPAYYTK
```

EXAMPLE 4

DNA Sequences of Class 1 OMP Genes

Amino acid sequences of Class 1 OMP were deduced from the nucleotide sequence of the structural genes of four meningococci Class 1 OMP's with various subtypes. Comparison with four amino acid sequences enabled a prediction of the composition and the location of these epitopes. Further, the P1,7 and P1,16 epitopes were confirmed with the aid of peptide synthesis and the demonstration of binding of the respective monoclonal antibodies.

Class 1 OMP genes were cloned into lambda gt11 (as described for P1, 16 in Barlow et al., (1987) *Infect. Immun.* 55: 2743–2740) and subcloned in M13 sequencing vectors and the DNA sequence was determined by standard chain termination dideoxynucleotide techniques.

The complete derived amino acid sequence for P1,16; P1,15, P7,16; and P1,2 proteins are as follows:

```
                         10        20        30        40        50
P1.16 (SEQ ID NO:5):   DVSLYGEIKAGVEGRNIQAQLTEQPQVTNGVQGNQV--KVTKAKSRIRTKIS
                       **************** * ****              *************

P1.15 (SEQ ID NO:6):   DVSLYGEIKAGVEGRNFQLQLTEPP-SKSQP---QV--KVTKAKSRIRTKIS
                       **************** * ****              *************

P1.7.16 (SEQ ID NO:7): DVSLYGEIKAGVEGRNYQLQLTEAQAANGGASGQVKVTKVTKAKSRIRTKIS
                       **************** * ****              *************

P1.2 (SEQ ID NO:8):    DVSLYGEIKAGVEGRNIQLQLTEPLQNIQQPQ-------VTKAKSRIRTKIS
                       **************** * ****              *************

60        70        80        90       100       110
                       DFGSFIGFKGSEDLGEGLKAVWQLEQDVSVAGGGASQWGNRESFIGLAGEFGTLRAGRVA
                       ****************** *****************  ******* **************

DFGSFIGFKGSEDLGEGLKAVWQLEQDVSVAGGGATQWGNRESFVGLAGEFGTLRAGRVA
                       ****************** *****************  ******* **************

DFGSFIGFKGSEDLGDGLKAVWQLEQDVSVAGGGATQWGNRESFIGLAGEFGTLRAGRVA
                       ****************** *****************  ******* **************

DFGSFIGFKGSEDLGEGLKAVWQLEQDVSVAGGGATRWGNRESFVGLAGEFGTLRAGRVA
                       ****************** *****************  ******* **************

120       130       140       150       160       170
                       NQFDDASQAINPWDSNNDVASQLGIFKRHDDMPVSVRYDSPEFSGFSGSVQFVPAQNSKS
                       ******* ** ******************************* ************ *****

NQFDDASQAIDPWDSNNDVASQLGIFKRHDDMPVSVRYDSPDFSGFSGSVQFVPIQNSKS
                       ******* ** ******************************* ************ *****

NQFDDASQAIDPWDSNNDVASQLGIFKRHDDMPVSVRYDSPEFSGFSGSVQFVPIQNSKS
                       ******* ** ******************************* ************ *****

NQFDDASKAIDPWDSNNVVASQLGIFKRMDDMPVSVRYDSPEFSGFSGSVQFVPAQNSKS
                       ******* ** ******************************* ************ *****

180       190       200       210       220       230
                       AYKPAYYTKDTNNNLTLVPAVVGKPGSDVYYAGLNYKNGGFAGNYAFKYARHANVGRNAF
                       ** **          ****************************** ************** **

AYTPAHYTRQNNTDV-FVPAVVGKPGSDVYYAGLNYKNGGFAGSYAFKYARHANVGRDAF
                       ** **          ****************************** ************** **

AYTPAYYTKNTNNNLTLVPAVVGKPGSDVYYAGLNYKNGGFAGNYAFKYARHANVGRNAF
                       ** **          ****************************** ************** **

AYTPAHFVQQTPQQPTLVPAVVGKPGSDVYYAGLNYKNGGFAGNYAFKYAKHANVGRDAF
                       ** **          ****************************** ************** **

240       250       260       270       280       290
                       ELFLIGSATSDEAKGTDPLKNHQVHRLTGGYEEGGLNLALAAQLDLSENGDKAKTKNSTT
                       **** **  **  ****************************************** *  *******

ELFLLGS-TSDEAKGTDPLKNHQVHRLTGGYEEGGLNLALAAQLDLSENGDKAKTKNSTT
                       **** **  **  ****************************************** *  *******

ELFLIGS-GSDQAKGTDPLKNHQVHRLTGGYEEGGLNLALAAQLDLSENGD--KTKNSTT
                       **** **  **  ****************************************** *  *******

ELFLLGS-GSDEAKGTDPLKNHQVHRLTGGYEEGGLNLALAAQLDLSENAD--KTKNSTT
                       **** **  **  ****************************************** *  *******

300       310       320       330       340       350
                       EIAATASYRFGNAVPRISYAHGFDLIERGKKGENTSYDQIIAGVDYDFSKRTSAIVSGAW
                       ****************************** *****************************

EIAATASYRFGNAVPRISYAHGFDLIERGKKGENTSYDQIIAGVDYDFSKRTSAIVSGAW
                       ****************************** *****************************

EIAATASYRFGNAVPRISYAHGFDFIERGKKGENTSYDQIIAGVDYDFSKRTSAIVSGAW
                       ****************************** *****************************

EIAATASYRFGNAVPRISYAHGFDFIERGKKGENTSYDQIIAGVDYDFSKRTSAIVSGAW
                       ****************************** *****************************

360       370
                       LKRNTGIGNYTQINAASVGLRHKF
```

```
                    -continued
         *************************

LKRNTGIGNYTQINAASVGLRHKF
         *************************

LKRNTGIGNYTQINAASVGLRHKF
         *************************

LKRNTGIGNYTQINAASVGLRHKF
         *************************
+Note this amino acid 15 is located between A.A.S. 184 and 185 of this sequence
```

EXAMPLE 5

DNA Sequencing of Class 1 OMP Genes from Different N. meningitidis Serosubtypes

The Polymerase Chain Reaction (PCR) technique of Mullis and Faloona (Methods in Enzymol. 155:335–50, 1987) was used to amplify the entire Class 1 OMP gene and specific fragments according to the scheme shown in FIG. 1.

Primers were synthesized on an Applied Biosystems 380B DNA synthesizer and used in standard PCR 30 cycle amplification reactions using Taq polymerase in a Thermal Cycler (Perkin-Elmer Cetus, Norwalk, Conn.) according to the recommendations of the Supplier. Amplified fragments of about 1300, 900 and 450 bp were generated from each serosubtype genomic DNA preparation from the primer combinations shown in FIG. 1. The primers used had the following sequences:

```
                                              (SEQ ID NO:9)
PR1: (41 bases with universal primer extension)
TGT AAA ACG ACG GCC AGT TTG AAG ACG TAT CGG GRG TTT
GC (SEQ ID NO:10)
PR2: (42 bases with universal primer extension)
TGT AAA ACG ACG GCC AGT GGC GAA TTC GGT ACG CTG CGC
GCC (SEQ ID NO:11)
PR3: (42 bases with universal primer extension)
TGT AAA ACG ACG GCC AGT CAT CAG GTA CAC CGC CTG ACG
GGC (SEQ ID NO:12)
PR4: (40 bases with universal primer extension)
TGT AAA ACG ACG GCC AGT GCA GAT TGG CAG TCA GAT TGC
A (SEQ ID NO:13)
PR5: (40 bases with universal primer extension)
TGT AAA ACG ACG GCC AGT GGG ATC GGT ACC TTT GGC TTG
A (SEQ ID NO:14)
PR6: (40 bases with universal primer extension)
TGT AAA ACG ACG GCC AGT AAC TGA TTC GCA ACG CGA CCG
G FWD: (24 bases)                               (SEQ ID NO:15)
TTG AAG GAC GTA TCG GGT GTT TCG REV: (23 bases)                               (SEQ ID NO:16)
GCA GAT TGG CAG TCA GAT TGC TT
```

Excess single stranded template for sequencing was synthesized in an 'asymmetric PCR' amplification using 100× excess of primer carrying an 18 base extension at the 5' end corresponding to the universal fluoresenct sequencing primers used with an Model 370A Automated DNA Sequencer (Applied Biosystems, Foster City, Calif.). Taq polymerase was used in a Standard dideoxynucleotide chain termination sequencing reaction with the PCR generated single stranded Class 1 gene fragments as templates. Derived sequences for gene segments of strains H44/76 (P1.7,16), M1080 (P1.1,7), H355 (P1.15), 6940 (P1.6), 6557 (P1.14), 870227 (P1.10) and B40 (P1.10) are shown in FIG. 2 (see also SEQ ID NOs 61–74 and FIGS. 3A, 3B and 3C (see also SEQ ID NOs 75–84).

EXAMPLE 6

Confirmation of Amino Acid Sequences of Class 1 OMP Subtype Epitopes

From these gene sequences confirmed by direct sequencing of Class 1 OMP genes, it was deduced that the sequences corresponding to amino acids 24–34 and 176–187 of P1.16 are markedly variable in the four Class 1 OMP sequences. Three amino acid sequences N-terminal or C-terminal from these positions should also be considered for possible inclusion in these epitopes to allow for maximizing epitope stability presentation and unexpected insertions or deletions in the native protein sequence. Further the DNA and amino acid sequences of other Class 1 OMPs should be compared with the P1.7,16 sequence to allow for maximum alignment and epitope prediction. The first variable region epitope and second variable region epitope are called VR1 and VR2 respectively. These regions encode the subtype epitopes as was confirmed with the aid of peptide synthesis and the reaction of the peptides with P1.2; P1.7; P1.15 and P1.16 specific monoclonal antibodies.

A complete set of overlapping decapeptides staggered by 5 amino acids were prepared using the P1.16 protein sequence. The anti-P1.16 monoclonal antibody reacted with the decapeptide YYTKDTNNNL (SEQ ID NO:17) from P1.16 reacted as expected and no other decapeptide. FIGS. 4*a*, 4*b*, 4*c*, 4*d*, 4*e*, 4*f*, 4*g* and 4*h*.

Of overlapping decapeptides provided with a one (1) amino acid sequence shift in the region 24–34 and 176–187 of the Class 1 OMP of strains H44/76 (P1.7,16), MC50 (P1.16) and MC51 (P1.15) more than one peptide reacted with the subtype specific monoclonal antibody. In most cases one or more of the group of these overlapping peptides reacted with the subtype specific monoclonal antibody more strongly than others (FIGS. 5*a*, 5*b*, 5*c*, 5*d*, 5*e*, 5*f*, 5*g* and 5*h*).

These peptides are designated as the VR1 and VR2 epitopes. In the P1.7,16 strain, the sequence YYTKNTNNNL (SEQ ID NO:18) is present, the change D to N at residue 180 does have some effect on reducing antibody binding. The sequence HYTRQNNTDVF (SEQ ID NO:19) in P1.15 in the same relative position in the protein as the P1.16 epitope and is responsible for binding to the anti-P1.15 monoclonal antibody. AQAANGGASG (SEQ ID NO:20) shows some binding and peptides 1–3 amino acids downstream show far greater binding to the P1.7 monoclonal antibody. Sequence HFVQQTPQSQP (SEQ ID NO:21) of VR2 is responsible for binding to the anti-P1.2 monoclonal antibody. It is probable that the sequences QPQVTNGVQGN (SEQ ID NO:22) and PPSKSQP (SEQ ID NO:23) in the P1.16 and P1.15 proteins also represent epitopes.

EXAMPLE 6B

Class 1 OMP Constant Region Epitope Identification

Peptides forming surface loops were prepared and conjugated to tetanus toxoid. A BIOLYNX 4170 automated peptide synthesizer (Pharmacia/LKB) was used for continuous flow solid-phase synthesis with the following exception. In the last cycle of the synthesis SAMA-OPfp (0.5 mmol) (Drijfhout, J. W. (1989), *Ph.D. Thesis*, Leiden, The Netherlands) was coupled in the presence of 1-hydroxybenzotriazole (0.5 mmol) for 30 min., using a standard protocol with omission of the piperidine-treatment (i.e. the "Fmoc-deblocking step" which in this case would cause undesirable S-deacetylation). These are referred to as SAMA-peptides.

The peptides and their surface region location which were conjugated to TT are as follows:

| Name | Peptide | | Region |
|---|---|---|---|
| LBV 017 | 176<br>XGGYYTKDTNNNL | 185 | P1.16, loop 4<br>(SEQ ID NO:24) |
| 018 | 24<br>XGGAQAANGGASG | 33 | P1.7, loop 1<br>(SEQ ID NO:25) |
| 024 | 276<br>XGGLSENGDKAKTKNSTTE | 291 | P1.16, loop 6<br>(SEQ ID NO:26) |
| 025a | XGGNAFELFLIGSATSDEAKG | 245 | P1.16, loop 5<br>(SEQ ID NO:27) |
| 025b | 223<br>XANVGRNAFELFLIGSATSDEAKG | | P1.16, loop 5<br>(SEQ ID NO:28) |
| 026 | 124<br>XGGDSNNDVASQLQIFK | 137 | P1.16, loop 3<br>(SEQ ID NO:29) |
| 027 | XADLNTDAERVAVNTANAHPV | | Class 2, loop 5<br>(SEQ ID NO:30) |
| 028a | XGGGKKGENTSYDQ | 329 | Class 1, loop 7<br>(SEQ ID NO:31) |
| 028b | 317<br>XGGERGKKGENTSYDQ | | Class 1, loop 7<br>(SEQ ID NO:32) |
| 029 | XGGVKDAGTYKAQGGKSKTATQ | | Class 2, loop 1<br>(SEQ ID NO:33) |
| 030 | 78<br>XGGWSVAEGGASQVGN | 90 | P1.16, loop 2<br>(SEQ ID NO:34) |
| 031 | 352<br>XKRNTGIGNYTQINAA | 366 | P1.16, loop 8<br>(SEQ ID NO:35) |
| 032 | 16<br>XGGNIQAQLTEQPQVTNGVQGN | 34 | P1.16, loop 1<br>(SEQ ID NO:36) |

Conjugation of SAMA-peptides to tetanus toxoid was performed as follows. A solution of N-succinimidyl bromoacetate (4.7 mg, 10 µmol) in DMF (100 µl) was mixed with a solution of tetanus toxoid (TT) (20 mg) in 0.1 M sodium phosphate buffer pH 7.8 (3.5 ml). After 1h, 1.8 ml of the reaction mixture was subjected to gel filtration using a SEPHADEX PD-10 column (Pharmacia) equilibrated in 0.1 M sodium phosphate, containing 5 mM EDTA (PE buffer) pH 6.1. The bromoacetylated tetanus toxoid was eluted with the same buffer and collected in 3.5 ml. The solution of bromoactylated tetanus toxoid (1.2 ml) was added to the SAMA peptide (4.5 mg, 3 µmol) and deaerated with helium. Next, 150 µl of 0.2 M hydroxylamine (in PE buffer, pH 6.1) was added. After 16 h remaining bromoacetyl groups were blocked by addition of 2-aminoethanethiol hydrochloride (4 µmol) in buffer, pH 6.1 (150 µl). After a further period of 16 h, the peptide-TT conjugate was purified by gel filtration over a PD-10 column using PE buffer, pH6.1, as the eluant. The appropriate fractions were combined and stored at 4° C.

To determine the immunological activity, 25 µg (total protein) per dose of a peptide-TT conjugate was injected subcutaneously at weeks 0 and 4 into 6–8 week old NIH outbred mice. (Note: Vaccine LBV 017-TT and LBV 018-TT were used at 10 µg total protein/dose.) Sera were collected 6 weeks following the first dose and evaluated for antibody response in an ELISA assay (Beuvery, E. C. et al. (1983) *Infect. and Immun.* 40:369–380). The following antigens were coated into the microtiter wells: outer membrane protein (OMP), purified Class I OMP (Poolman, J. T. et al., (1989) *Infect. and Immun.* 57:1005) and the unconjugated peptides. Bactericidal activity (BC) of sera was also measured (Poolman, J. T. et al., (1985) supra.)

The results are presented in Table 2 below.

TABLE 2

| Vaccine | OMC | Class 1 OMP | Synth. Peptide | Bactericidal Test |
|---|---|---|---|---|
| LBV 018-TT | 1:900 (0.05)* | 1:2700 | ND | <1:64 |
| LBV 017-TT | 1:900 (1) | 1:900 | ND | <1:64 |
| LBV 024-TT | 1:100 | 1:100 | 1:900 (homol.) | <1:64 |
| LBV 025a-TT | — | 1:100 | 1:2700 (homol.) | <1:64 |
| LBV 025b-TT | 1:2700 (4) | 1:300 | 1:8100 (homol.) | <1:64 |
| LBV 026-TT | — | — | — (homol.) | <1:64 |
| LBV 027-TT | — | 1:300 | 1:300 (homol.) | <1:64 |
| LBV 028a-TT | 1:100 | — | 1:2700 (homol.) | <1:64 |
| LBV 028b-TT | 1:100 | 1:100 | 1:900 (homol.) | <1:64 |
| LBV 029-TT | — | 1:100 | 1:8100 (homol.) | <1:64 |
| LBV 030-TT | — | 1:100 | 1:2700 (homol.) | <1:64 |
| LBV 031-TT | — | 1:100 | — (homol.) | <1:64 |
| LBV 032-TT | — | 1:100 | 1:900 (homol.) | <1:64 |

*numbers in ( ) indicate O.D. level showing this titer

These data suggest that of the constant surface loops tested of Class 1 and 2 OMPs of *N. meningitidis* loop 5 appears to represent at least one region that will produce antibodies which will cross-react with Class 1 and Class 2 OMP of many strains of *N. meningitidis*.

EXAMPLE 7

Construction of Recombinant Flagellins Expressing meningococcal Epitopes

To create hybrid flagella containing epitopes from class 1 meningococcal epitopes, a series of oligonucleotides was designed based on primary protein sequence data and epitope mapping data. Two oligonucleotides based on VR1 or VR2 epitopes of outer membrane P1.7.16 were designed so that they could be cloned in single or multiple copies into a cloning region within the gene for *S. muenchen* flagellin.

Translation termination signals were included on the non-coding strand of the oligonucleotide to facilitate screening by expression of the cloned inserts.

The plasmid vector pPX1650 containing the entire coding region and promoter regions for the structural gene for flagellin H1-d of *Salmonella meunchen* (deposited at the ATCC, accession #67685) was modified to contain several unique cloning sites suitable for the insertion of either oligonucleotides or gene fragments in each of the three reading frames of the flagellin gene (FIG. 6; see also SEQ ID NOs 182–188). First, pPX1650 was digested with EcoRV, which cleaves pPX1650 twice, 48 base pairs apart, and religated to yield a plasmid, pPX1651, which has a unique EcoRV cloning site and which results in a 16 amino acid deletion in the flagellin protein. pPX1651 was identified by screening *E. coli* recombinants on Western blots probed with polyclonal antibody directed against H1-d flagellin. pPX1651 was identified amongst several candidates having flagellins smaller than wild type flagellin (of 1650) and was verified by sequencing. Second, pPX1651 was restricted with BamH1 and religated after filling out the overhanging ends with Klenow enzyme to remove the unique BamH1 restriction enzyme site in the polylinker region of the vector. As a final step, the resulting vector was digested with EcoRV and the following oligonucleotide linker was inserted:

```
                                  (SEQ ID NO:37)
5'   ATG ATC GAT GGA TTC   3'
3'   TAG TAG CTA CCT AAG   5'
```

Candidates were screened for the newly created BamH sites and several candidates having BamH1 sites were screened for orientation of the linker by double strand DNA sequencing methodology. One candidate having the linker in the above orientation was retained as pPX1647:

```
                                  (SEQ ID NO:38)
5' . . . GAT ATC ATC GAT GGA TTC ATC
         EcoRV      Cla1    BamH1
```

Plasmid pPX1647 (FIG. 6) was digested with BamH and either oligonucleotides for VR1 or VR2 were cloned into *E. coli* cells. Screening for desired recombinants was accomplished by digesting plasmid minilysate DNA with appropriate diagnostic restriction enzymes and screening for expression by probing hybrid flagella for decreased mobility on SDS-PAGE gels with specific flagellar antiserum (H1-d). A number of the resultant clones showed decreased mobility on SDS-PAGE, indicating proper insertion of one or more of the oligonucleotides for VR1 or VR2. Several of each were retained for analysis by DNA sequencing. Clone CB1-2 results from tandem insertion of two copies of the VR1 oligonucleotide and clone CB1-4 results from insertion of four oligonucleotides. Likewise CB2 P contained a single insert of the VR2 oligonucleotide and CB2 W showed the expected trimeric insert, CB2 P clone contained a single base pair change which resulted in a change from Leu to Phe in the expressed VR2 fusion protein and was not retained for further study. The recombinant flagellin clones in *E. coli* were probed with monoclonal antibodies (Abdillahi and Poolman, Microbiol. Pathogenesis 4:27–32, 1988; RIVM, The Netherlands) known to react with either VR1 or VR2 epitopes. Monoclonals Adam-1 (P1.7) and Mn14-C11-6 (P1.7) react with hybrid flagellin containing 2 or 4 tandem inserts of VR1, but do not react with clones containing VR2. The weaker reaction of both monoclonals with CB1-2 than with CB1-4 is likely due to epitope density. By the same token, monoclonals 62 (P1,16) and Mn5-c11-G (P1.16) react with CB2 W clone, but not with the VR1 inserts. The CB2 P clone fails to react with either VR2 antibody, probably due to the Leu to Phe change.

Each of these clones was transformed into an aroA *S. dublin* strain (SL5927), having a Tn10 insertion in the H1-d locus, to examine the functioning of the hybrid flagella. Each of the four clones resulted in motile bacteria; motility of the transformants was inhibited by the corresponding monoclonal antibody, including clone CB2 P, indicating affinity of the VR2 monoclonal for the epitope in intact flagella. This result indicates that epitopes are exposed at the cells surface and are accessible to antibody.

Hybrid flagellin containing both VR1 and VR2 epitopes were created by cleaving either GB1-2, CB1-4, or CB2 W with BamH1 and cloning the heterologous epitope. Clones CB12-7 and CB12-10 result from the in-frame insertion of a single copy of the VR2 oligonucleotide behind either 2 or 4 VR1 tandem inserts, respectively; clone CB21-F arose from the insertion of one copy of the VR1 epitope behind 3 tandem copies of VR2. CB12-7 and CB12-10 are recognized only by VR1 monoclonal antibody and CB21-F is recognized only by VR2 monoclonal. These results, taken together with DNA analysis revealing predicted sequences, indicate epitope density is too low in the combined hybrids. To create a hybrid flagellin with increased density of both VR1 and VR2 epitopes, CB12-10 was digested with BamH1 and VR2 encoding oligonucleotides were inserted. Clone 12-10-6 contains two further tandem inserts of the VR2 epitope, resulting in a hybrid flagellin molecule in which four tandem copies of VR1 are followed by three copies of VR2. As is shown in FIGS. 3A and 3B, three of the hybrid flagellin vaccine candidates have the expected molecular properties. The flagellin (pCB1×4) containing 4 copies of VR1 reacts with anti-H1-d (anti-flagellin) and anti-VR1 monoclonal antibodies, but not with anti-VR2 monoclonal antibodies; the flagellin (pCB2-W) containing 3 tandem copies of VR2 reacts with anti-H1-d and anti-VR2 antibodies, but not with anti-VR1; the combined hybrid containing copies of VR1 and 3 copies of VR2 reacts with both anti-VR1 and anti-VR2 monoclonal antibodies. The combined hybrid specified motility when introduced into a non-motile recipient *S. dublin* strain.

As a subunit vaccine, the goal is to obtain suitable initial vaccine candidates in high quantity and high purity. A suitable vaccine candidate can be chosen from the above type constructions based on reactivity to monoclonal antibodies and function of flagella in non-motile *Salmonella* host strains. A subunit flagellin vaccine may not need to retain all functional aspects of a parental flagellin, but should at least retain surface localization for purification purposes. Several subunit flagellin meningococcal vaccine were chosen from the above described hybrid molecules based on reactivity to monoclonal antibodies and implied surface localization based on restoration of bacterial motility.

Three flagellin vaccine candidates contained either 4 tandem inserts of VR1, 3 tandem inserts of VR2, or 4 VR1 inserts followed by 3 VR2 inserts. Because flagellin is a major protein of *Salmonella,* it is possible to easily purify sufficient material for vaccination studies using techniques established for flagella purification (Logan et al., J. Bacteriol. 169: 5072–5077, 1987).

EXAMPLE 8

Initial Purification of Recombinant Flagellin Molecules

The three hybrid flagellin vaccine candidates and a wild type (derived from pPX1650) were inoculated into four-liter baffled Fernbach flasks containing 1 liter of LB broth. Bacterial cultures were incubated at 37° C. with shaking (200 rpm) for 22–24 hr. Under these conditions of culturing, the bulk of the flagella were sloughed from the bacterial cell surface and were localized in the supernatant culture medium. To obtain suitable material, flagella were isolated from 6–8 liters of culture medium. To obtain purified flagellin preparations for vaccination studies, flagellar filaments were harvested from bacterial culture supernatants by the following procedure: Ammonium sulfate was added to culture supernatant so that final solution was 50% saturated; the solution was stirred gently at 4° C. for several hours and the precipitated material was collected by centrifugation in a GSA rotor at 5000 rpm for 30 minutes. The collected ammonium-sulfate precipitated material was reconstituted in PBS and dialyzed against PBS at 4° C. for 12–15 hrs. The dialyzed material was subjected to high speed centrifugation at 100,000×g for 1 hour in an SW-27 rotor to pellet the flagellar filaments. The pelleted material, which consisted primarily of flagellin, was subjected to further purification by the following method.

EXAMPLE 9

HPLC Purification of Recombinant Flagellins

Figure 8:
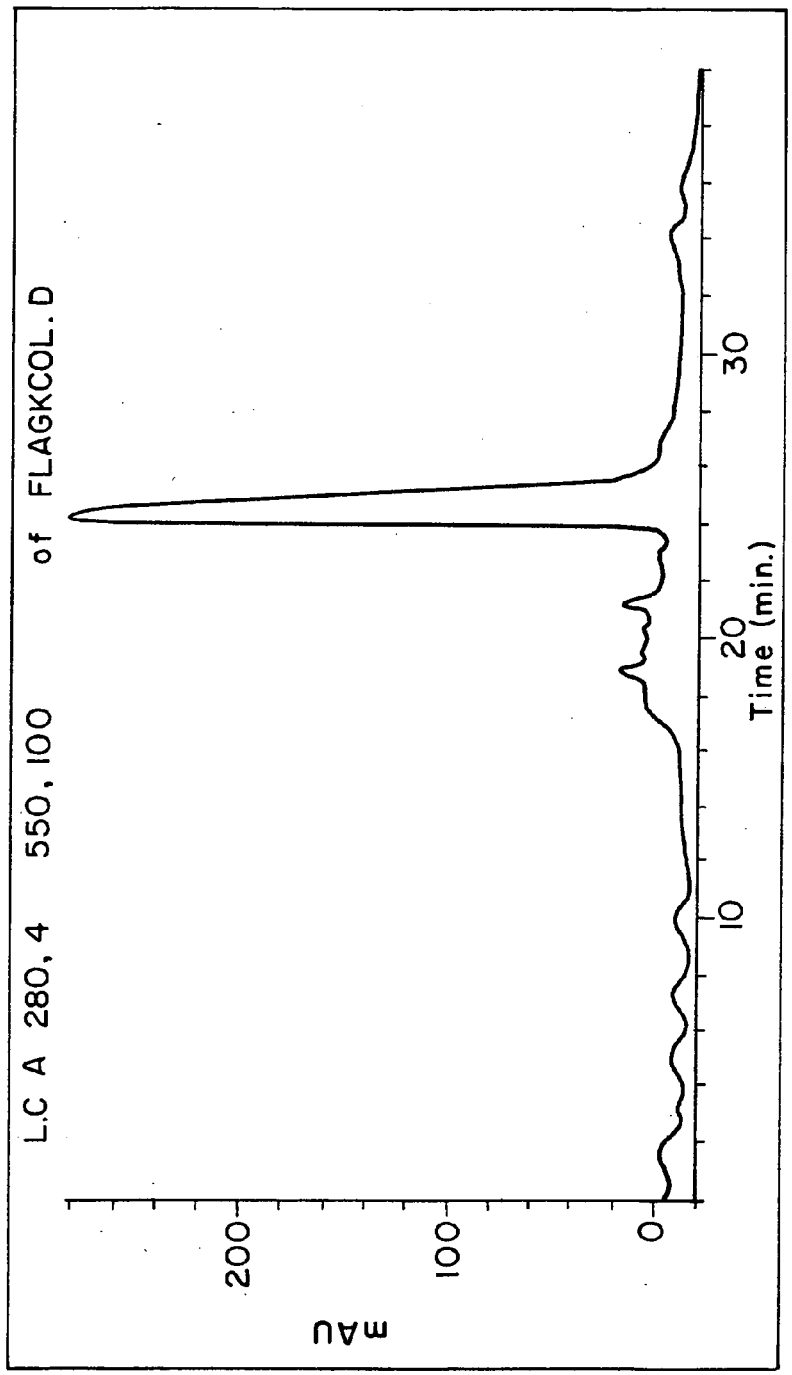
FIG. 8. Representative chromatogram of high performance liquid chromatography of a recombinant flagellin.
Figure 9:
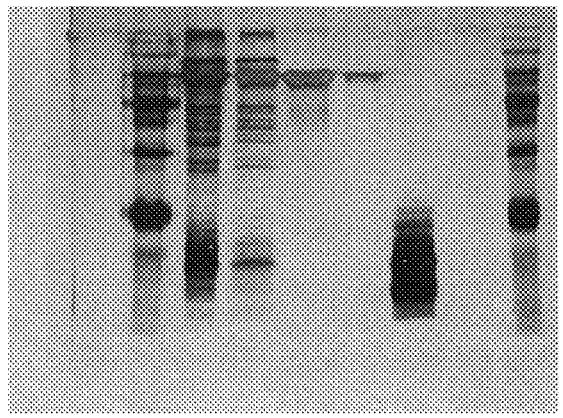
FIG. 9. Representative analysis by SDS-PAGE of recombinant flagellin.
Figure 10:
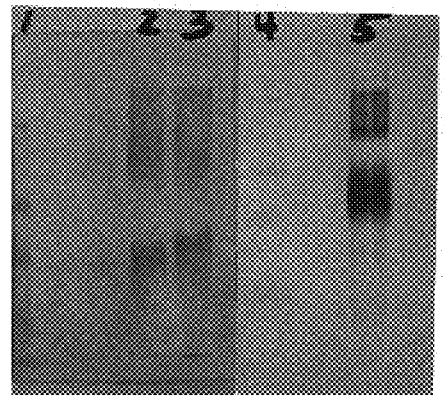
FIG. 10. Regresentative Western blot analyses of a conjugate comprising an epitope of N. meningitidis Class 1 OMP conjugated to CRM 197.

To prepare highly purified flagellins, Salmonella expressing the constructions, in particular pCB12-10-6, was grown as described above and the cells pelleted at 10,000 G. The culture supernatant was then precipitated with 50% ammonium sulfate, centrifuged at 10,000 G and resuspended in 30 ml PBS. The resuspended pellet was dialyzed against 10 mM Tris buffer (pH=8.0) containing 6M urea, 1 mM PMSF, 2 mM NEM, and 5 mM EDTA overnight at 4° C. Dialyzed material was then passed over two DEAE SEPHAROSE minicolumns (3.0 ml volume, 4.0 ml eluent over each). The columns were eluted (5×) with 50 mM NaCl in 10 mM tris (pH=8.0) containing 6M urea and then with 1M NaCl in 10 mM tris (pH=8.0) containing 6M urea. The first four elution collections (20 ml) of the 50 mM NaCl were pooled and dialyzed against 1.0 liter 10 mM acetate buffer (pH=4.0) in 6M urea at room temperature. The dialyzed fractions were then loaded onto a TSK SP PW cation exchange HPLC column (75 mm×300 mm). The column was eluted with a mobile phase consisting of 10 mM acetate (pH=4.0) containing 6M urea. A gradient 0–300 mM NaCl was established in 10 mM acetate (pH=4.0) containing 6M urea over the 5–30 min interval. After 30 mins the gradient went from 300 mM to 1M NaCl in 10 mM acetate in 6M urea over the next 5 min. The flagellin construct was collected at approximately 24 min. which corresponds to about 200 mM NaCl. The fraction was dialyzed against PBS and purity determined on the material was established by Western blots using anti-flagellin antibody. A representative HPLC analysis and SDS-PAGE are shown in FIGS. 8 and 9 respectively.

EXAMPLE 10

Preparation of Meningococcal-Flagellin Glycoconjugate

Group C meningoccal capsular polysaccharide (GCM CPS: lot # 86 NM 01) was prepared essentially according to Bundel et al., *J. Biol. Chem.* 249: 4797–801, 1974).

Neisseria meningitidis strain C11 was obtained from the Walter Reed Army Institute (Washington, D.C.). The strain was precultured twice on sheep blood agar plates, then used for the inoculation of a liquid seed culture medium *Neisseria* chemically defined medium, NCDM (Kenney et al., Bull. W. H. O. 37 469–73, 1967). Finally 40 l of liquid medium (NCDM) in a fermentor was inoculated with the liquid preculture. The purity of the strain was checked at each stage. After centrifugation, the supernatant was precipitated by addition of CETAVLON to a final concentration of 0.1%, and the insoluble complex re-dissolved in cold 1 M calcium chloride ($CaCl_2$) (Gotschlich et al., *J. Exp. Med.* 129: 1349–65, 1969). Ethanol (96%) was added to a final concentration of 25% (v/v). After 1 h, the suspension was centrifuged (1 h, 50,000 g), the supernatant was collected, and its ethanol concentration was increased to 80% (v/v). After 1 h, centrifugation (20 min, 5,000 g) yielded a precipitate which was washed successively with absolute ethanol, acetone and diethylether, and then dried in a vacuum dessicator over phosphorus pentoxide ($P_2O_5$) to constant weight. This crude CPS was stored at –20° C.

In order to obtain a purer preparation, the CPS was then dissolved in sodium acetate buffer (1.10 dilution of a saturated solution, pH 7.0) and extracted four times wiht hot phenol (Westphal et al., *Z. Naturforsch.* 7b:148–55, 1952). After dialysis of the combined aqueous phases against 0.1 M $CaCl_2$, followed by centrifugation (3–5 h, 100,000 g), a final ethanol precipitation was performed on the clear supernatant, and the resulting precipitate washed with organic solvents and dried, as described above. The pure CPS was then stored at –20° C.

At each stage of the purification process, the CPS was analyzed for carbohydrate N-acetyl-neuraminic acid, NANA) (Svennerhold, *Biochim. Biophys. Acta* 24:604, 957), O-acetyl (Hestrin, *J. Biol. Chem.* 180:249, 1949), and protein (260 nm detection) content, and its molecular weight checked by gel filtration.

Group C meningococcal capsular polysaccharide (GCM CPS) was simultaneously depolymerized and activated via sodium periodate ($NaIO_4$) oxidation in aqueous buffer (Anderson et al., *J. Immunol.* 137:1181–6, 1986; Eby et al., Pediat. Res. 20:308A, 1986, Anderson et al., *J. Pediatr.* 111(5):644–50, 1987; Anderson, U.S. Pat. No. 4,762,713; 1988). The reaction was monitored by high performance gel permeation chromatography (HPGPC) in aqueous eluent, using ultraviolet (UV) and refractive index (RI) detection. The reaction was stopped and the activated oligosaccharides (GCM OS) were desalted by low pressure gel permeation (GPC) in water, and then lyophilized. A solution was then prepared in water and subsequently frozen for temporary storage. GCM OS and flagellin pCB12-10-6 were mixed in aqueous neutral buffer and the conjugation was initiated by addition of sodium cyanoborohydride ($NaBH_3CN$) (Anderson, U.S. Pat. No. 4,762,713, 1988; U.S. Pat. No. 4,673,574, 1987; U.S. Pat. No. 4,761,283, 1988). The reaction was carried out for 5 days, while being monitored by HPGPC. It was finally stopped by dialysis/concentration on centrifugal microconcentrators. The final preparation was stored in the cold, in the presence of thimerosal to prevent bacterial growth. The resulting glycoconjugate not only provides a mechanism to present the expressed VR1 and VR2 meningococcal epitopes to the immune system but also serves as a carrier molecule for the presentation of a meningococcal oligosaccharide.

In preparation of the conjugate, the following conditions were employed. Purified flagellin pCB12-10-6 was dissolved in 15% sucrose (3.5 mg/ml) and then stored at −20° C. GCM CPS (9.7 mg; final concentration: 5 mg/ml) was oxidized by 100 mM $NaIO_4$ in 0.05 M sodium phosphate buffer (pH 6.2–6.5) at RT, in the dark, with agitation. Aliquots (100 μl) were withdrawn at regular intervals, the reaction stopped by addition of ethylene glycol (10 μl), and analysis was performed by HPGPC on Waters (Milford, Mass.) Ultrahydrogel™ 250+120 (2 columns coupled; 2×300 mm×7.8 mm) in 0.2 M phosphate-saline buffer (PBS; 0.2 M sodium phosphate, 0.9% NaCl, pH 7.8), at a flow rate of 0.8 ml/min, using UV (206 nm) and RI detection. After 2 h 30 min, the reaction was stopped by addition of ethylene glycol (1/10 of the reaction volume), and the GCM OS were desalted by GPC on Bio-Rad (Richmond, Calif.) Bio-Gel® P-2 (200–400 mesh, 30 cm×1.5 cm) in water, at about 18 ml/h. Fractions were collected (1.2 ml) and analyzed for the presence of NANA the carbohydrate N-acetyl-neuraminic acid (NANA) (Barry et al., *J. Gen. Microbiol.* 29:335–52, 1962) and aldehydes (Porro et al., Anal. Biochem 118: 301–306, 1981). Positive fractions were pooled and lyophilized. Desalted GCM OS (4.7 mg) were then dissolved in water (10 mg/ml) and frozen at −20° C.

Both GCM OS and pCB12-10-6 solutions were analyzed by HPGPC (UV at 206 and 280 nm respectively) before being frozen, and prior to the conjugation. No degradation occurred during storage, as ascertained by the exact similarity of the elution profiles.

GCM OS (2 mg; final concentration: 2.6 mg/ml) and flagellin pCB12-10-6 (2.3 mg; final concentration: 3 mg/ml) were mixed in a polypropylene tube in 0.4 M sodium phosphate buffer (pH 7.0), and $NaBH_3CN$ was added (12 μmoles) to initiate the conjugation (Anderson, U.S. Pat. No. 4,762,713, 1988; U.S. Pat. No. 4,673,574; U.S. Pat. No. 4,761,283). The reaction mixture was left one day at RT, then 4 days at 35° C., without agitation. The reaction was monitored by HPGPC (UV at 280 nm) at different stages, and finally stopped by dialysis/concentration on microconcentrators. The final preparation was analyzed for NANA (Barry et al., J. Gen. Microbiol. 29:335–353, 1962) (0.09 mg at 0.12 mg/ml) and protein (Lowry et al., J. Biol. Chem. 193:265–275, 1951) (1.12 mg; 1.45 mg/ml) content. It was then stored at 4° C. in the presence of thimerosal (0.01%, w/v) to prevent bacterial growth.

The conjugate preparation was also checked by SDS-PAGE (silver nitrate stain) and Western blots analyzes. Several high molecular weight bands appeared on the gel above the pure pCB12-10-6 band and near the stacking well, the latter being an evidence that cross-linking occurred during conjugation. Western blot analyzes showed that each band was reactive with the antisera used (anti-GCM, −VR1 and −VR2), proving covalency of the conjugate bonds.

EXAMPLE 11

Conjugation of Meningococcal Peptides to CRM and Bovine Serum Albumin

Peptides designated as M20 and M21 were produced on an ABI model-peptide synthesizer by solid phase synthesis using the tBoc chemistry were coupled to $CRM_{197}$ (prepared as described by Anderson, U.S. Pat. No. 4,762,713) using a bifunctional crosslinking agent, sulfosuccinimidyl (4-iodoacetyl) amino benzoate (Sulfo SIAB; purchased from Pierce) following the modification of a published procedure (Weltman, J. K. et al., (1983) Bio Techniques 1, 148–152). Briefly $CRM_{197}$ was activated by sulfo SIAB resulting in the formation of an amide bond between SIAB and amino groups of $CRM_{197}$. After the removal of unreacted crosslinker from the activated $CRM_{197}$ by gel filtration, peptide (M20 or M21) containing linking spacer (represented in underlined letters) with carboxy terminal cysteine residue was mixed with activated CRM and incubated at room temperature for 2–4 hours. Following the reaction, the conjugated material was dialyzed extensively against PBS at 4 C.

The sequence of M20 peptide (VR2 epitope) is as follows:

```
                                      (SEQ ID NO:39)
H-Tyr-Tyr-Thr-Lys-Asp-Thr-Asn-Asn-Asn-Leu-Thr-Leu-
Val-Pro-Ala-Gly-Ala-Cys-OH
```

The sequence of M21(VR1 epitope) peptide is:

```
                                      (SEQ ID NO:40)
H-Ala-Gln-Ala-Ala-Asn-Gly-Gly-Ala-Ser-Gly-Gln-Val-
Lys-Ala-Gly-Ala-Cys-OH.
```

Conjugated materials were subjected to SDS PAGE, transferred to PVDF membranes (IMMOBILON, Millipore) and reacted with specific monoclonals which recognized VR1 and VR2 epitopes. FIGS. 10*a* and 10*b* show the western blot analysis of M20 and M21 $CRM_{197}$ conjugates, against a pool of VR1 and VR2 specific monoclonals (Adam I, G2-D12-8 (P1.7), MN5-C11-G (P1.16) and MN14-C11-6 (P1.7)).

In order to assay the antibody response to M20 and M21 peptide by enzyme linked immunoassay procedure, BSA conjugates were prepared by using a different bifunctional crosslinking agent, N-Succinimidyl Bromoacetate as described by Bernatowicz and Matsueda (Anal. Biochem. 155, 95–102 (1986)). Covalent coupling of peptide to the protein was confirmed by western blotting of electrophoresed samples as described for $CRM_{197}$ conjugates.

EXAMPLE 12

Retention of T Cell Activity by M20 and M21-$CRM_{197}$ Conjugates

To determine whether conjugation of the VR1 and VR2 epitopes to $CRM_{197}$ adversely affect the T cell recognition of the $CRM_{197}$ protein a T cell proliferative assay was performed as previously described by Bixler and Atassi (Immunol. Commun. 12:593, 1983). Briefly, SJL/j mice were immunized with 50 μg of native CRM197 emulsified in CFA. Seven days later, lymph nodes were removed, cultured in RPMI and challenged with various concentrations of proteins (0.05–100.0 μg/ml) and peptides. After 3 days incubation, cultures were pulsed with [$^3$H]-thymidine for 16 hours and then harvested for counting.

TABLE 3

T cell responses to meningococcal peptide-CRM197 conjugates.

| In Vitro Challenge | μg/ml | Maximum observed [³H] Incorporation ΔCPM | SI |
|---|---|---|---|
| Diphtheria toxoid | 5 | 27,510 | 57 |
| CRM197 | 50 | 108,631 | 221 |
| CRM197 - mock conjugate | 100 | 116,326 | 236 |
| M21-CRM197 | 100 | 182,499 | 370 |
| M20-CRM197 | 10 | 89,972 | 183 |
| CON A | 1 | 34,316 | 70 |
| LPS | 50 | 61,579 | 126 |
| Tetanus toxoid | 10 | 515 | 2 |
| Background (cpm) | — | 494 | 1 |

As shown in Table 3, a comparison of $CRM_{197}$ with the $CRM_{197}$-mock conjugate shows that the conjugation procedure by itself did not alter the T cell recognition of the protein. The T cell responses induced by the M20 and M21-$CRM_{197}$ conjugates were essential equivalent to or greater than the response elicited by $CRM_{197}$ itself indicating that the recognition of the T cell epitopes on the $CRM_{197}$ is not adversely affected by the peptide conjugation. The responses to the control materials Con A, LPS and Tetanus toxoid were as expected.

EXAMPLE 13

Immunogenicity of Conjugate and Recombinant Meningococcal B Vaccines

Recombinant flagellin expressing the meningococcal VR1 and/or VR2 epitopes were prepared and purified as described in Examples 7, 8 and 9. In addition, synthetic peptides representing the meningococcal epitopes VR1 and VR2 were synthesized, covalently coupled to the carrier molecule $CRM_{197}$ and purified as in Example 12. Vaccines were formulated with each of these materials at protein concentrations of 10 or 100 μg/ml for each of the components. The vaccine compositions also included aluminum phosphate at 1 mg/ml or except as noted were compounded with Freund's complete adjuvant or without supplemental material.

To evaluate immunogenicity, outbred Swiss Webster mice were immunized intramuscularly at weeks 0 and 2 with 1 or 10 μg protein/dose. Sera were collected at two week intervals, pooled for assay, and screened for antibody activity by ELISA to outer membrane complex (OMC), purified OMP (P1.16), VR1 peptide coupled to Bovine serum albumin (M21-BSA), VR2 peptide coupled to BSA (M20-BSA), wildtype flagellin, and to $CRM_{197}$. The results of the ELISA performed on sera obtained at 6 weeks are shown in Table 4.

TABLE 4

Immunogenicity of recombinant or CRM197 conjugate vaccines containing the meningococcal P1.16 OMP epitopes VR1 and VR2.

| DOSE μg | ELISA TITERS 4 WEEKS AFTER SECONDARY BOOST[1] | | | | | |
|---|---|---|---|---|---|---|
| | OMC | P1.16 | M21-BSA | M20-BSA | FLAG-ELLIN | CRM |
| pPx1650 (control wildtype flagellin)[2] | | | | | | |
| 1 | <150 | <100 | 171 | 100 | 427,781 | ND |
| 10 | <150 | 100 | 154 | <100 | 468,385 | ND |
| pCB1-4 | | | | | | |
| 1 | 532 | 4,376 | 4,525 | ND | 787,120 | ND |
| 10 | 2,034 | 12,387 | 17,565 | ND | 887,861 | ND |
| pCB2-W | | | | | | |
| 1 | 150 | 308 | ND | 501 | 263,143 | ND |
| 10 | 1,350 | 12,190 | ND | 5,476 | 1,493,216 | ND |
| pCB12-10-6 | | | | | | |
| 1 | 615 | 3,374 | 4,651 | 824 | 299,889 | ND |
| 10 | 1,423 | 3,666 | 3,882 | 2,253 | 497,622 | ND |
| pCB12-10-6 without aluminum phosphate | | | | | | |
| 1 | 409 | 739 | 505 | 597 | 139,147 | ND |
| 10 | 450 | 1,533 | 817 | 1,611 | 358,033 | ND |
| M20-CRM197 | | | | | | |
| 1 | <150 | <100 | 217 | <100 | ND | 42.27 |
| 10 | 50 | <100 | 150 | <100 | ND | 95.31 |
| M21-CRM197 | | | | | | |
| 1 | 68 | 249 | 10,494 | 100 | ND | 17.41 |
| 10 | 110 | 311 | 26,807 | 191 | ND | 20.92 |
| MIXTURE OF M20 AND M21 CONJUGATES | | | | | | |
| 1 | 50 | 100 | 40,000 | 187 | ND | 37.32 |
| 10 | 50 | 227 | 15,539 | 132 | ND | 184.27 |
| OMP P1.16 | | | | | | |
| 1 | 12,630 | 17,714 | 100 | 764 | ND | ND |
| 10 | 23,178 | 67,565 | 162 | 3,276 | ND | ND |
| pCB1-4 in CFA | | | | | | |
| 10 | 1,665 | 10,606 | 19,945 | ND | 1,841,852 | ND |
| pCB2-W in CFA | | | | | | |
| 10 | 1,157 | 6,869 | ND | 17,749 | 1,217,063 | ND |

[1] All pre-bleed values at or below the lower limit of assay of 1/100 dilution.
[2] All vaccines were formulated with 1 mg/ml aluminum phosphate except as noted.

Alternatively, the various vaccines were evaluated for immunogenicity in 6–8 week old NIH outbred mice. The mice were immunized with 100 μg (total protein)/dose subcutaneously on week 0 and 4 with vaccine and sera was collected on week 6. The sera were evaluated in an ELISA assay and using antigens as described in Example 6. Bactericidal activity was measured as in Example 6. The results are found in Table 5.

TABLE 5

| Vaccine | ELISA (titer > 0.5 OD) | | | | Bactericidal Test |
|---|---|---|---|---|---|
| | FLAGELLIN | OMC | Class 1 OMP | Synth. Peptide | |
| p1650 | — | — | — | — | <1:64 |
| pCB12.10.6 | — | — | 1:900 | — | <1:64 |
| pCB2-W | — | — | 1:300 | 1:100 | <1:64 |
| pCB1-4 | 1:300 (.25) | — | 1:2700 | — | <1:64 |
| CRM197 | — | — | — | — | <1:64 |
| M20-CRM197 | 1:00 | — | 1:8100 | — | <1:64 |
| M21-CRM197 | 1:300 (.125) | — | 1:8100 | — | <1:64 |

The recombinant flagellins containing either a VR1, VR2 or a cassette of both VR1 and VR2 were effective in eliciting an antibody response which was cross-reactive to the purified P1.16 and to a lesser extent to OMC. Sera from animals immunized with 10 µg of either pCB1-4 or pCB2-w induced antibodies which bound to their respective peptide-BSA conjugates as well as cross reacted with the P1.16 and OMC. Similar results were obtained with the constructed pCB12-10-6 which contains both meningococcal epitopes. In addition, each construction induced significant anti-flagellin titers as well. In contrast, the control wildtype flagellin only induced an antibody response to flagellin itself. Sera collected prior to immunization showed no pre-existing response to the materials being evaluated.

The data also demonstrates the benefits of formulating the recombinant flagellins with alum or other adjuvants such as CFA. The construction pCB12-10-6 was formulated with and without the addition of aluminum phosphate. As shown in table 2, pCB12-10-6 alone was capable of inducing an antibody response which react to the peptide conjugates as well as to the purified P1.16 as well as to OMC. In comparison, the same construction when formulated with alum was able to elicit greater antibody response at an equivalent dose. Similarly, the recombinant flagellins pCB1-4 and pCB2-w were also formulated with CFA. Again, equivalent or higher antibody titers were observed in the presence of CFA.

The results of the immunogenicity studies with the meningococcal VR1 and VR2 conjugates are also shown in Table 4. Both the M20 and the M21-CRM$_{197}$ conjugates as well as a mixture containing equal amounts of both conjugates were capable of inducing an anti-CRM$_{197}$ response as well as an anti-Class 1 OMP response.

These preliminary data indicate a Class 1 OMP variable region epitopes either chemically conjugated to a carrier or genetically fused to a carrier elicit an immune response. New epitope-carrier conjugates can be made using standard techniques to enhance the immune response to the vaccine, for example, use of 1) larger epitopes, 2) peptides with multiple epitope repeats and/or 3) different carriers.

EXAMPLE 14

Preparation of Meningoccal-Human Serum Albumin Glycoconjugate

GCM CPS was depolymerized by acid hydrolysis and GCM OS obtained were subsequently activated via NaIO$_4$ oxidation in aqueous buffer. The reactions were monitored by HPGPC in aqueous eluent, using UV and RI detection. The reactions were each followed by GPC desalting in water. GCM OS and human albumin (HA) were mixed and conjugated essentially as described in Example 10 for the meningococcal flagellin glycoconjugate. The final preparation was stored in the cold, in the presence of thimerosal to prevent bacterial growth.

In preparation of the conjugate, the following experimental conditions were employed. Human albumin (HA; Sigma®, St. Louis, Mo.) was dissolved in 15% sucrose (10 mg/ml) and then stored at −20° C. GCM CPS (lot # 86 NM 01; 106 mg; final concentration: 10 mg/ml was hydrolyzed in 0.1 N HCl at 50° C. with agitation. Aliquots (25 µl) were withdrawn at regular intervals, the reaction stopped by addition of sodium hydroxide (NaOH) and analysis was performed by HPGPC as described. After 3 h 40 min., the reaction was stopped by addition of NaOH, and the GCM OS were desalted by GPC. Fractions were collected (1.2 ml) and analyzed as described before. Positive fractions were pooled and lyophilized. Desalted GCM OS (89 mg) were then stored at −20° C. Activated OS were prepared by oxidation of GCM OS (11.8 mg; final concentration: 5 mg/ml) with 2 mM NaIO$_4$ in 0.05 M sodium phosphate buffer (pH 6.2–6.5) at RT, in the dark, with agitation. The reaction was stopped after 30 min by addition of ethylene glycol. HPGPC analyzes showed no degradation of the molecular weight of the OS during activation. Desalting and colorimetric anaylzes were then performed as described above. The resulting activated GCM OS (8.8 mg) were dissolved in water (10 mg/ml) and frozen at −20° C.

Both GCM OS and HA solutions were analyzed by HPGPC (UV at 206 and 280 nm respectively) before being frozen, and prior to the conjugation. No degradation occurred during storage, as ascertained by the exact similarity of the elution profiles.

GCM OS (6 mg; final concentration: 2.5 mg/ml) and HA (12 mg; final concentration: 5 mg/ml) were mixed in a polypropylene tube in 0.4 M sodium phosphate buffer (pH 7.0), and NaBH$_3$CN was added (60 µmoles) to initiate the conjugation (Anderson, U.S. Pat. No. 4,762,713, 1988; U.S. Pat. No. 4,673,574, 1987; U.S. Pat. No. 4,761,283, 1988). The reaction mixture was left one day at RT, then 4 days 15 35° C., without agitation. The reaction was monitored by HPGPC (UV at 280 nm) at different stages, and finally stopped by dialysis/concentration on microconcentrators. The final preparation was analyzed for NANA (Barry et al., *J. Gen. Microbiol.* 29P335–51, 1962) (2.07 mg at 0.86 mg/ml) and protein (Lowry et al., *J. Biol. Chem.* 193265–75, 1951) (9.51 mg at 3.96 mg/ml) content. It was then stored at 4° C. in the presence of thimerosal (0.01%, w/v) to prevent bacterial growth.

The conjugate preparation was also checked by SDS-PAGE (silver nitrate stain) and Western blot analyzes. A diffuse band appeared on the gel which covered a significantly wider molecular weight range than the pure HA. Western blot analyzes showed that this band was reactive with the antiserum used (anti-GCM), proving covalency of the conjugate bonds.

EXAMPLE 15

Immunogenicity of Meningococcal Oligosaccharide-Recombinant Flagellin Vaccines

A meningococcal oligosaccharide-recombinant flagellin vaccine was prepared as described above and formulated at 100 µg protein/ml. Vaccine compositions were also prepared which contained aluminum phosphate (1 mg/ml) or complete Freund's adjuvant in addition to the glycoconjugate.

To evaluate the immunogenicity, outbred Swiss Webster mice were immunized intramuscularly with 10 µg protein at week 0 and 2. Sera were collected at weeks 0, 2 and then weekly intervals thereafter to 6 weeks. After collection, pooled sera samples were assayed for antibody activity by ELISA to meningococcal C oligosaccharide conjugate to human serum albumin, OMC, P1.16, CB1 and CB2-BSA conjugates and flagellin.

The MenC-CB12-10-6 glycoconjugate was effective at eliciting an immune response which was reactive with both the oligosaccharide and the meningococcal B OMP epitopes expressed in the recombinant flagellin. As shown in Table 5B, as little as three weeks into the study, mice immunized with 1 µg of MenC-CB12-10-6 conjugate in complete Freund's adjuvant had detectable antibody to MenC-HSA, OMP and to both the CB1 and CB2 epitopes. Further, all of the MenC-CB12-10-6 preparations, regardless of adjuvant, elicited antibody response to MenC-HSA which were greater than the response observed following immunization with MenC-CRM197.

TABLE 5B

Immunogenicity of Meningococcal C - recombinant flagellin vaccine one week after secondary immunization.

| IMMUNOGEN | | Dose | ELISA TITERS[1] | | | | |
|---|---|---|---|---|---|---|---|
| | | | MenC-HSA | OMP | CB1-BSA | CB2-BSA | FLAGELLIN |
| MenC-CB12-10-6 | CFA | 10 | 24,530 | 608 | 5,240 | 432 | 541,467 |
| | | 1 | 5,069 | 5,614 | 5,375 | 12,685 | 526,593 |
| | alum[2] | 10 | 11,845 | 253 | 835 | 673 | 472,766 |
| | | 1 | 4,415 | 136 | 242 | 244 | 214,263 |
| | None | 10 | 11,497 | 920 | 626 | 2,382 | 233,307 |
| | | 1 | 4,920 | 483 | 1,123 | 1,210 | 135,625 |
| MenC-CRM197 | alum | 10 | 4,905 | ND | ND | ND | ND |
| | | 1 | 8,505 | ND | ND | ND | ND |
| OMP (P1.16) | alum | 10 | ND | 12,907 | <100 | <100 | ND |
| | | 1 | ND | 10,405 | <100 | 3,377 | ND |

[1]Titers for initial prebleed samples (week 0) samples were <100.
[2]Aluminum phosphate was used as adjuvant at 1 mg/ml.

EXAMPLE 16

T-cell Epitopes of Class 1 OMP and Their Identification

An effective vaccine must contain one or more T-cell epitopes. T-cell epitopes within a protein can be predicted as described by Margalit et al., *J. Immunol.* 138:2213, (1987) or Rothbard and Taylor, *EMBO J.* 7:93, (1988). These predictive methods were applied to the amino acid sequence of the Class 1 OMP of *N. meningitidis* strains P1.7,16, P1.16 and P1.15. The segments of the sequence containing potential T cell epitopes identified by these methods are shown in Tables 6 and 7. The predicted peptides were synthesized by standard FMOC procedures, purified by standard methods and were identified as shown in Table 8.

To determine which of the predicted peptides actually contain T cell epitopes, their capacity to stimulate human peripheral blood lymphocytes (PBL) was tested by lymphocyte proliferative assay. Briefly, peripheral blood was collected from HLA typed normal volunteers or from volunteers who were previously immunized with MPC-2 (Poolman, J. T. et al., *Antonie von Leeuwenhoek*, 53:413–419, 1987) which contained P1.16, 15, Class 4 OMP and Group C polysaccharide. Lymphocytes were isolated from the peripheral blood by isolation on FICOLL-HYPAQUE (Pharmacia Fine Chemicals AB, Uppsala, Sweden) and cultured at $1 \times 10^5$ cells/well in supplemented RPMI 1640 medium (Gibco Laboratories, Paisly, Scotland) containing 10% heat-inactivated pooled human AB serum. Cultures were challenged with various concentrations of the predicted T cell epitopes (0.05–10 μg/ml). After in vitro challenge, the cultures were incubated for six days and then pulsed (18 hours) with 0.5 μCi of [$^3$H]-thymidine. Cultures were then harvested and counted by liquid scintillation. Data are expressed as stimulation indices which were calculated as a ratio of the CPM obtained in the presence of antigen to the CPM obtained in the absence of antigen.

As shown in Table 9, 10 of the 16 predicted peptides showed some capacity to stimulate T-cells. These include the peptides identified at 16–34, 47–59, 78–90, 103–121, 124–137, 151–158, 176–185, 223–245, 276–291 and 304–322. In some instance, peptides stimulated a response in both immunized as well as non-immune individuals. The response in the non-immune individuals may be attributed to a previous asymptomatic infection.

In the case of the T cell epitope identified as region 176–185, enhancement of the T cell response was observed following addition of the monoclonal antibody MN5C11G (P1.16). Briefly, PBL were challenged in vitro with a synthetic peptide containing the region 175–185 or with this peptide mixed with varying dilutions of MN5C11G. As shown in Table 10, enhancement of the T cell response was observed following addition of MN5C11G indicating that monoclonal antibody recognized a B cell epitope within the region 176–185 and facilitates the presentation of the peptide to the immune system. Thus, it was established that the T and B cell epitopes either coincide or are found on contiguous sequences within the Class 1 OMP.

In several cases, T cell lines and clones were established from individuals responding to various peptides. Briefly, T cell lines were obtained by culturing isolated lymphocytes in 24 well plates at $1 \times 10^6$ cells/ml. The culture medium, supplemented RPMI-1640 with 10% human serum, also contained 12 U/ml recombinant IL-2 (Boehringer). In addition, $5 \times 10^4$ homologous, irradiated (3,000 R) antigen presenting cells (APC) were also added to each well. In some cases, APC were obtained from HLA compatible donors. From the lines, T cell clones were isolated by limiting dilution at a frequency of 0.5 cells/well. Clones were maintained by bi-weekly stimulation with antigen in the presence of irradiated APC and IL-2 and IL-2 (2 U/ml). Clones were tested by lymphocyte proliferation assay essentially as described above except that clones were cultured at $1 \times 10^4$ cells/well in the presence of irradiated APC.

Clones obtained as described were challenged in vitro with OMP from 7 different strains of meningococci. As shown in Table 11, the clones recognized a T cell epitope or epitopes common to the seven OMPs examined. Although the reactivity of these clones to the various peptides remains to be determined, the data, nevertheless, does indicate the commonality of T cell epitopes among the various strains. Now that these clones have been established and identified their peptide reactivity will indicate T-cell epitopes for vaccine use.

TABLE 6

ANALYSIS OF THE SEQUENCE OF *N. MENINGITIDIS* P1.16 OMP FOR THE PRESENCE OF AMPHIPATHIC α-HELICIES ACCORDING TO THE METHOD OF MARGALIT ET AL. (J. IMMUNOL. 138:2213, 1987)

|   | MID POINTS OF BLOCKS | ANGLES | AS |
|---|---|---|---|
| P | 47–50 | 85–105 | 9.4 |
|   | 69–74 | 105–135 | 16.0 |
| K | 79–88 | 90–120 | 23.0 |
|   | 127–135 | 100–120 | 22.4 |
| * | 199–202 | 90–120 | 8.4 |
| P | 208–211 | 85–95 | 8.7 |
|   | 260–263 | 90–125 | 8.8 |
| P | 265–269 | 90–120 | 11.3 |
|   | 274–277 | 105–120 | 9.8 |
|   | 297–300 | 100–135 | 9.1 |
| P | 320–324 | 80–100 | 10.9 |
| * | 338–342 | 105–135 | 12.3 |
| * | 346–351 | 80–115 | 11.9 |
| * | 376–379 | 85–120 | 9.5 |

TABLE 7

PRESENCE OF MOTIFS (UNDERLINED REGIONS) REPRESENTING POTENTIAL T CELL EPITOPES WITHIN THE SEQUENCES OF *N. MENINGITIDIS* P1.16 OMP (SEQ ID NO:191) AS DETECTED BY THE METHOD OF ROTHBARD AND TAYLOR (EMBO J 7:93, 1988).

MRKKLTALVLSALPLAAVADVSLYGEIKAGVEGRNI

QAQLTEQPQVTNGVQGNQV<u>KVTKA</u>KSRIRTKISDFG

SFIGFKGSEDLGEGL<u>KAVWQ</u>LEQDVSVAGGGASQWG

NRESFI<u>GLAGE</u>F<u>GTLR</u>AGR<u>RVAN</u>QFDDASQAINPWDS

NN<u>DVASQLGIFK</u>RHDDMPVSVRYDSPEFSGFSGSVQ

FVPAQNSKSAYKPAYYTKDTNNNLTLVPAVVGKPGS

DVYYAGLNYKNG<u>GFAG</u>NYAF<u>KYAR</u>HANVGRNAFELF

LIGSATSDEAKGTDPLKNHQVHRLTGGYEEGGLNLA

LAAQLDLSENGDKAKTKNSTT<u>EIAAT</u>ASYRFGNAVP

RISYAHGF<u>DLIE</u>RGKKGENTSYDQIIAGVDYDFSKR

TSAIVS<u>GAWLK</u>RNTGIGNYTQINAASVGLRHKF

TABLE 8

SUMMARY OF PREDICTED T CELL EPITOPES SYNTHESIZED.

|   | RESIDUE NO. | SEQUENCE |
|---|---|---|
| 1. | 16–34 | NIQAQLTEQPQVTNGVQGN (SEQ ID NO:41) |
| 2. | 47–59 | TKISDFGSFIGFK (SEQ ID NO:42) |
| 3. | 57–71 | GFKGSEDLGEGLKAV (SEQ ID NO:43) |
| 4. | 78–90 | VSVAGGGASQWGN (SEQ ID NO:44) |
| 5. | 103–121 | TLRAGRVANQFDDASQAIN (SEQ ID NO:45) |
| 6. | 124–137 | DSNNDVASQLGIFK (SEQ ID NO:46) |
| 7. | 151–158 | GGFSGFSG (SEQ ID NO:47) |
| 8. | 176–185 | YYTKDTNNNL (SEQ ID NO:17) |
| 9. | 190–202 | AVVGKPGSDVYYA (SEQ ID NO:48) |
| 10. | 215–228 | YAFKYARNAHVGRN (SEQ ID NO:49) |
| 11. | 223–245 | ANVGRNAFELFLIGSATSDEAKG (SEQ ID NO:50) |
| 12. | 241–261 | DEAKGTDPLKNHQVHRLTGGY (SEQ ID NO:51) |
| 13. | 276–291 | LSENGDKAKTKNSTTE (SEQ ID NO:52) |
| 14. | 304–322 | VPRISYAHGFDLIERGKKG (SEQ ID NO:53) |
| 15. | 317–329 | ERGKKGENTSYDQ (SEQ ID NO:54) |
| 16. | 352–366 | KRNTGIGNYTQINAA (SEQ ID NO:55) |

TABLE 9

SUMMARY OF LYMPHOCYTE RESPONSES TO MENINGOCOCCAL SYNTHETIC PEPTIDES IN HLA TYPED VOLUNTEERS.

| VOLUNTEER/HLA TYPE | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| IMMUNIZED VOLUNTEERS | | | | | | | | | | | | | | | | |
| 1. DR4, W10, W53 | − | − | | | | | | + | − | − | − | | − | | − | − |
| 2. DR3, W52 | | | | | − | + | | + | − | | + | | | | | |
| 3. DR3, 7, W52, W53 | − | − | | | | | − | + | − | − | − | − | | + | | − |
| 4. DR2, W6, W13, W15, W52 | | + | − | | − | | + | − | − | | | | | | − | |
| 5. DR5, W11, 7, W52, W53 | + | − | | | | − | | + | − | | + | − | | + | | ± |
| 6. DR5, W11, W10, W52 | | | | | | | | | | | | | | | | |
| NON-IMMUNIZED CONTROL VOLUNTEERS | | | | | | | | | | | | | | | | |
| 7. NOT TYPED | − | − | − | + | − | + | − | ± | − | − | ± | − | ± | − | − | − |
| 8. DRW13, W6, W52 | − | − | − | − | − | − | − | − | − | − | − | − | − | − | − | − |
| 9. DR2, W15, 4, W53 | | − | | | − | | | − | − | | ± | | | − | − | − |
| 10. NOT TYPED | | − | − | − | − | − | − | − | − | − | − | − | − | − | − | − |
| 11. NOT TYPED | | | | − | | − | | − | + | − | − | | − | − | − | − |
| 12. DR2, W15, 3, W52 | − | + | − | | − | − | − | − | − | − | + | − | − | − | − | − |
| 13. DR5, W11, W52 | − | − | | − | − | | + | − | − | − | − | − | − | − | − | − |
| 14. DR3, 7, W52, W53 | − | − | − | − | | − | | + | − | − | − | − | − | + | − | − |
| 15. DR3, 4, W52, W53 | − | − | − | | − | + | − | − | − | − | − | − | − | − | − | − |
| 16. DR3, W12, 5, W52 | | | | | | | | | | | | | | | | |
| 17. DR2, W15, 7, W53 | | | | | | | | | | | | | + | | | |
| 18. DR1, 3, W52 | | | | | | | | | | | | | | | | |
| 19. DR3, 4, W52, W53 | | | | | | | | + | | | | | | | | |
| 20. DR1, 7, W53 | | | | | | | | | | | ± | | | | | |
| 21. DR4, W8, W52, W53 | | | | | | | | | | | | | | | | |
| 22. DR1, W13, W6, W52 | | | | | | | | | | | | | | | | |
| 23. DR2, W16, 5, W11, W52 | | | | | | ± | | + | | | + | + | | | | |
| 24. DR5, W11, W6, W13, W52 | | | | | | | | ± | | | ± | | | | | |
| 25. DR1, 3 W52 | | | | | | | | ± | | | | | | | | |
| 26. DR1, W6, W13, W52 | | + | + | | | | | | | | | | | | | |
| 27. DRW6, W13, W52 | | | | | | | | | | | | | | | | |
| 28. DRW6, W13, W52 | | | | | | | | + | | | | | | | | |

The responses were scored as follows −, SI < 2; ±, 2 < SI < 3 and +, SI > 3.

TABLE 10

PRESENTATION OF A SYNTHETIC PEPTIDE TO PERIPHERAL BLOOD LYMPHOCYTES IS ENHANCED BY A MONOCLONAL ANTIBODY RECOGNIZING REGION 179–184 OF MENINGOCOCCAL CLASS[1] OMP.

| IN VITRO CHALLENGE | CPM |
|---|---|
| GGYYTKDTNNNL (SEQ ID NO:56) | 3,017 |
| GGYYT<u>KDTNNNL</u>* + MN5C11G (1:200) | 22,836 |
| GGYYT<u>KDTNNNL</u> + MN5C11G (1:1000) | 12,608 |
| MEDIA | 330 |

*Underline region indicates sequence recognized by monoclonal antibody MN5C11G.

TABLE 11

RECOGNITION OF OMP FROM DIFFERENT MENINGOCOCCAL STRAINS BY HUMAN T-CELL CLONES

| STRAIN | SUB-TYPE | RESPONSE OF HUMAN T CELL CLONES (CPM × $10^{-3}$) | | | | | | |
|---|---|---|---|---|---|---|---|---|
| | | 5-5 | 5-7 | 5-9 | 5-12 | 5-13 | 5-14 | 5-15 |
| H44-76 | P1.16 | 6.0 | 1.2 | 6.8 | 2.6 | 2.3 | 9.5 | 1.5 |
| SWISS 4 | P1.15 | 4.9 | 1.0 | 10.1 | 6.9 | 3.6 | 10.5 | 1.4 |
| 395 | P1.9 | 5.2 | 1.5 | 4.8 | 1.5 | 6.1 | 13.1 | 1.4 |
| 2996 | P1.2 | 5.4 | 1.0 | 3.7 | 2.3 | 3.4 | 11.8 | 1.0 |
| M990 | P1.6 | 3.6 | 0.4 | 3.5 | 2.5 | 0.9 | 4.7 | 0.6 |
| 187 | P1.1 | 4.4 | 0.7 | 4.5 | 3.1 | 1.6 | 6.2 | 1.4 |
| 6557 | P1.17 | 3.7 | 2.0 | 8.2 | 4.2 | 1.7 | 6.2 | 0.8 |
| MEDIA | — | <0.1 | <0.1 | <0.1 | <0.1 | <0.1 | <0.1 | <0.1 |

EXAMPLE 17

Construction of Protein Model for Membrane Topology of Class 1 OMP and Comparison to Other Pathogenic Gram Negative Porin Proteins for Vaccine Development A model was constructed using the principles recognized for the structure of several *Escherichia coli* outer membrane Proteins (Vogel, H. et al. (1986) supra Ferenci, T. et al. (1988) supra; and Tommassen, J. (1988) supra). The central assumption is that protein segments spanning the outer membrane form beta-sheets. Specifically, in the case of Class 1 protein, the division in exposed and transmembrane segments was arrived at in the following way:

1. A comparison of the amino acid sequence of Class 1 protein (subtype P1.16) with those of the gonococcal PIA and PIB proteins (Carbonetti, N. H. et al. (1987) *PNAS* 84:9084; Carbonetti, N. H. et al. (1988) *PNAS* 85:6841; and Gotschlich, E. C. et al. (1987) *PNAS* 84:8135) reveals 34% identity. In the model, the variable sequences form the surface-exposed parts, whereas the conserved regions are placed mostly in the outer membrane and periplasm. Thus, the latter two areas consist for 58% of residues that are conserved among all proteins, 2. The hydrophilic maxima observed in a hydropathy profile (Kyte, J. et al. (1982) *J. Mol. Biol.* 157:105) to correspond to exposed regions.
3. The transmembrane segments should preferentially be able to form amphipathic beta-stands of 9–12 residues, with at least one side consisting entirely of hydrophobic residues. These conditions are met in 12 of the 16 membrane-spanning segments.
4. The number of residues at the periplasmic side is minimized.

FIG. 11 shows the model for the folding of Class 1 protein in the outer membrane. The sequence shown is for subtype P1.16. The top part of the figure shows the surface-exposed regions, whereas the central part indicates the presumed transmembrane segments, whose length is set at ten. Amino acid are shown alternating where they can form an amphipathic beta-strand. This model contains eight surface loops, whereby the first and the fourth loop contain the type-specific and protective variable region epitopes. These epitopes, as has been shown when formulated into a vaccine, can elicit a protective immune response. Loop 5 is constant and has been shown to elicit cross-reactive antibodies to other OMPs and is useful for vaccine formulation.

The one or two variable epitope regions of the individual proteins are located on so called surface loops of these membrane proteins. Such porin outer-membrane proteins contain more than two surface loops. This implicates that there are surface loops which have near identical amino acid sequence in the different Class 1 outer-membrane proteins as well. This opens the way to use of common peptides of the Class 1 outer-membrane protein for vaccine objectives as well. More especially a schematic two-dimensional model of the meningococci Class 1 outer-membrane protein P1.16 is illustrated in FIG. 11 (see also SEQ ID NO:5). This model contains eight surface loops, whereby the first and the fourth loop contain the type specific epitopes as shown on the basis of strain subtyping results. The fifth surface loop represents the constant region described above. Antibody to the constant region of loop 5 appears to react with *N. meningitidis* OMP complex. The amino sequence of Class 1 OMP, as derived, was compared to the Class 2 OMP of *N. meningitidis* (Murakami, K. et al., (1989), *Infect. Immun.*, 57:2318) and the porin PIA and PIB proteins of *N. gonorrhoeae*. With similar principle as used for the Class 1 OMP modeling, the sequences were aligned as follows:

LOOP 1

```
Class 1  (SEQ ID NO:57)    DVSLYGEIKAG  VEGRNIQAQLTEQPQVTNGVQGN
                           ** *** ****  *
Class 1B (SEQ ID NO:58)    DVTLYGAIKAG  V-------------QTYRSVEHT
                           ** *** ****  *
Class 1A (SEQ ID NO:59)    DVTLYGTIKAG  VEGRNIQAQLTEQPETSRSVAHH
                           ** *** ****  *
Class 2  (SEQ ID NO:60)    DVTLYGTIKAGV EGRNIQAQLTEQPEVSRVKDAG
                           ** *** *****

QVKVTKAKSRIRTKI   SDFGSTIGFKGSEDLGEGL
       *          * ** ***** **** **
DGKVSKVET--GSEI   ADFGSKIGFKGQEDLGNGL
       *          ** ***** ** * **
GAQADRVKT--ATEI   ADLGSRIGFKGQEDLGNGL
       *          * ** ***** ** * **
TYKAQGGKSKTATQ    IADFGSKIGFKGQEDLGNGL
                  *  * ** ***** ** * **
```

LOOP 2

```
KAVWQLEQD  VSVAGGGASQWGN   RESFIGLAGEFG
** *****    *       ***    ** ** * **
KAVWQLEQG  ASVAGTNTG-WGN   KQSFVGLKGGFG
** *****    *       ***    ** ** * **
KAIWQLEQK  AYVSGTDTG-WGN   RQSFIGLKGGFG
** *****    *       ***    ** ** * **
KAIWQLEQ   KASIAGTNSG-WGNRQSFIGLKGGFG
** *****       *        ***   ** ** * **
```

-continued

LOOP 3

```
TLRAGRVANQFDD  ASQAINPWDSNNDVASQLQI-
   * *
TIRAGSLNSPLKN  TGANVNAWESGKFTGNVLEIS
   * *
KVRVGRLNSYLKD  TGGFNPWEGKSYYLPLSNIAQ
   * *
TVRAGNLNTVLKDSGDNVNAWESGSNTEDVLGLG
   * *
```

LOOP 4

```
-FKRHDD MPV  SVRYDSPEFSGFSGSVQFV  PAQNS
             ******  **    *     *  **
GMAQREH RYL  SVRYDSPEFAGFSGSVQYA  PKDNS
             ******  **    *     *  **
PEERHV-- --  SVRYDSPEFAGFRAV-QYV  PNDNS
             ******  **    *     *  **
TIGRVESREI   SVRYDSPVFAGFSGSVQ    YVPRDNA
             ******  **    *      *  **

KSAYKPAYYTKDTNNNLTLVPAVVGKPGS  DVYYA
                                 *
GS------------------------NG   ESYHV
                                 *
GK------------------------NHS  ESYHA
                                 *
ND---------------VDKYKHTKSSR   ESYHA
                                 *
```

LOOP 5

```
GLNYKNGGFAGNYAFKYA  RHANVGRNAFELFLIG
* ** * *  **
GLNYQNSGFFAQYAGLFQ  RYGEGTKK------IE
* ** * *  **
GFNYKNSGFFVQYAGFYK  RHSYTTEKHFELFL--
* ** * *  **
GLKYENAGFFGQYA      GSFAKYADLNTD------AE
* ** * *  **
                    N
SATSDEAKGTDPLKH     QVERLTGGYEEGGLNLALA
                    ***** ***    *   *
DDQTYSIPSLFVEKL     QVHRLVGGYDNNALYVSVA
                    ***** ***    *   *
--------------L     QVHRLVGGYDHDALYASVA
                    ***** ***    *   *
RVAVNTANAHPVKDY     QVHRVAGYDANDLYVSVA
                    ***** ***    *   *
```

LOOP 6

```
AQLD  LSE--NGDKAKTKNSTTE    IAATASYRFGNA
 *              *           **** *****

AQQQ  DAKLYGAMSGNSHNSQTE    VAATAAYRFGNV
 *              *           **** *****

VQQQ  DAKLTWRND-NSHNSQTE    VAATAAYRFGNV
 *              *  *        **** ****

GQ    YEAAKNNEVGSTKGKKHQTQ  VAATAAYRFGNV
 *              E  *        **** *****
```

LOOP 7

```
VPRISYAHGFDLI  ERGKKGENTSYDQ   IIAGVDYD
** ******          -   * *       **

TPRVSYAHGFKGT  VDSANHDNT-YDQ   VVVGAEYD
** ******          *   * *       **

TPRVSYAHGFKGS  VYDADNDNT-YDQ   VVVGAEYD
** ******          *   * *       **

TPRVSYAHGF     KAKVNGVKDANYQQDQ  VIVGADYD
** ******            *   *     *  **
```

LOOP 8

```
FSKRTSAIVSGAWL  KRNTGIGNYTQIN   AASVGLRHKF
******* ** **        *          * *****

FSKRTSALVSAGWL  QGGKGADKIV-ST   ASAVVLRHKF
******* ** **        *          * *****

FSKRTSALVSAGWL  QRGKGTEKFV-AT   VGGVGLRHKF
******* ** **        *          * *****

FSKRTSALVSAGWL  KQGKGTGKVEQ-TASM  VGLRHKF
******* ** **        *          * *****
```

Structural similarities are indicated with transmembrane and surface loop regions. With the information now available for Class 1 OMP and information based on surface loop size, location, intraspecies amino acid homology or heterology of the loop regions of the particular porin protein, predictions of epitopes for incorporation into vaccines for other pathogenic gram negative bacteria including *N. gonorrhoeae* are possible. Using the same methods employed for Class 1 OMP, these epitopes can be evaluated for vaccine purposes.

Deposit of Microorganisms

The *N. meningitidis* strain H4476 (B:15:P1.7,16) was deposited on Dec. 12, 1989 in the Centraal Bureau voor Schimmelculturen (CBS), Baarn, The Netherlands and has deposit number CBS 635.89. The *N. meningitidis* Class 2/3 OMP deficient mutant HIII-5 was deposited on Dec. 12, 1989 in the CBS, Baarn, The Netherlands and has deposit number CBS 636.89.

Equivalents

Those skilled in the art will recognize, or be able to ascertain using no more than routine experimentation, many equivalents to the specific embodiments of the invention described herein. Such equivalents are intended to be encompassed by the following claims.

The invention claimed is:

1. An isolated nucleic acid comprising a nucleotide sequence selected from the group consisting of: SEQ ID NO:62, SEQ ID NO:64, SEQ ID NO:66, SEQ ID NO:68, SEQ ID NO:70, SEQ ID NO:72 and SEQ ID NO:74.

2. An isolated nucleic acid comprising a nucleotide sequence selected from the group consisting of SEQ ID NO:76, SEQ ID NO:78, SEQ ID NO:80, SEQ ID NO:82, SEQ ID NO:84, SEQ ID NO:86 and SEQ ID NO:88.

3. A nucleic acid vector comprising the nucleic acid of claim 1.

4. A nucleic acid vector comprising the nucleic acid of claim 2.

5. An isolated nucleic acid molecule encoding a protein or a peptide comprising amino acids 24–34 of SEQ ID NO:5.

6. A recombinant microorganism comprising a recombinant DNA vector, said vector expressing a peptide comprising an amino acid sequence selected from the group consisting of QPQVTNGVQGN (SEQ ID NO:22), PPSKSQP (SEQ ID NO:23), AQAANGGASG (SEQ ID NO:20), YYTKNTNNNLTL (SEQ ID NO:190), YYTKNTNNNL (SEQ ID NO:18), HFVQQTPQSQP (SEQ ID NO:21) AND HYTRQNNTDVF (SEQ ID NO:19).

7. A recombinant Neisseria meningitidis comprising a recombinant DNA vector, said vector expressing a Class 1 outer-membrane protein of Neisseria meningitidis, a fusion protein thereof, or an epitope of Neisseria meningitidis Class 1 outer-membrane protein which can be bound by antibodies against Neisseria meningitidis* Class 1 outer-membrane protein.

8. A recombinant *Neisseria meningitidis* expressing Class 1 outer membrane proteins of two subtypes of *Neisseria meningitidis.*

9. A recombinant microorganism comprising a recombinant DNA vector, said vector expressing one or more peptides comprising an amino acid sequence selected from the group consisting of: SEQ ID NO:61, SEQ ID NO:63, SEQ ID NO:65, SEQ ID NO:67, SEQ ID NO:69, SEQ ID NO:71 and SEQ ID NO:73.

10. A recombinant microorganism expressing a fusion protein comprising an amino acid sequence selected from the group consisting of: SEQ ID NO:61, SEQ ID NO:63, SEQ ID NO:65, SEQ ID NO:67, SEQ ID NO:69, SEQ ID NO:71 and SEQ ID NO:73.

11. A recombinant microorganism comprising a recombinant DNA vector, said vector expressing one or more peptides comprising an amino acid sequence selected from the group consisting of: SEQ ID NO:75, SEQ ID NO:77, SEQ ID NO:79, SEQ ID NO:81, SEQ ID NO:83, SEQ ID NO:85 and SEQ ID NO:87.

12. A recombinant microorganism expressing a fusion protein comprising an amino acid sequence selected from the group consisting of: SEQ ID NO:75, SEQ ID NO:77, SEQ ID NO:79, SEQ ID NO:81, SEQ ID NO:83, SEQ ID NO:85 and SEQ ID NO:87.

13. A recombinant microorganism comprising a recombinant DNA vector, said vector expressing a protein or a peptide, said protein or said peptide comprising one or more copies of a VR1 epitope of *Neisseria meningitidis* Class 1 outer membrane protein, wherein said protein or said peptide is fused to a carrier protein or a carrier peptide by genetic coupling techniques.

14. The microorganism of claim 13, wherein the carrier protein is a *Salmonella* flagellin.

15. The microorganism of claim 13, which is an *E. coli.*

16. The microorganism of claim 13, wherein the peptide is a decapeptide comprising said one copy of said VR1 epitope.

17. A recombinant microorganism comprising a vector, said vector expressing a protein comprising SEQ ID NO:5.

18. A recombinant microorganism comprising a vector, said vector expressing a protein comprising SEQ ID NO:6.

19. A recombinant microorganism comprising a recombinant DNA vector, said vector expressing a protein comprising SEQ ID NO:7.

20. A recombinant microorganism comprising a recombinant DNA vector, said vector expressing a protein comprising SEQ ID NO:8.

21. A microorganism comprising a recombinant DNA vector, said vector expressing a protein comprising amino acid residues 24–34 of SEQ ID NO:5.

22. A recombinant microorganism comprising a recombinant DNA vector, said vector expressing a protein comprising the amino acid sequence HFVQQTPQSQP (SEQ ID NO:21).

23. A recombinant *Escherichia coli* expressing a protein comprising SEQ ID NO:5.

24. A recombinant microorganism comprising a recombinant DNA vector, said vector expressing one or more protein(s), said protein(s) comprising SEQ ID NO:61, SEQ ID NO:63, SEQ ID NO:65, SEQ ID NO:67, SEQ ID NO:69, SEQ ID NO:71 or SEQ ID NO:73.

25. The recombinant microorganism of claim 24 which is *Escherichia coli.*

26. A recombinant microorganism comprising a recombinant DNA vector, said vector expressing one or more protein(s), said protein(s) comprising SEQ ID NO:75, SEQ ID NO:77, SEQ ID NO:79, SEQ ID NO:81, SEQ ID NO:83, SEQ ID NO:85 or SEQ ID NO:87.

27. The recombinant microorganism of claim 26 which is *Escherichia coli.*

28. A recombinant microorganism comprising a recombinant DNA vector, said vector expressing a peptide comprising an amino acid sequence selected from the group consisting of PPSKSQP (SEQ ID NO:23), AQAANGGASG (SEQ ID NO:20), YYTKNTNNNLTL (SEQ ID NO:190), YYTKNTNNNL (SEQ ID NO:18), HFVQQTPQSQP (SEQ ID NO:21) and HYTRQNNTDVF (SEQ ID NO:19).

29. The recombinant microorganism of claim 13, wherein said VR1 epitope consists of the amino acid sequence AQAANGGSG (SEQ ID NO:20).

30. A method for producing one or more *Neisseria meningitidis* Class 1 outer membrane protein(s), said method comprising culturing in a culture medium recombinant *Escherichia coli* bacteria or recombinant *Salmonella* bacteria which express the one or more *Neisseria meningitidis* Class 1 outer membrane protein(s), said protein(s) comprising SEQ ID NO:5, SEQ ID NO:6, SEQ ID NO:7 or SEQ ID NO:8, under conditions in which said protein(s) are produced.

31. The method of claim 30, further comprising harvesting the *Escherichia coli* bacteria or the *Salmonella* bacteria from the culture medium, and extracting said protein(s) from the bacteria.

* * * * *

UNITED STATES PATENT AND TRADEMARK OFFICE
CERTIFICATE OF CORRECTION

| | |
|---|---|
| PATENT NO. | : 7,238,345 B1 |
| APPLICATION NO. | : 08/461651 |
| DATED | : July 3, 2007 |
| INVENTOR(S) | : Robert C. Seid, Jr. et al. |

It is certified that error appears in the above-identified patent and that said Letters Patent is hereby corrected as shown below:

In Claim 29, in column 131, line 6, delete "AQAANGGSG" and insert in its place --AQAANGGASG--.

Signed and Sealed this

Eighteenth Day of September, 2007

JON W. DUDAS
*Director of the United States Patent and Trademark Office*